US012357467B2

United States Patent
Schmura et al.

(10) Patent No.: US 12,357,467 B2
(45) Date of Patent: *Jul. 15, 2025

(54) ARCUATE FIXATION MEMBER

(71) Applicant: DePuy Synthes Products, Inc., Raynham, MA (US)

(72) Inventors: Kurt Schmura, Middleboro, MA (US); Thomas Donner, Thibodaux, LA (US); Lawton Laurence, Phoenixville, PA (US); Wamis Singhatat, Malvern, PA (US); Jared Schoenly, Spring City, PA (US); David E. Evans, Atlanta, GA (US); William Miller, Middleboro, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 736 days.

This patent is subject to a terminal disclaimer.

(21) Appl. No.: 16/922,739

(22) Filed: Jul. 7, 2020

(65) Prior Publication Data

US 2020/0337854 A1    Oct. 29, 2020

Related U.S. Application Data

(63) Continuation of application No. 16/131,081, filed on Sep. 14, 2018, now Pat. No. 10,716,680, which is a
(Continued)

(51) Int. Cl.
  *A61F 2/44* (2006.01)
  *A61B 17/70* (2006.01)
  (Continued)

(52) U.S. Cl.
  CPC ............ *A61F 2/4455* (2013.01); *A61B 17/70* (2013.01); *A61B 17/7044* (2013.01);
  (Continued)

(58) Field of Classification Search
  CPC .. A61F 2/44–447; A61F 2/4611; A61B 17/70; A61B 17/7032; A61B 17/7037;
  (Continued)

(56) References Cited

U.S. PATENT DOCUMENTS 2,916,956 A    12/1959 Salomon
2,984,949 A    5/1961 Dayton et al.
(Continued)

FOREIGN PATENT DOCUMENTS

CA    2279936 A1    8/1998
CA    2279938 C    1/2006
(Continued)

OTHER PUBLICATIONS

International Patent Application No. PCT/US2010/031244: International Search Report dated Nov. 3, 2010, 10 pages.
(Continued)

*Primary Examiner* — Nicholas J Plionis
(74) *Attorney, Agent, or Firm* — BakerHostetler

(57) ABSTRACT

Arcuate fixation members with varying configurations and/or features are provided, along with additional components for use therewith in provided fixation systems and intervertebral implant systems. The arcuate fixation members may be of varying lengths, cross sectional geometries, and/or cross sectional areas, and may be configured with various features such as heads configured to accept other fixation system components, tabs to allow arcuate fixation member-in-arcuate fixation member or fixation anchor-in-arcuate fixation member configurations. Applications of fixation systems and intervertebral implants systems utilizing arcuate fixation members are particularly suitable when a linear line-of-approach for delivering fixation members is undesirable.

20 Claims, 33 Drawing Sheets

Related U.S. Application Data continuation of application No. 15/225,537, filed on Aug. 1, 2016, now Pat. No. 10,105,236, which is a continuation of application No. 12/761,101, filed on Apr. 15, 2010, now Pat. No. 9,408,715.

(60) Provisional application No. 61/169,461, filed on Apr. 15, 2009.

(51) Int. Cl.
| | |
|---|---|
| *A61B 17/80* | (2006.01) |
| *A61B 17/92* | (2006.01) |
| *A61F 2/46* | (2006.01) |
| *A61B 17/86* | (2006.01) |
| *A61F 2/00* | (2006.01) |
| *A61F 2/28* | (2006.01) |
| *A61F 2/30* | (2006.01) |

(52) U.S. Cl.
CPC ...... *A61B 17/7056* (2013.01); *A61B 17/7076* (2013.01); *A61B 17/8042* (2013.01); *A61B 17/8052* (2013.01); *A61B 17/92* (2013.01); *A61F 2/4611* (2013.01); *A61B 17/7032* (2013.01); *A61B 17/7037* (2013.01); *A61B 2017/8655* (2013.01); *A61F 2002/0081* (2013.01); *A61F 2/28* (2013.01); *A61F 2002/2835* (2013.01); *A61F 2002/30306* (2013.01); *A61F 2002/30387* (2013.01); *A61F 2002/30507* (2013.01); *A61F 2002/30514* (2013.01); *A61F 2002/30517* (2013.01); *A61F 2002/30578* (2013.01); *A61F 2002/30593* (2013.01); *A61F 2002/30604* (2013.01); *A61F 2002/30616* (2013.01); *A61F 2/30744* (2013.01); *A61F 2/30749* (2013.01); *A61F 2/30771* (2013.01); *A61F 2002/30777* (2013.01); *A61F 2002/30784* (2013.01); *A61F 2002/30787* (2013.01); *A61F 2002/30841* (2013.01); *A61F 2002/30843* (2013.01); *A61F 2002/30845* (2013.01); *A61F 2002/30879* (2013.01); *A61F 2002/30904* (2013.01); *A61F 2/30965* (2013.01); *A61F 2/442* (2013.01); *A61F 2/4465* (2013.01); *A61F 2002/4615* (2013.01); *A61F 2002/4627* (2013.01); *A61F 2002/4628* (2013.01); *A61F 2220/0008* (2013.01); *A61F 2220/0016* (2013.01); *A61F 2220/0025* (2013.01); *A61F 2230/0097* (2013.01); *A61F 2310/00017* (2013.01); *A61F 2310/00023* (2013.01); *A61F 2310/00131* (2013.01); *A61F 2310/00359* (2013.01)

(58) Field of Classification Search
CPC ............ A61B 17/7076; A61B 17/8052; A61B 2017/8655
See application file for complete search history.

(56) References Cited

U.S. PATENT DOCUMENTS

| | | |
|---|---|---|
| 3,791,380 A | 2/1974 | Dawidowski |
| 3,875,595 A | 4/1975 | Froning |
| 3,948,262 A | 4/1976 | Zaffaroni |
| 4,349,921 A | 9/1982 | Kuntz |
| 4,507,115 A | 3/1985 | Kambara et al. |
| 4,599,086 A | 7/1986 | Doty |
| 4,714,469 A | 12/1987 | Kenna |
| 4,721,103 A | 1/1988 | Freedland |
| 4,790,303 A | 12/1988 | Steffee |
| 4,834,757 A | 5/1989 | Brantigan |
| 5,263,953 A | 11/1993 | Bagby |
| 5,300,074 A | 4/1994 | Frigg |
| 5,401,269 A | 3/1995 | Buettner-Janz et al. |
| 5,417,712 A | 5/1995 | Whittaker et al. |
| 5,458,638 A | 10/1995 | Kuslich et al. |
| 5,522,845 A | 6/1996 | Wenstrom, Jr. |
| 5,522,899 A | 6/1996 | Michelson |
| 5,609,635 A | 3/1997 | Michelson |
| 5,658,335 A | 8/1997 | Allen |
| 5,683,394 A | 11/1997 | Rinner |
| 5,800,547 A | 9/1998 | Schaefer et al. |
| 5,800,550 A | 9/1998 | Sertich |
| 5,810,820 A | 9/1998 | Santori et al. |
| 5,849,004 A | 12/1998 | Bramlet |
| 5,888,223 A | 3/1999 | Bray, Jr. |
| 5,888,228 A | 3/1999 | Knothe et al. |
| 5,889,905 A | 3/1999 | Leone |
| 5,899,905 A | 5/1999 | Errico et al. |
| 6,036,701 A | 3/2000 | Rosenman |
| 6,113,638 A | 9/2000 | Williams et al. |
| 6,120,503 A | 9/2000 | Michelson |
| 6,136,001 A | 10/2000 | Michelson |
| 6,139,550 A | 10/2000 | Michelson |
| 6,179,873 B1 | 1/2001 | Zientek |
| 6,193,721 B1 | 2/2001 | Michelson |
| 6,210,442 B1 | 4/2001 | Wing et al. |
| 6,214,050 B1 | 4/2001 | Huene |
| 6,231,610 B1 | 5/2001 | Geisler |
| 6,235,059 B1 | 5/2001 | Benezech et al. |
| 6,258,089 B1 | 7/2001 | Campbell et al. |
| 6,364,880 B1 | 4/2002 | Michelson |
| 6,371,987 B1 | 4/2002 | Weiland et al. |
| 6,383,186 B1 | 5/2002 | Michelson |
| 6,398,783 B1 | 6/2002 | Michelson |
| 6,413,259 B1 | 7/2002 | Lyons et al. |
| 6,416,528 B1 | 7/2002 | Michelson |
| 6,423,063 B1 | 7/2002 | Bonutti |
| 6,428,542 B1 | 8/2002 | Michelson |
| 6,432,106 B1 | 8/2002 | Fraser |
| 6,447,546 B1 | 9/2002 | Bramlet et al. |
| 6,454,771 B1 | 9/2002 | Michelson |
| 6,468,309 B1 | 10/2002 | Lieberman |
| 6,527,774 B2 | 3/2003 | Lieberman |
| 6,527,776 B1 | 3/2003 | Michelson |
| 6,527,803 B1 | 3/2003 | Crozet et al. |
| 6,551,319 B2 | 4/2003 | Lieberman |
| 6,558,423 B1 | 5/2003 | Michelson |
| 6,592,586 B1 | 7/2003 | Michelson |
| 6,616,666 B1 | 9/2003 | Michelson |
| 6,620,163 B1 | 9/2003 | Michelson |
| 6,626,907 B2 | 9/2003 | Campbell et al. |
| 6,695,846 B2 | 2/2004 | Richelsoph et al. |
| 6,712,818 B1 | 3/2004 | Michelson |
| 6,746,450 B1 | 6/2004 | Wall et al. |
| 6,767,367 B1 | 7/2004 | Michelson |
| 6,770,096 B2 | 8/2004 | Bolger et al. |
| 6,800,092 B1 | 10/2004 | Williams et al. |
| 6,916,320 B2 | 7/2005 | Michelson |
| 6,923,830 B2 | 8/2005 | Michelson |
| 6,926,718 B1 | 8/2005 | Michelson |
| 6,936,050 B2 | 8/2005 | Michelson |
| 6,936,051 B2 | 8/2005 | Michelson |
| 6,953,462 B2 | 10/2005 | Lieberman |
| 6,969,390 B2 | 11/2005 | Michelson |
| 6,981,975 B2 | 1/2006 | Michelson |
| 7,037,340 B2 | 5/2006 | Gau |
| 7,041,135 B2 | 5/2006 | Michelson |
| 7,051,610 B2 | 5/2006 | Stoianovici et al. |
| 7,056,344 B2 | 6/2006 | Huppert et al. |
| 7,060,097 B2 | 6/2006 | Fraser et al. |
| 7,074,221 B2 | 7/2006 | Michelson |
| 7,077,844 B2 | 7/2006 | Michelson |
| 7,112,206 B2 | 9/2006 | Michelson |
| 7,137,984 B2 | 11/2006 | Michelson |
| 7,172,627 B2 | 2/2007 | Fiere et al. |
| 7,195,643 B2 | 3/2007 | Jackson |
| 7,223,289 B2 | 5/2007 | Trieu et al. |
| 7,255,698 B2 | 8/2007 | Michelson |
| 7,290,972 B2 | 11/2007 | Gauthier |
| 7,291,170 B2 | 11/2007 | Huppert |

(56) References Cited

U.S. PATENT DOCUMENTS

| | | |
|---|---|---|
| 7,303,583 B1 | 12/2007 | Schaer et al. |
| 7,326,250 B2 | 2/2008 | Beaurain et al. |
| 7,455,684 B2 | 11/2008 | Gradel et al. |
| 7,473,276 B2 | 1/2009 | Aebi et al. |
| 7,494,508 B2 | 2/2009 | Zeegers |
| 7,507,248 B2 | 3/2009 | Beaurain et al. |
| 7,563,284 B2 | 7/2009 | Coppes et al. |
| 7,563,286 B2 | 7/2009 | Gerber et al. |
| 7,594,931 B2 | 9/2009 | Louis et al. |
| 7,594,932 B2 | 9/2009 | Aferzon et al. |
| 7,625,381 B2 | 12/2009 | Michelson |
| 7,632,282 B2 | 12/2009 | Dinville |
| 7,637,950 B2 | 12/2009 | Baccelli et al. |
| 7,651,497 B2 | 1/2010 | Michelson |
| 7,662,182 B2 | 2/2010 | Zubok et al. |
| 7,662,185 B2 | 2/2010 | Alfaro et al. |
| 7,682,396 B2 | 3/2010 | Beaurain et al. |
| 7,695,516 B2 | 4/2010 | Zeegers |
| 7,695,518 B2 | 4/2010 | Gau |
| 7,704,255 B2 | 4/2010 | Michelson |
| 7,842,088 B2 | 11/2010 | Rashbaum et al. |
| 7,846,188 B2 | 12/2010 | Moskowitz et al. |
| 7,846,207 B2 | 12/2010 | Lechmann et al. |
| 8,002,835 B2 | 8/2011 | Zeegers |
| 8,075,618 B2 | 12/2011 | Trieu et al. |
| 8,080,062 B2 | 12/2011 | Armstrong et al. |
| 8,147,556 B2 | 4/2012 | Louis et al. |
| 8,162,988 B2 | 4/2012 | Delecrin et al. |
| 8,221,422 B2 | 7/2012 | Mangione |
| 8,221,457 B2 | 7/2012 | Delecrin et al. |
| 8,241,359 B2 | 8/2012 | Davis et al. |
| 8,257,439 B2 | 9/2012 | Zeegers |
| 8,257,443 B2 | 9/2012 | Kamran et al. |
| 8,262,700 B2 | 9/2012 | Cho et al. |
| 8,267,999 B2 | 9/2012 | Beaurain et al. |
| 8,303,663 B2 | 11/2012 | Jimenez et al. |
| 8,313,528 B1 | 11/2012 | Wensel |
| 8,323,345 B2 | 12/2012 | Sledge |
| 8,328,872 B2 | 12/2012 | Duffield et al. |
| 8,333,804 B1 | 12/2012 | Wensel |
| 8,343,197 B2 | 1/2013 | Gonzalez-Hernandez |
| 8,343,219 B2 | 1/2013 | Allain et al. |
| 8,353,219 B2 | 1/2013 | Brackett et al. |
| 8,409,288 B2 | 4/2013 | Davis et al. |
| 8,430,915 B2 | 4/2013 | Beaurain et al. |
| 8,439,931 B2 | 5/2013 | Dinville |
| 8,465,546 B2 | 6/2013 | Jodaitis et al. |
| 8,535,352 B2 | 9/2013 | Altarac et al. |
| 8,545,563 B2 | 10/2013 | Brun et al. |
| 8,617,245 B2 | 12/2013 | Brett |
| 8,641,766 B2 | 2/2014 | Donner et al. |
| 8,642,766 B2 | 2/2014 | Shenvi et al. |
| 9,408,715 B2 | 8/2016 | Donner et al. |
| 9,445,913 B2 | 9/2016 | Donner et al. |
| 9,539,110 B2 | 1/2017 | Bergey |
| 9,925,056 B2 | 3/2018 | Donner et al. |
| 11,617,654 B2 | 4/2023 | Donner et al. |
| 2002/0004683 A1 | 1/2002 | Michelson |
| 2002/0059938 A1 | 5/2002 | Fogarty et al. |
| 2002/0082597 A1 | 6/2002 | Fraser |
| 2002/0099376 A1 | 7/2002 | Michelson |
| 2003/0028249 A1 | 2/2003 | Baccelli et al. |
| 2003/0149484 A1 | 8/2003 | Michelson |
| 2003/0187436 A1 | 10/2003 | Bolger et al. |
| 2003/0195514 A1 | 10/2003 | Trieu et al. |
| 2003/0195627 A1 | 10/2003 | Ralph et al. |
| 2004/0010312 A1 | 1/2004 | Enayati |
| 2004/0054411 A1 | 3/2004 | Kelly et al. |
| 2004/0068258 A1 | 4/2004 | Schlapfer et al. |
| 2004/0082953 A1 | 4/2004 | Petit |
| 2004/0093087 A1 | 5/2004 | Ferree et al. |
| 2004/0210219 A1 | 10/2004 | Bray |
| 2004/0220569 A1 | 11/2004 | Wall et al. |
| 2005/0027362 A1 | 2/2005 | Williams et al. |
| 2005/0049590 A1 | 3/2005 | Alleyne et al. |
| 2005/0055027 A1 | 3/2005 | Yeung et al. |
| 2005/0101960 A1 | 5/2005 | Fiere et al. |
| 2005/0107788 A1 | 5/2005 | Beaurain et al. |
| 2005/0143825 A1 | 6/2005 | Enayati |
| 2005/0197706 A1 | 9/2005 | Hovorka et al. |
| 2005/0251258 A1 | 11/2005 | Jackson |
| 2005/0283236 A1 | 12/2005 | Razian |
| 2006/0022511 A1 | 2/2006 | Rompel |
| 2006/0030851 A1 | 2/2006 | Bray et al. |
| 2006/0085071 A1* | 4/2006 | Lechmann ............ A61F 2/4465 623/17.11 |
| 2006/0095071 A1 | 5/2006 | Zhang |
| 2006/0095136 A1 | 5/2006 | McLuen |
| 2006/0116676 A1 | 6/2006 | Gradel et al. |
| 2006/0241621 A1 | 10/2006 | Moskowitz et al. |
| 2006/0241764 A1 | 10/2006 | Michelson |
| 2006/0241778 A1 | 10/2006 | Ogilvie |
| 2006/0253201 A1 | 11/2006 | McLuen |
| 2006/0271053 A1 | 11/2006 | Schlapfer et al. |
| 2006/0276899 A1 | 12/2006 | Zipnick et al. |
| 2006/0282074 A1 | 12/2006 | Renaud et al. |
| 2007/0016295 A1 | 1/2007 | Boyd |
| 2007/0049943 A1 | 3/2007 | Moskowitz et al. |
| 2007/0106388 A1 | 5/2007 | Michelson |
| 2007/0162130 A1 | 7/2007 | Rashbaum et al. |
| 2007/0179623 A1 | 8/2007 | Trieu et al. |
| 2007/0208345 A1 | 9/2007 | Marnay et al. |
| 2007/0219635 A1 | 9/2007 | Mathieu et al. |
| 2007/0270960 A1 | 11/2007 | Bonin et al. |
| 2007/0270961 A1 | 11/2007 | Ferguson |
| 2008/0021562 A1 | 1/2008 | Huppert |
| 2008/0033432 A1 | 2/2008 | McGraw et al. |
| 2008/0132949 A1 | 6/2008 | Aferzon et al. |
| 2008/0177306 A1 | 7/2008 | Lamborne et al. |
| 2008/0234686 A1 | 9/2008 | Beaurain et al. |
| 2008/0249625 A1 | 10/2008 | Waugh et al. |
| 2008/0269768 A1 | 10/2008 | Schwager et al. |
| 2008/0281425 A1 | 11/2008 | Thalgott et al. |
| 2008/0306596 A1 | 12/2008 | Jones et al. |
| 2008/0312742 A1 | 12/2008 | Abernathie |
| 2008/0312743 A1 | 12/2008 | Vila et al. |
| 2009/0030520 A1 | 1/2009 | Biedermann et al. |
| 2009/0054988 A1 | 2/2009 | Hess |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1* | 4/2009 | Allain ................. A61F 2/4465 623/17.11 |
| 2009/0112271 A1 | 4/2009 | Moskowitz et al. |
| 2009/0118771 A1 | 5/2009 | Gonzalez-Hernandez |
| 2009/0149959 A1 | 6/2009 | Conner et al. |
| 2009/0164020 A1 | 6/2009 | Janowski et al. |
| 2009/0210062 A1 | 8/2009 | Thalgott et al. |
| 2009/0210064 A1 | 8/2009 | Lechmann et al. |
| 2009/0216331 A1 | 8/2009 | Grotz et al. |
| 2009/0265007 A1 | 10/2009 | Colleran |
| 2010/0010547 A1 | 1/2010 | Beaurain et al. |
| 2010/0016974 A1 | 1/2010 | Janowski et al. |
| 2010/0049259 A1 | 2/2010 | Lambrecht et al. |
| 2010/0050276 A1 | 2/2010 | Depaepe |
| 2010/0057206 A1 | 3/2010 | Duffield et al. |
| 2010/0145460 A1 | 6/2010 | Mcdonough et al. |
| 2010/0161057 A1 | 6/2010 | Berry et al. |
| 2010/0185289 A1 | 7/2010 | Kirwan et al. |
| 2010/0204796 A1 | 8/2010 | Bae et al. |
| 2010/0234958 A1 | 9/2010 | Linares |
| 2010/0280618 A1 | 11/2010 | Jodaitis et al. |
| 2010/0298941 A1 | 11/2010 | Hes et al. |
| 2010/0305700 A1 | 12/2010 | Ben-Arye et al. |
| 2010/0305704 A1 | 12/2010 | Messerli et al. |
| 2010/0312345 A1 | 12/2010 | Duffield et al. |
| 2010/0312346 A1 | 12/2010 | Kueenzi et al. |
| 2011/0054616 A1 | 3/2011 | Kamran et al. |
| 2011/0077739 A1 | 3/2011 | Rashbaum et al. |
| 2011/0112587 A1 | 5/2011 | Patel et al. |
| 2011/0166660 A1 | 7/2011 | Laurence |
| 2011/0178599 A1 | 7/2011 | Brett |
| 2011/0208311 A1 | 8/2011 | Janowski |
| 2011/0230971 A1 | 9/2011 | Donner et al. |

(56) References Cited

U.S. PATENT DOCUMENTS

| | | |
|---|---|---|
| 2012/0022654 A1 | 1/2012 | Farris et al. |
| 2012/0053693 A1 | 3/2012 | Zeegers |
| 2012/0078371 A1 | 3/2012 | Gamache et al. |
| 2012/0078373 A1 | 3/2012 | Gamache et al. |
| 2012/0116466 A1 | 5/2012 | Dinville et al. |
| 2012/0191196 A1 | 7/2012 | Louis et al. |
| 2012/0197404 A1 | 8/2012 | Brun et al. |
| 2012/0265248 A1 | 10/2012 | Delecrin et al. |
| 2012/0310356 A1 | 12/2012 | Davis et al. |
| 2012/0330424 A1 | 12/2012 | Zeegers |
| 2013/0013006 A1 | 1/2013 | Rashbaum et al. |
| 2013/0041408 A1 | 2/2013 | Dinville et al. |
| 2013/0150968 A1 | 6/2013 | Dinville et al. |
| 2013/0166029 A1 | 6/2013 | Dinville et al. |
| 2013/0204300 A1 | 8/2013 | Michelson |
| 2013/0226300 A1 | 8/2013 | Chataigner et al. |
| 2013/0253648 A1 | 9/2013 | Beaurain et al. |
| 2013/0253651 A1 | 9/2013 | Dinville |
| 2013/0345814 A1 | 12/2013 | Walkenhorst et al. |
| 2014/0074241 A1 | 3/2014 | McConnell |
| 2015/0025635 A1 | 1/2015 | Laubert |
| 2016/0081812 A1 | 3/2016 | Waugh et al. |
| 2017/0014244 A1 | 1/2017 | Seifert et al. |

FOREIGN PATENT DOCUMENTS

| | | |
|---|---|---|
| CA | 2445299 C | 1/2006 |
| CA | 2445303 C | 1/2006 |
| CA | 2445319 C | 1/2006 |
| CA | 2444232 C | 4/2006 |
| CA | 2444222 C | 5/2006 |
| CA | 2444226 C | 6/2006 |
| CA | 2523814 C | 2/2007 |
| CA | 2533689 C | 5/2007 |
| CA | 2533699 C | 5/2007 |
| CA | 2533695 C | 6/2007 |
| CA | 2533713 C | 6/2007 |
| CN | 1515234 A | 7/2004 |
| CN | 1620271 A | 5/2005 |
| CN | 101352367 A | 1/2009 |
| CN | 201244104 Y | 5/2009 |
| DE | 4327054 C1 | 4/1995 |
| EP | 0260044 A1 | 3/1988 |
| EP | 0667127 A1 | 8/1995 |
| EP | 0891169 B1 | 12/2005 |
| EP | 1402836 | 7/2006 |
| EP | 1690508 A2 | 8/2006 |
| EP | 1393688 B1 | 4/2007 |
| EP | 1393689 B1 | 8/2007 |
| EP | 1847229 A2 | 10/2007 |
| EP | 1393687 B1 | 12/2007 |
| EP | 1402833 B1 | 5/2008 |
| EP | 1006913 B2 | 3/2009 |
| EP | 2047825 A1 | 4/2009 |
| EP | 1402834 B1 | 1/2010 |
| EP | 1402832 B1 | 4/2011 |
| EP | 1402835 B1 | 9/2011 |
| EP | 2162098 B1 | 8/2015 |
| FR | 2727003 A1 | 5/1996 |
| FR | 2779941 A1 | 12/1999 |
| FR | 2848408 A1 | 6/2004 |
| FR | 2916956 A1 | 12/2008 |
| JP | 03-505416 A | 11/1991 |
| JP | 07-008514 A | 1/1995 |
| JP | 2796544 B2 | 9/1998 |
| JP | 11-506658 A | 6/1999 |
| JP | 2000-515041 A | 11/2000 |
| JP | 2001-187075 A | 7/2001 |
| JP | 2001-252283 A | 9/2001 |
| JP | 2002-518132 A | 6/2002 |
| JP | 2003-516174 A | 5/2003 |
| JP | 2004-500156 A | 1/2004 |
| JP | 2005-523074 A | 8/2005 |
| JP | 2006-510462 A | 3/2006 |
| JP | 2006-513752 A | 4/2006 |
| JP | 2006-230831 A | 9/2006 |
| JP | 2007-008514 A | 1/2007 |
| JP | 2007-090094 A | 4/2007 |
| JP | 2008-532730 A | 8/2008 |
| JP | 4167066 B2 | 10/2008 |
| JP | 2011-512893 A | 4/2011 |
| KR | 10-2010-0029755 A | 3/2010 |
| WO | 90/00037 A1 | 1/1990 |
| WO | 95/25469 A1 | 9/1995 |
| WO | 98/02105 A1 | 1/1998 |
| WO | 98/34553 A1 | 8/1998 |
| WO | 99/66867 A1 | 12/1999 |
| WO | 02/13732 A2 | 2/2002 |
| WO | 2002/058593 A2 | 8/2002 |
| WO | 2004/069106 A1 | 8/2004 |
| WO | 2004/080356 A2 | 9/2004 |
| WO | 2004/093767 A1 | 11/2004 |
| WO | 2005/092219 A1 | 10/2005 |
| WO | 2007/098288 A2 | 8/2007 |
| WO | 2007/127771 A2 | 11/2007 |
| WO | 2008/044057 A1 | 4/2008 |
| WO | 2008/102174 A2 | 8/2008 |
| WO | 2008/149223 A2 | 12/2008 |
| WO | 2009/004625 A2 | 1/2009 |
| WO | 2009/070721 A1 | 6/2009 |
| WO | 2009/131955 A1 | 10/2009 |
| WO | 2010/028045 A1 | 3/2010 |
| WO | 2010/121028 A2 | 10/2010 |
| WO | 2011/129973 A1 | 10/2011 |

OTHER PUBLICATIONS

International Patent Application No. PCT/US2011/029738: International Search Report dated Jun. 29, 2011, 12 pages.

International Search Report and the Written Opinion, The International Searching Authority, Patent Cooperation Treaty, PCT/US2010/049287; Jan. 11, 2011, 6 pages.

Synthes, "Synthes Global Interent: SynFix-LR", http://www.Synthes.com/html/SynFix-LR.6902.0.html, Copyrights 2009, accessed Sep. 16, 2009, 1 page.

U.S. Provisional Application Filed on Apr. 15, 2009 by Lawton Laurence, et al., entitled "Arcuate Blade", U.S. Appl. No. 61/169,461.

U.S. Provisional Application Filed on Dec. 5, 2008 by Tom Overes, Langendorf, et al., entitled "Anchor-In-Anchor System for Use in Bone Fixation", U.S. Appl. No. 61/120,138.

* cited by examiner

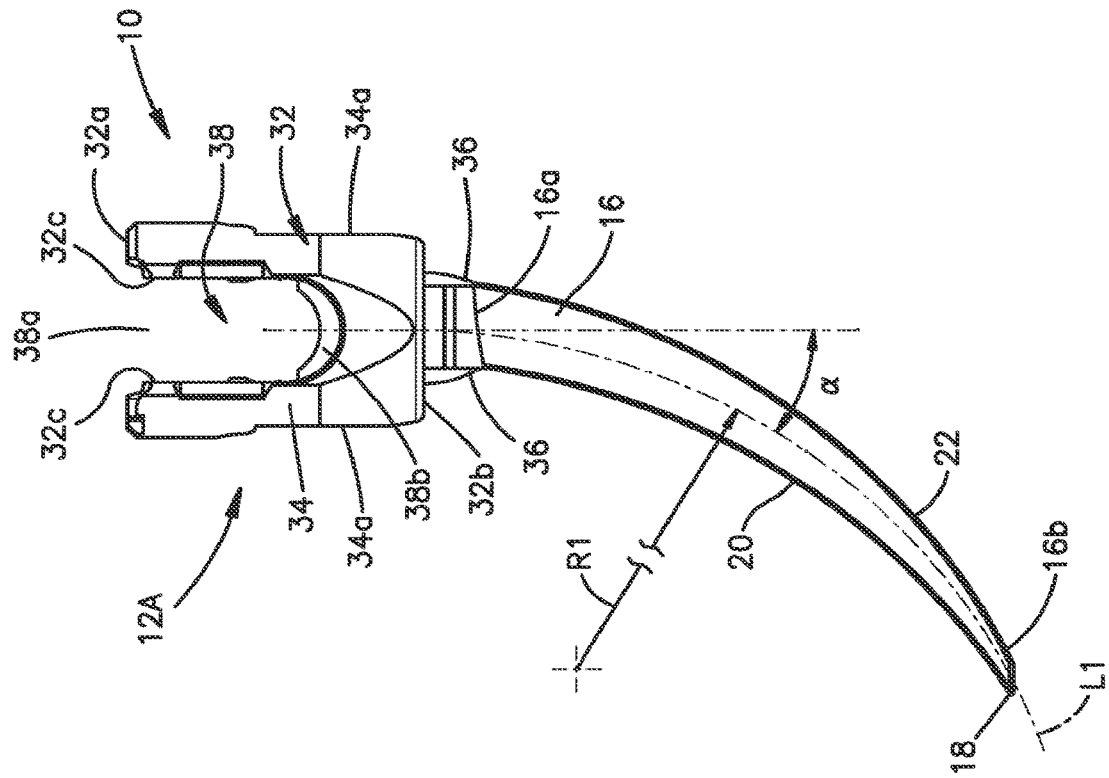
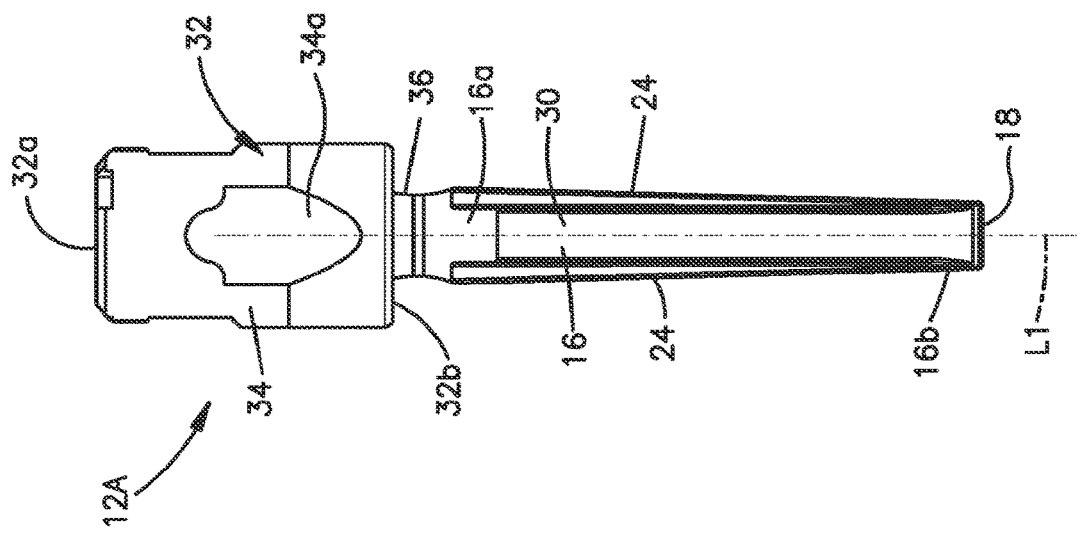
Figure 1B
Figure 1A

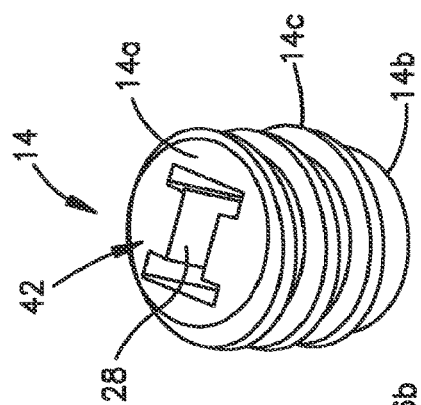
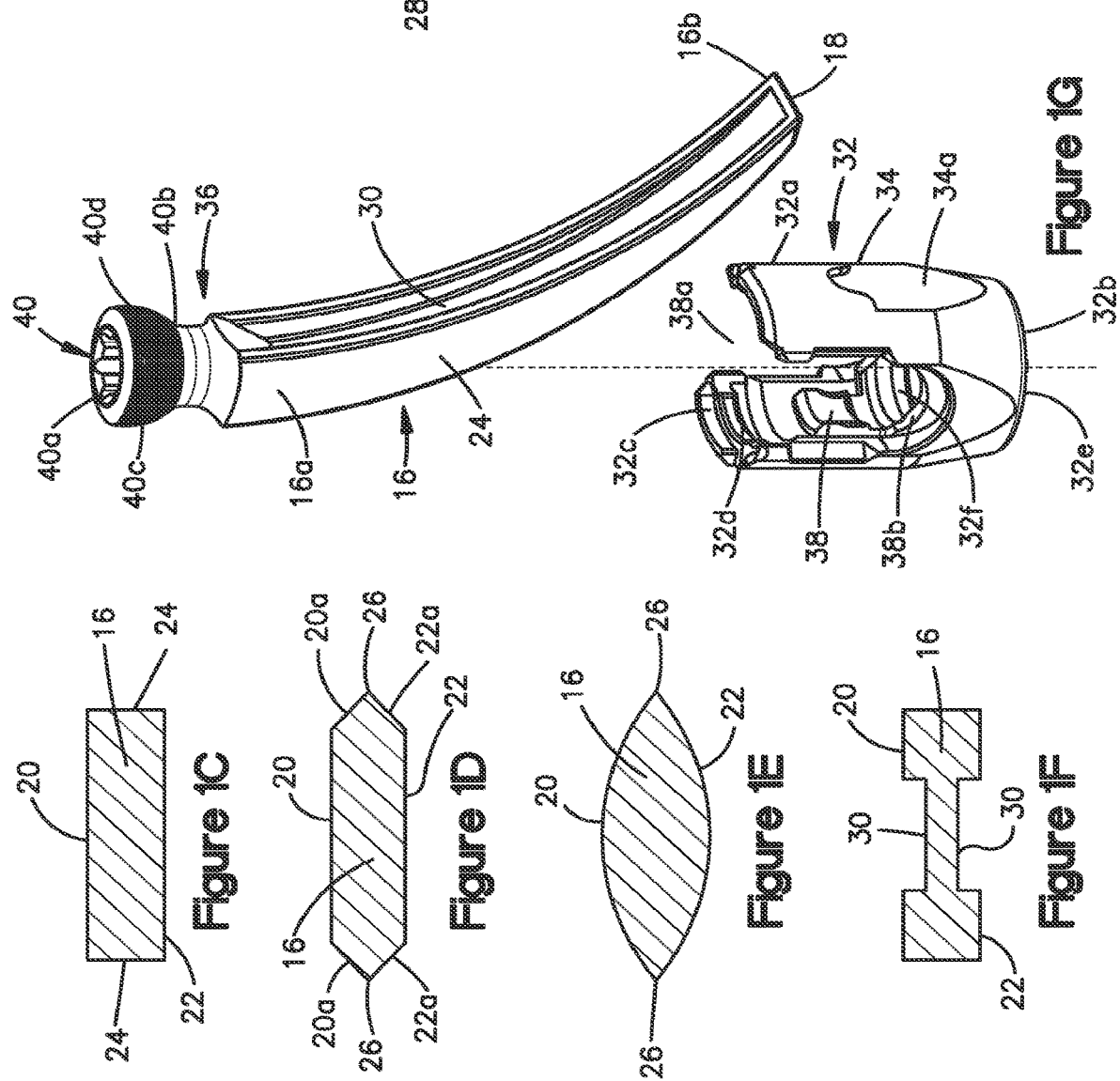

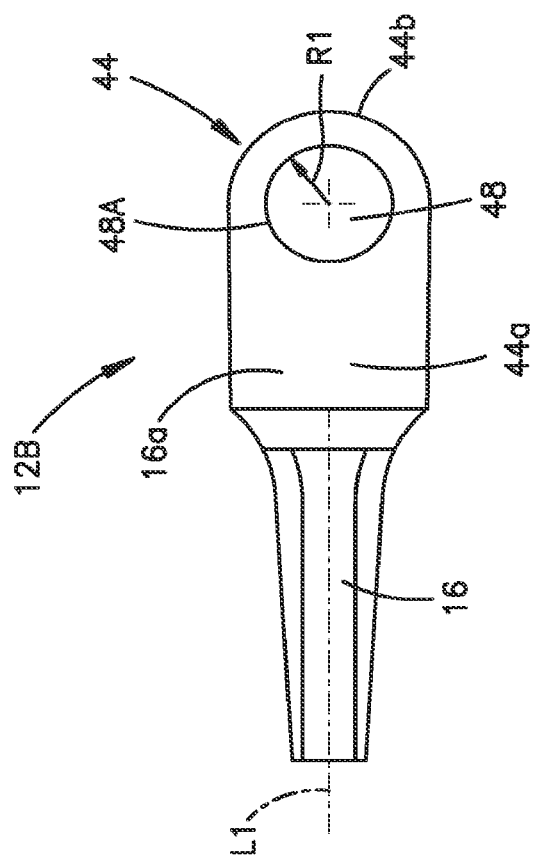
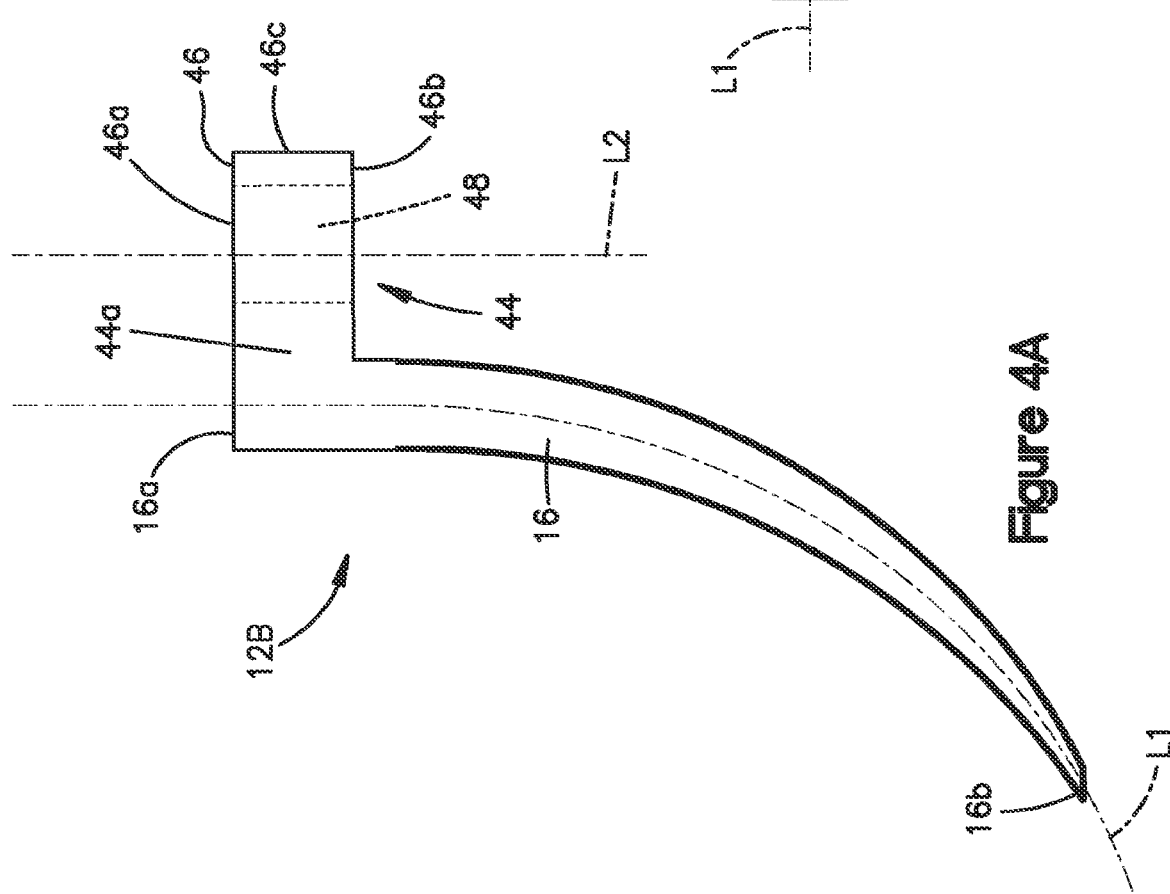

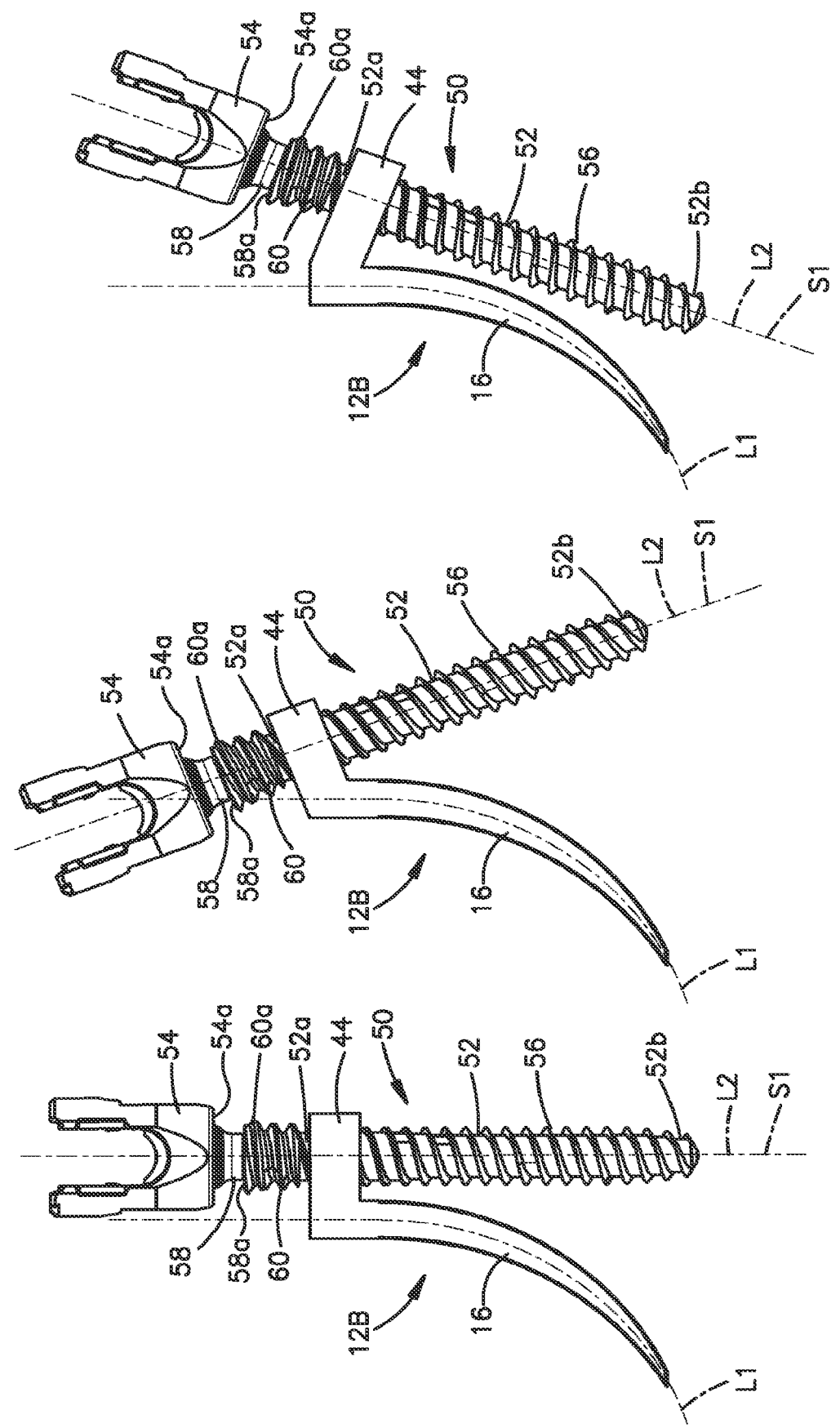

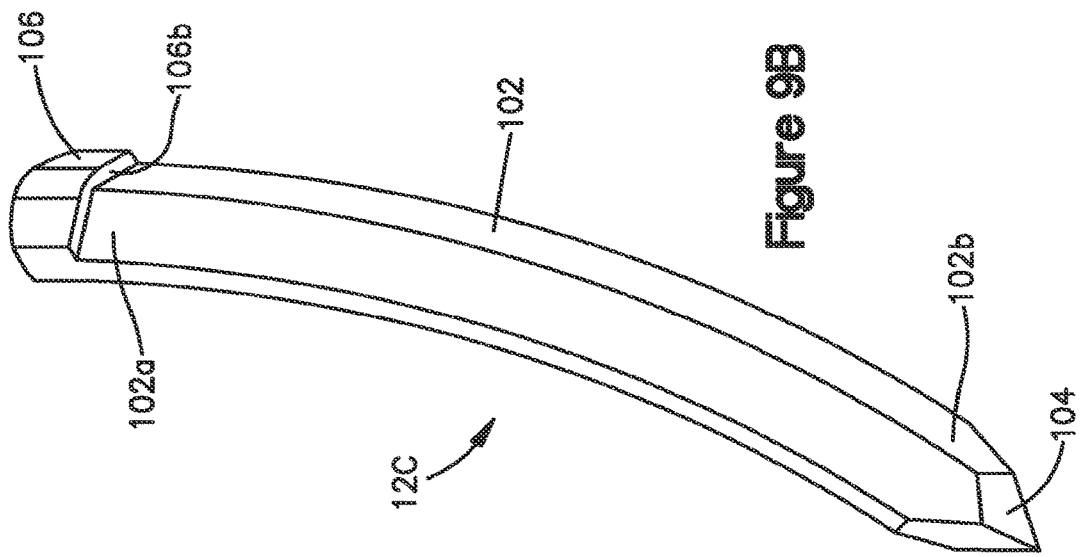
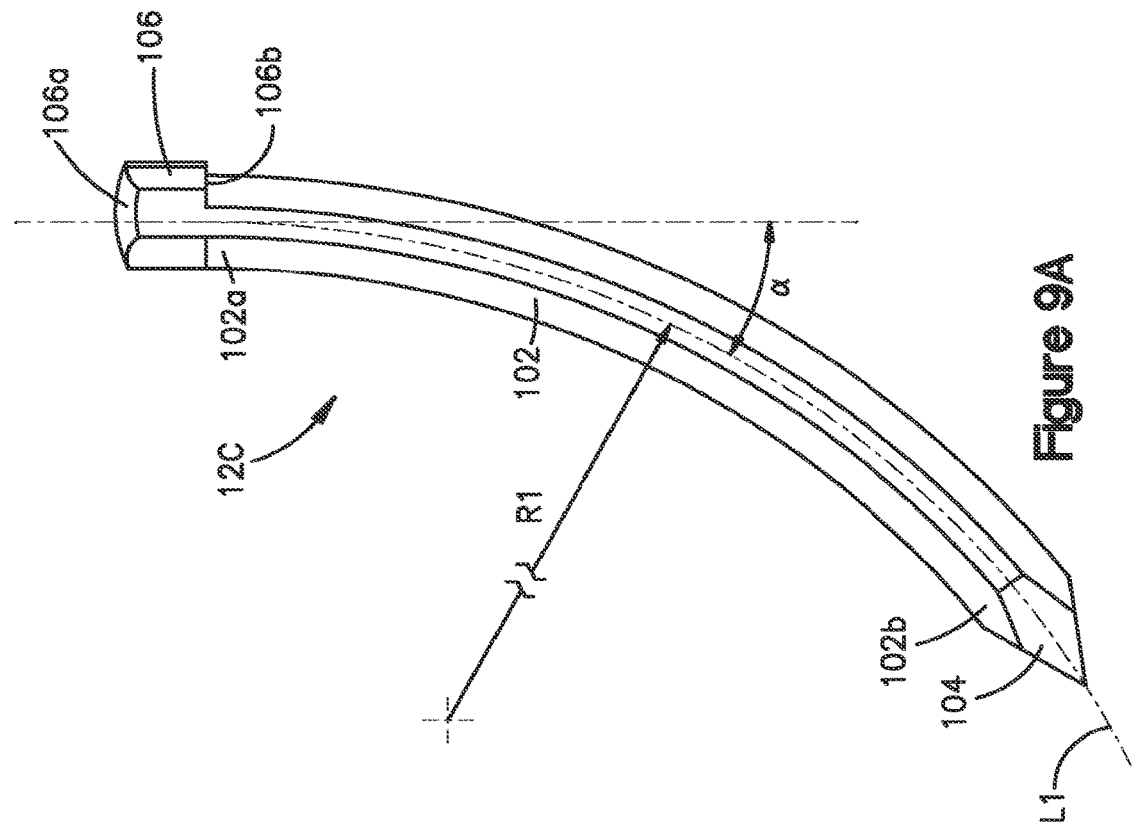

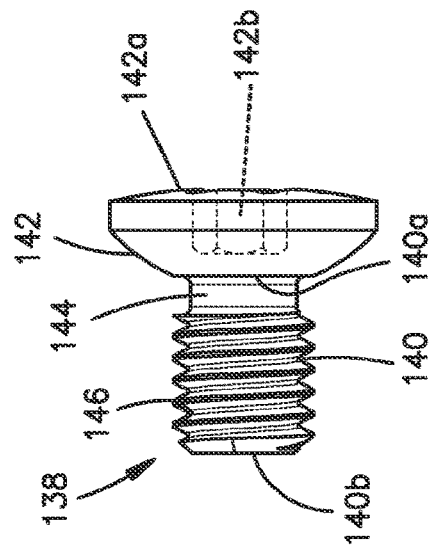
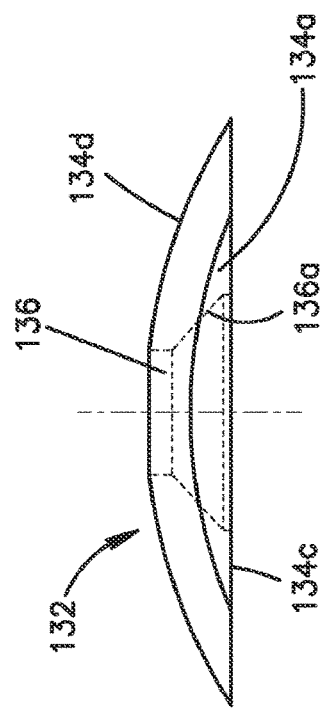
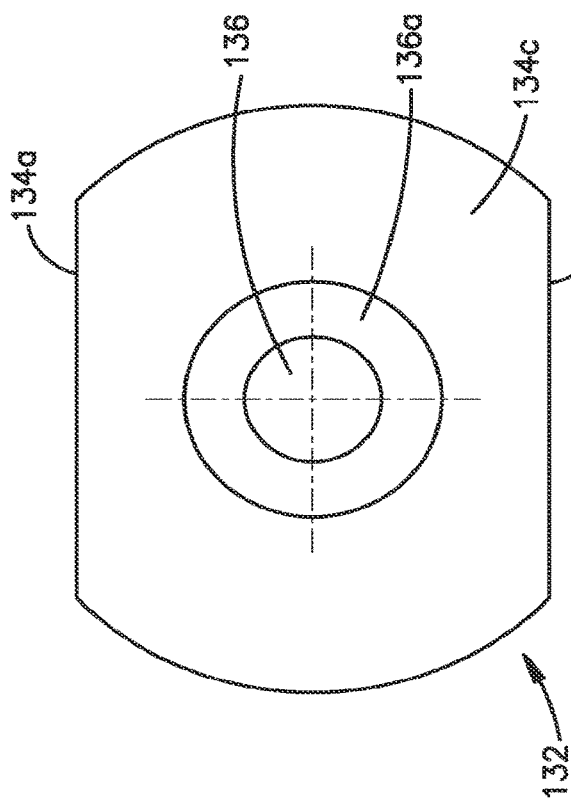

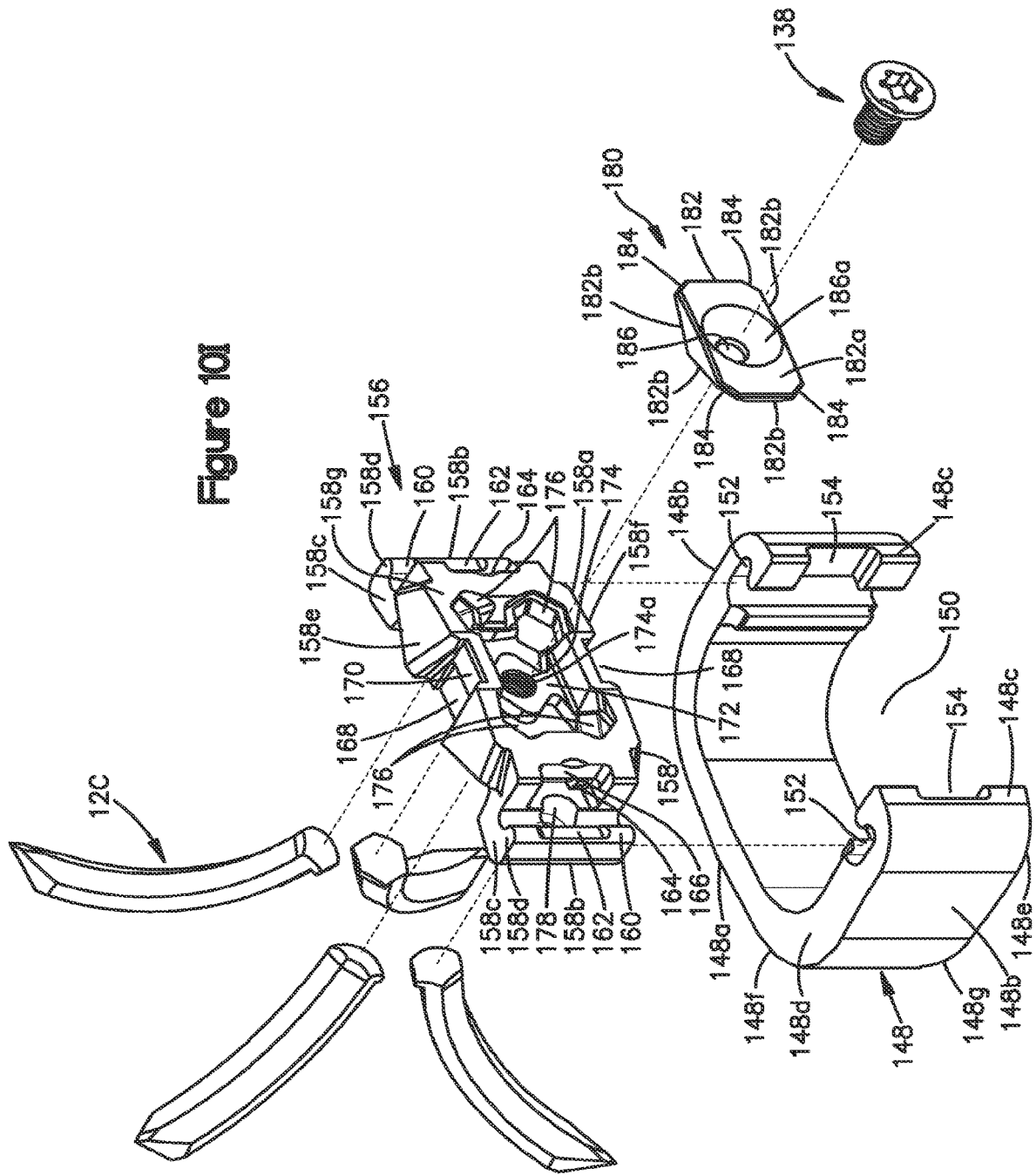

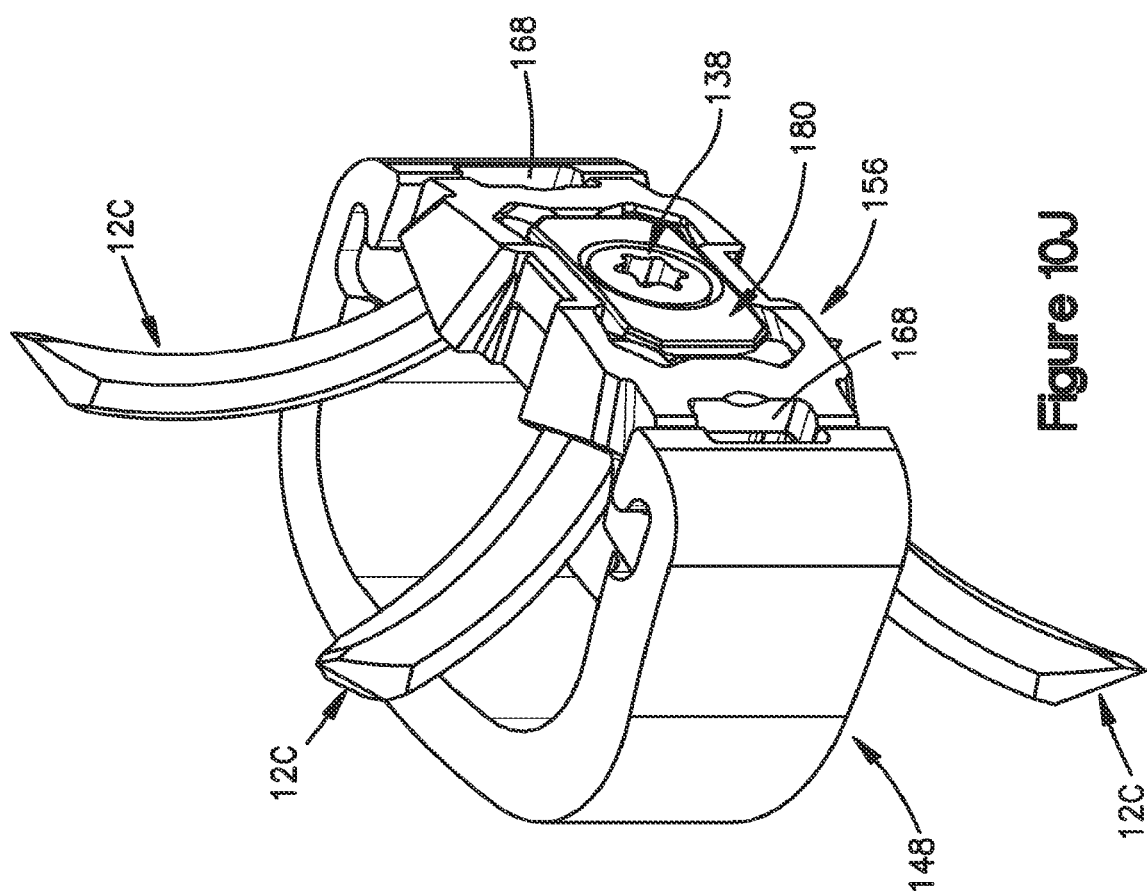

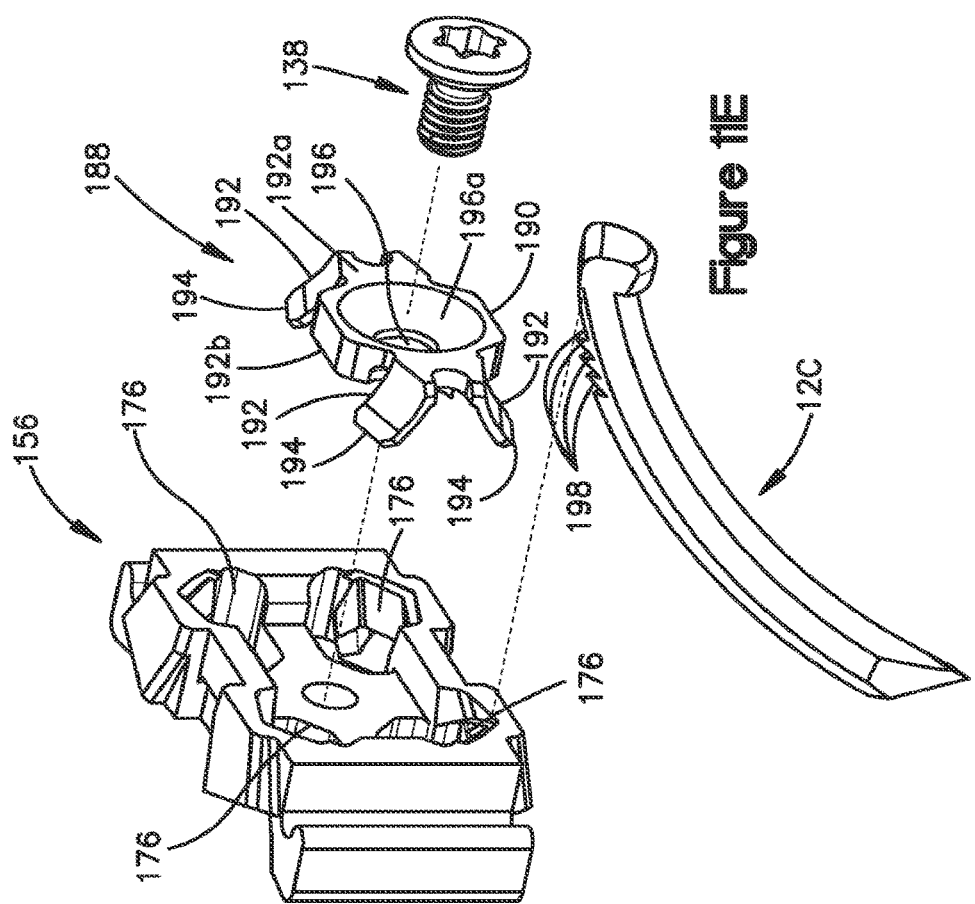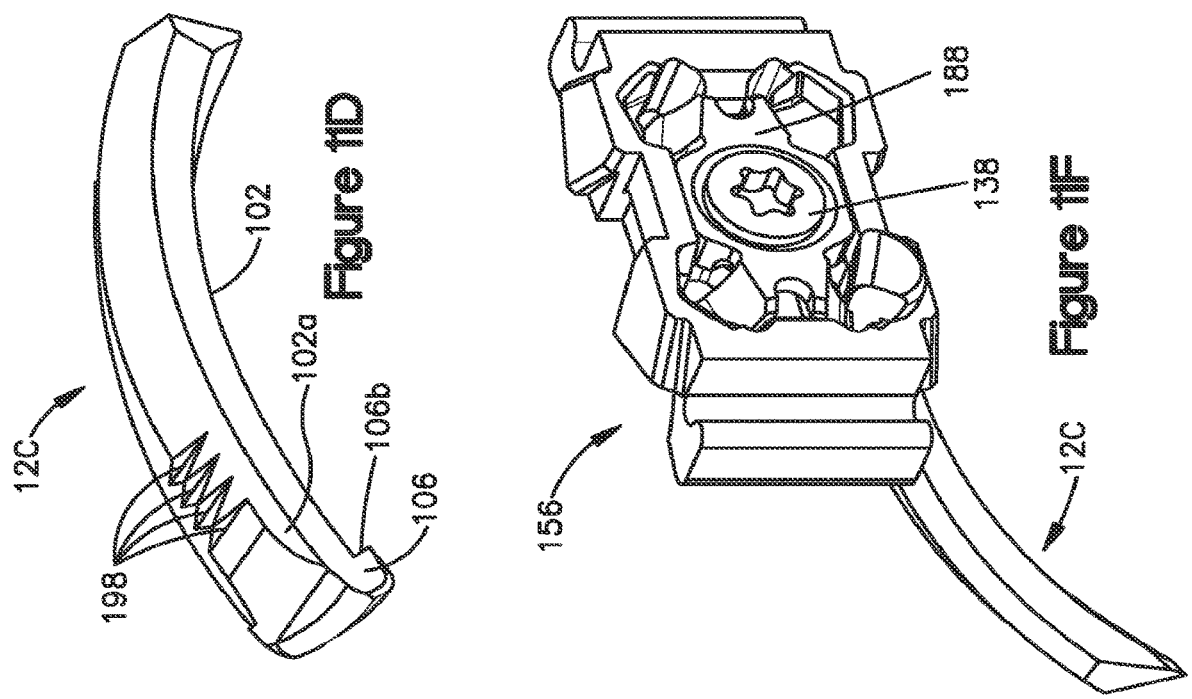

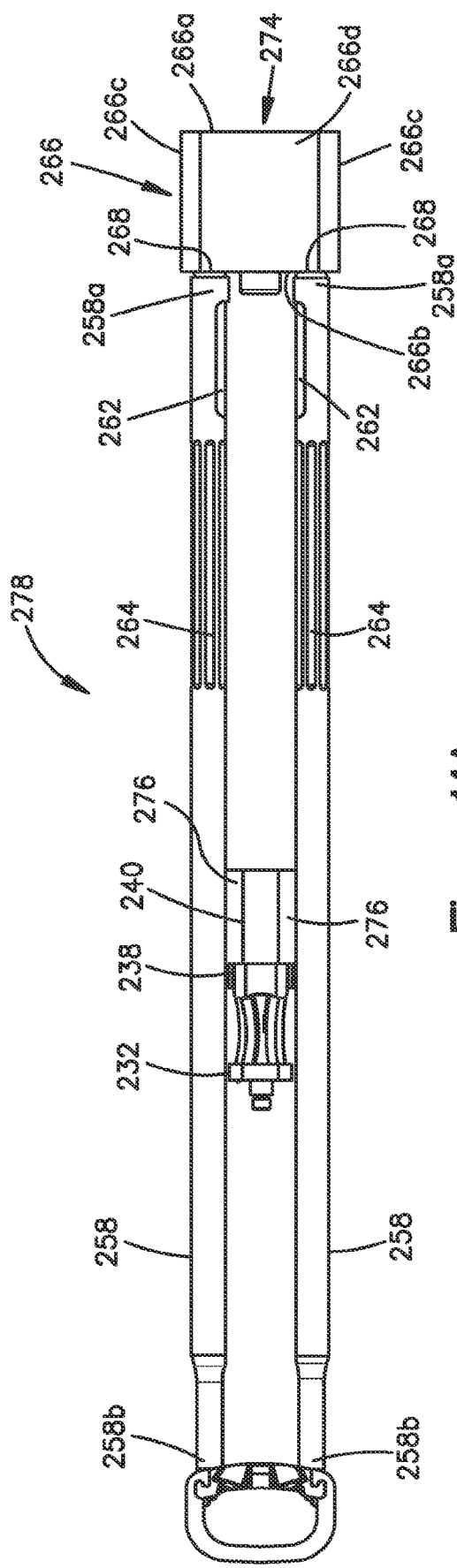

ARCUATE FIXATION MEMBER

CROSS-REFERENCE TO RELATED APPLICATIONS

This patent application is a continuation U.S. patent application Ser. No. 16/131,081, filed Sep. 14, 2018, which is a continuation of U.S. patent application Ser. No. 15/225,537, filed Aug. 1, 2016, now U.S. Pat. No. 10,105,236, issued Oct. 23, 2018, which is a continuation of U.S. patent application Ser. No. 12/761,101, filed Apr. 15, 2010, now U.S. Pat. No. 9,408,715, issued Aug. 9, 2016, which claims priority to U.S. provisional patent application No. 61/169,461, filed Apr. 15, 2009, the entire disclosure of each of which is incorporated herein by this reference.

TECHNICAL FIELD

The present disclosure relates generally to orthopedics, and in particular relates to fixation systems, intervertebral implants, and associated surgical methods and procedures for using same.

BACKGROUND

Spinal fixation systems such as pedicle screw and rod constructs are commonly used to promote fusion between intervertebral bodies. The insertion of pedicle screws typically requires a linear "line-of-approach" trajectory that is aligned with the longitudinal axis of the screw, in order to accommodate the access and delivery instruments. Similarly, anchors such as bone screws may be used to directly fix intervertebral implants to vertebral bodies, typically requiring the insertion of several screws at unique angles oblique to the sagittal and/or transverse plane, and thus multiple lines-of-approach. However, in a variety of surgical situations, achieving a desired trajectory for screw insertion can be difficult due to the patient's anatomy obstructing a linear line-of-approach. For example, medially-directed placement of pedicle screws into the sacrum is desirable to prevent screw loosening and/or pullout, but can be prohibited due to the iliac crest obstructing the linear line-of-approach.

In addition to the above-discussed linear line-of-approach problems, limitations of the fixation anchors themselves can further limit spinal fixation treatment approaches. For example, unilateral spinal fixation procedures, wherein a pedicle screw and rod construct is placed on a single side of the spine, provide advantages such as limiting surgical site morbidity and shortening surgical time when compared with standard bilateral fixation procedures wherein the construct is placed on both sides of the spine and interconnected. However, unilateral fusion constructs typically exhibit decreased mechanical rigidity in comparison to bilateral constructs, for example due to lower torsional and/or rotational rigidly and weaker resistance to screw pullout forces under physiologic loading when compared to typical bilateral constructs. As a result, unilateral fixation procedures are rarely performed in lieu of bilateral fixation procedures.

What is therefore desirable are spinal fixation systems that allow for the creation of rigid constructs when the linear line-of-approach for insertion of fixation anchors is unavailable and/or undesirable (e.g., when multiple anchors are required), while at the same time providing increased rigidity and robustness to spinal constructs such as those used in unilateral fusion procedures.

SUMMARY

Arcuate fixation members with varying configurations and/or features are disclosed, along with additional components for use therewith in disclosed fixation systems and intervertebral implant systems. The arcuate fixation members may be of varying lengths, cross sectional geometries, and/or cross sectional areas, and may be configured with various features such as heads configured to accept other fixation system components, tabs to allow arcuate fixation member-in-arcuate fixation member or fixation anchor-in-arcuate fixation member configurations. Fixation systems or intervertebral implant systems utilizing arcuate fixation members are particularly suitable when a linear line-of-approach for delivering fixation members is undesirable.

BRIEF DESCRIPTION OF THE DRAWINGS

The foregoing summary, as well as the following detailed description of the preferred embodiments of the application, will be better understood when read in conjunction with the appended drawings. For the purposes of illustrating the arcuate fixation member systems and methods, there are shown in the drawings preferred embodiments. It should be understood, however, that the instant application is not limited to the precise arrangements and/or instrumentalities illustrated in the drawings, in which:

FIG. 1A is a front elevation view of an arcuate fixation member constructed in accordance with an embodiment;

FIG. 1B is a side elevation view of the arcuate fixation member illustrated in FIG. 1A;

FIGS. 1C-1F are cross sectional views illustrating embodiments of various example geometries of the arcuate fixation member illustrated in FIGS. 1A and 1B;

FIG. 1G is a perspective view of an embodiment of an arcuate fixation member constructed in accordance with another embodiment;

FIG. 1H is a perspective view of a guiding member for receiving an arcuate fixation member;

FIG. 4A is a side elevation view of an arcuate fixation member constructed in accordance with another embodiment;

FIG. 4B is a top elevation view of the arcuate fixation member illustrated in FIG. 4A;

FIG. 4C is a side elevation view of an embodiment of the arcuate fixation member illustrated in FIG. 4A in combination with a fixation anchor;

FIGS. 4D and 4E are side elevation views of additional embodiments of the arcuate fixation member and fixation anchor illustrated in FIG. 4C;

FIG. 9A is a side elevation view of an arcuate fixation member constructed in accordance with another embodiment;

FIG. 9B is a perspective view of the arcuate fixation member illustrated in FIG. 9A;

FIG. 9H is a front elevation view of a blocking plate for use with the fixation plate illustrated in FIGS. 9F and 9G;

FIG. 9I is a top elevation view of the blocking plate illustrated in FIG. 9H;

FIG. 9J is a side elevation view of a locking screw for use with the fixation plate illustrated in FIGS. 9F and 9G;

FIG. 10I is an exploded view of an assembly utilizing the components illustrated in FIGS. 10A to 10H;

FIG. 10J is a perspective view of an assembly utilizing the components illustrated in FIGS. 10A to 10H;

FIG. 11D is a perspective view of an arcuate fixation member constructed in accordance with another embodiment;

FIG. 11E is an exploded view of an assembly utilizing the components illustrated in FIGS. 9J, 10E, 10F, and 11A to 11D;

FIG. 11F is a perspective view of the assembly illustrated in FIG. 11E;

FIG. 14A is a top elevation view of assembled components of another embodiment of a delivery instrument;

FIG. 14B is a perspective view of a component illustrated in FIG. 14A;

DETAILED DESCRIPTION OF ILLUSTRATIVE EMBODIMENTS

Figure 2:
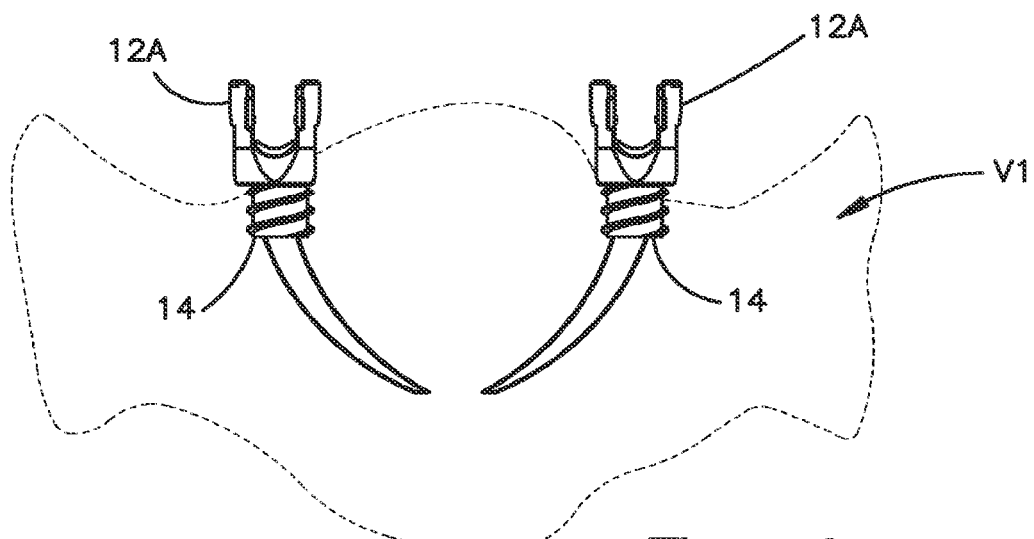
FIG. 2 is a cranial-caudal view of a vertebral body with a pair of arcuate fixation members and guiding members inserted therein.

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior", "lateral", "medial", "sagittal", "axial", "coronal," "cranial," "caudal" and related words and/or phrases designate preferred positions and orientations in the human body to which reference is made and are not meant to be limiting.

The words "arcuate" and "curved" as used herein refer generally to the varying physical geometry of an object along an axis coincident to the object, for example the deviation from straightness of the body of an arcuate fixation member along a central longitudinal axis defined with the body of the object between its proximal and distal ends. Generally, with reference to a straight axis projected from a first end of such an object, as distance from the first end of the object increases along the central longitudinal axis of the object, distance between the central longitudinal axis of the object and the straight axis increases more or less continuously, so that the body of the object defined along its central longitudinal axis takes on a curved or arcuate shape. The resulting curvature of the central longitudinal axis may exhibit a constant or uniform radius with respect to a point in space defined remotely from the body of the object. Alternatively, a non-uniform or varying radius of curvature may be defined. The curvature of the body of the object defined by the longitudinal axis may also vary in direction with respect to a Cartesian coordinate system. The curvature may be uniformly distributed along the body of the object, for example between the proximal and distal ends of the object, or may be localized within one or more distinct segments of the body of the object. The curvature of the object may be significantly smooth and continuous along its central longitudinal axis, may be defined by a series of straight interconnected segments where each successive segment defines an increasing angle between the central longitudinal axis of the body of the object and the straight axis, or any combination thereof.

The words "vertebral body" as used herein should be interpreted broadly to include all the bones and bony structures found within and in the immediate proximity of the human spinal system, including but not limited to those found in the cervical region, the thoracic region, the lumbar region, and the sacral curve region.

The terminology intended to be non-limiting includes the above-listed words, derivatives thereof and words of similar import.

Described herein are arcuate fixation members with varying configurations and/or features, along with additional components for use therewith in fixation systems and intervertebral implant systems. Applications of fixation systems and/or intervertebral implants systems utilizing arcuate fixation members could include, but are not limited to, fixation of the endplate components of a total disc replacement to vertebral bodies, lateral mass fixation in the cervical spine, direct fixation of an intervertebral implant to vertebral bodies, fixation into osteoporotic bone, anchor-in-anchor fixation into underlying bone, securing auxiliary fixation devices to underlying bone, and the like. The use of systems and/or methods utilizing arcuate fixation members disclosed herein are particularly suitable when a linear line-of-approach for delivering fixation member is undesirable. It should be noted that the physical characteristics of the arcuate fixation members disclosed herein may cause them to be alternately described as arcuate blades, arcuate pins, arcuate nails, or other terms of similar descriptive import.

With initial reference to FIGS. 1A to 1H, an example embodiment of a fixation system 10 comprising an arcuate fixation member 12A and a guiding member 14 is illustrated. As will become appreciated from the description below, one or more arcuate fixation members 12A may be utilized, alone or in combination with one or more guiding members 14, to securely fasten auxiliary fixation devices, for example fixation rods, to an underlying bone, such as a vertebral body. Unless otherwise indicated, the bone fixation system 10 and its components can be manufactured from any suitable biocompatible material known in the art including but not limited to titanium, titanium alloy such as TAN, stainless steel, reinforced plastics, allograft bone, and the like.

FIGS. 1A and 1B illustrate front and side views of the arcuate fixation member 12A respectively. The arcuate fixation member 12A includes a body 16 defining a proximal end 16a and a distal end 16b opposite the proximal end. The distal end 16b may comprise a tip 18 configured to cut into underlying structure or bone. The body 16 may further define an intermediate portion between the proximal end 16a and the distal end 16b that is curved along a central curved axis L1. In an embodiment, the intermediate portion is curved along substantially the entire length of the body between the proximal end 16a and the distal end 16b, as depicted in FIG. 1B. Alternatively, one or more distinct portions of the intermediate portion between the proximal end 16a and the distal end 16b may be curved (not shown). It should be appreciated that while the various embodiments of arcuate fixation members described and illustrated in the instant disclosure feature a uniform direction of curvature with respect to the central curved axis L1, arcuate fixation members in which the direction of curvature reverses and/or otherwise deviates within the intermediate portion are contemplated and meant to be included within the scope of the instant disclosure.

In an embodiment, the intermediate portion is curved along the central curved axis L1 in accordance with a uniform radius of curvature R1. Alternatively, the intermediate portion may define a non-uniform radius of curvature along the central curved axis L1. In a preferred embodiment, the curvature of the intermediate portion may be smooth and continuous. Alternatively, the curvature of the intermediate portion may be defined by a series of substantially straight sections (not shown), with each substantially straight section aligned along an individual longitudinal axis corresponding to the individual section, where the magnitude of an angle α with respect to a perpendicular reference axis extended from the proximal end 16a increases in magnitude with the distance of each subsequent straight section from the proximal end 16a.

The body 16 of the arcuate fixation member 12A may define a variety of cross sectional geometries. In an embodiment, the body 16 may define a substantially rectangular cross section, defined by an inner surface 20, an outer surface 22 substantially parallel with and opposite to the inner surface 20, and lateral surfaces 24 on opposite sides of the body 16, as depicted in FIG. 1C. The lateral surfaces 24 may be substantially perpendicular to the inner and outer surfaces 20 and 22 respectively. In another embodiment, the body 16 may define a substantially hexagonal cross section defined by an inner surface 20, an outer surface 22 substantially parallel with and opposite to the inner surface 20, inner chamfered surfaces 20a, and outer chamfered surfaces 22a, as illustrated in FIG. 1D. The inner and outer chamfered surfaces 20a and 22a respectively may converge to form lateral edges 26 on opposite sides of the body 16. The lateral edges 26 may be configured to cut into underlying structure or bone. In yet another embodiment, the body 16 may define a substantially elliptical cross section, defined by inner and outer surfaces 20 and 22 respectively, as illustrated in FIG. 1E. The inner and outer surfaces 20 and 22 respectively may converge to form lateral edges 26 on opposite sides of the body 16. The lateral edges 26 may be configured to cut into underlying structure or bone. In yet another embodiment, the body 16 may define a round or elliptical cross section with a continuous outer surface lacking any edges (not shown). It should be noted that the above-discussed cross sectional geometries of the body 16 are merely examples, and the scope of the instant disclosure should not be limited thereto.

In an embodiment, the cross sectional area of the body 16 may remain uniform between the proximal end 16*a* and the distal end 16*b*. In another embodiment, the cross sectional area of the body 16 may diminish along the central curved axis L1 with increasing distance extending from the proximal end 16*a* (i.e., the body 16 may define a tapered geometry between the proximal 16*a* and the distal end 16*b*) toward the distal end 16*b*, resulting in a cross sectional area of the body 16 at the distal end 16*b* that is of a smaller magnitude than the cross sectional area of the body at the proximal end 16*a*. In an embodiment, the cross sectional area of the body 16 in the area of the distal end 16*b* may be configured to form the tip 18 at the distal end 16*b*. For example, the tip 18 may be formed where the inner surface 20 and the outer surface 22 converge at the distal end 16*b*, such that a tip with a square geometry is formed along a surface substantially perpendicular to the lateral surfaces 24. In another embodiment, a pointed tip (not shown) may be formed at the distal end 16*b*, by defining a plurality of tip surfaces that form acute angles with the central curved axis L1 at the proximal end 16*b*. It should be noted that these tip geometries are merely examples, and the scope of the instant disclosure should not be limited thereto.

The arcuate fixation member 12A may be configured to slidably engage with a curved guiding bore 28 defined in the guiding member 14. In an embodiment, a groove 30 may be defined within a portion of the body 16 between the proximal end 16*a* and the distal end 16*b*. For example, the groove 30 may be formed on the inner surface 20 and/or the outer surface 22. Groove to engage guiding member. The groove 30 may be formed with a constant width and/or depth. Alternatively, the width and/or depth of the groove may diminish with distance extending from the proximal end 16*a* towards the distal end 16*b*, to introduce a frictional engagement force as the arcuate fixation member 12A is inserted into the curved guiding bore 28 of the guiding member 14. The groove 30 may be formed in the body 16 using any geometry appropriate for achieving slidable engagement with the complimentary curved guiding bore 28. For example, FIG. 1F illustrates a cross sectional view of the body 16 with rectangular grooves 30 formed in the inner and outer surfaces 20 and 22 respectively, configured to slidably engage with the "I" shaped curved guiding bore 28 defined in the guiding member 14. It should be noted that this rectangular groove geometry is only an example, and the scope of the instant disclosure should not be limited thereto.

The arcuate fixation member 12A may have a head 32 defined at the proximal end 16*a* of the body 16. The head 32 may include a cylindrical body 34, or may include any other body geometry as appropriate. The head 32 may define a proximal end 32*a* and a distal end 32*b*. The distal end 32*b* of the head 32 may be coupled to the proximal end 16*a* of the body 16, either directly or indirectly via a neck 36 that is coupled between the proximal end 16*a* of the body 16 and the distal end 32*b* of the head 32. The cylindrical body 34 may have external surfaces 34*a* formed within opposing sides of the cylindrical body 34. The external surfaces 34*a* may be formed along vertical planes formed within the cylindrical body 34, the vertical planes being parallel with the central curved axis L1. The external surfaces 34*a* may be further configured to be engaged by complimentary features of a delivery instrument.

The cylindrical body 34 may have a slot 38 formed therein along an axis perpendicular to the central curved axis L1, the slot 38 defined by an open end 38*a* and extending from the proximal end 32*a* of the head 32, downward into the cylindrical body 34, the slot terminating a seat end 38*b*. The seat end 38*b* of the slot 38 may be configured to nestably receive a component of a fixation system, for example a fixation rod (not shown) and the like. The slot 38 may further define two end cap surfaces 32*c* within the head 32 in the area of the proximal end 32*a*, on opposing sides of the slot 38. The end cap surfaces 32*c* may be configured with engaging features 32*d* for lockably engaging an end cap (not shown), for example a pedicle screw end cap, or the like. The engaging features may comprise a series of threads or any other features appropriate for lockably engaging an end cap.

In an example embodiment, the above-described components of the arcuate fixation member 12A, including the body 16, the head 32, and the neck 36, may all be coupled together in a rigid assembled configuration prior to insertion. In another example embodiment, the arcuate fixation member 12A may comprise separate components that are assembled in a non-rigid configuration prior to insertion. For example, in the embodiment illustrated in FIG. 1G, the body 16 of the arcuate fixation member 12A is coupled to the neck 36 at the proximal end 16*a* of the body 16. A toggle head 40 may be coupled to the upper end of the neck 36, opposite the end where the neck 36 is coupled to the body 16. The toggle head 40 includes an annular body that defines a proximal, or upper, end 40*a*, a distal, or lower, end 40*b*, and a radially outer surface 40*c*. The annular body of the toggle head 40 can define the shape of a segment of a sphere as illustrated, having a diameter or cross-sectional dimension that is greater at a location between the proximal and distal ends 40*a* and 40*b* than at either of the proximal and distal ends 40*a* and 40*b*. Accordingly, the radially outer surface 40*c* can be spherical or otherwise convex. Of course, the toggle head 40 can assume any other suitable alternative shape as desired. A series of annular rings 40*d* may be defined within the radially outer surface 40*c* between the proximal and distal ends 40*a* and 40*b*. The annular rings 40*d* may be configured to engage a complementary inner annular ring 32*f* formed in the area of an aperture 32*e* defined within the distal end 32*b* of the head 32. The geometry of the aperture 32*e* may be configured to allow the body 16 and neck 36 of the arcuate fixation member 12A to be inserted into the head 32 and through the distal end 32*b* of the head 32, such that the outer surface 40*c* of the toggle head 40 becomes seated within the aperture 32*e* in an assembled configuration. In an assembled configuration, the head 32 may rotate and/or translate about the toggle head 40 prior to final tightening of the assembled configuration, providing additional freedom of alignment, for example when the arcuate fixation member 12A is used in spinal fixation constructs. When the assembled configuration undergoes final tightening, one or more of the annular rings 40*d* of the outer surface 40*c* of the toggle head 40 may lockably engage with the inner annular ring 32*f* of the head 32, thereby locking the head 32 into position with respect to the toggle head 40.

Now referring to FIG. 1H, the guiding member 14 may include a cylindrical body 42, or may include any other body geometry as appropriate. The guiding member 14 may define a proximal end 14*a*, a distal end 14*b*, and an outer surface 14*c* having threads defined thereon. The threads defined on the outer surface 14*c* may be configured to cut into underlying structure or bone. A curved guiding bore 28 may be formed through the body 42 between the proximal end 14*a* and the distal end 14*b*. The geometry of the curved guiding bore 28 may be configured in such a way as to slidably engage with a complimentary cross sectional geometry of the body 16 of the arcuate fixation member 12A. The curved guiding bore 28 may be defined by a constant cross sectional geometry between the proximal end 14a and the distal end 14b. Alternatively, the cross sectional geometry of the curved guiding bore 28 may diminish in magnitude with distance extending from the proximal end 14a downward in the direction of the distal end 14b, to introduce a frictional engagement force as the arcuate fixation member 12A is received within the curved guiding bore 28. The curved guiding bore 28 is depicted with an "I" shaped geometry in FIG. 1H, but this curved guiding bore geometry is only an example, and the scope of the instant disclosure should not be limited thereto.

Figure 3:
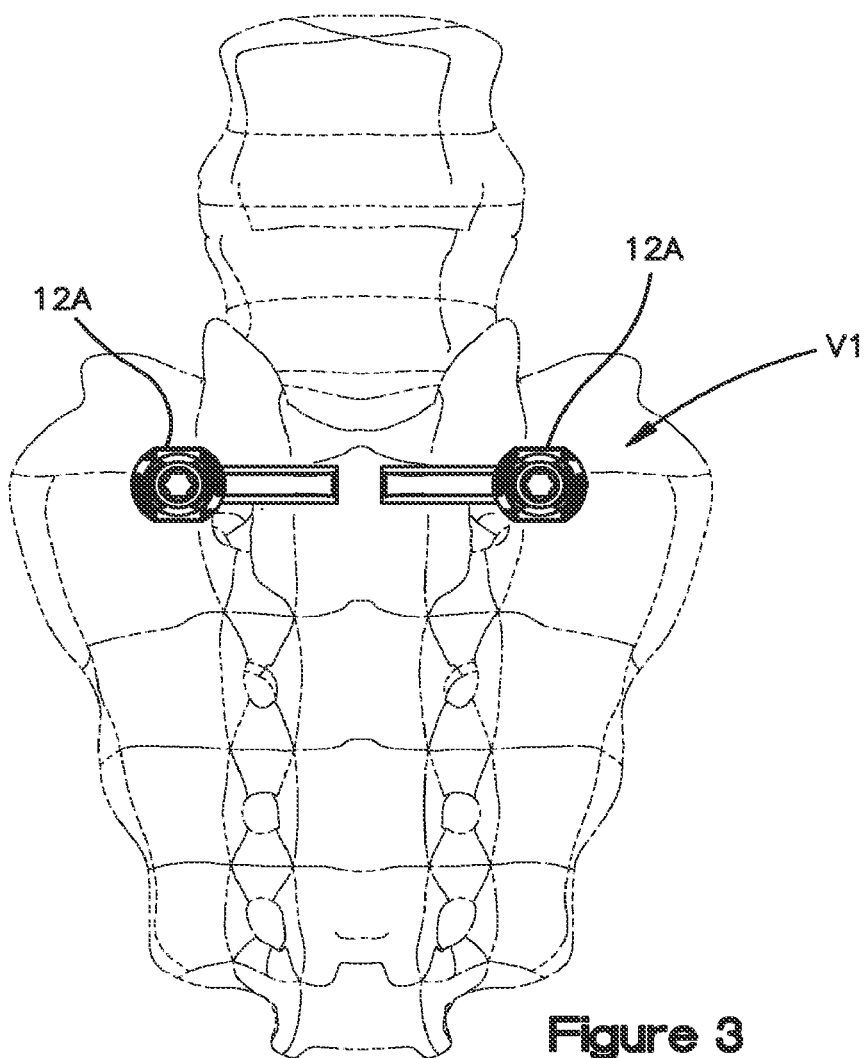
FIG. 3 is a posterior view of the assembly illustrated in FIG. 2.

Now referring to FIGS. 2 and 3, the fixation system 10 is illustrated with a pair of the arcuate fixation members 12A and the guiding members 14 in an example embodiment of an assembled configuration within a vertebral body V1. In one method of assembling the fixation system 10, a guiding member 14 is driven into the vertebral body V1 so that the threads of the outer surface 14c engage the bone of the vertebral body V1. A guide hole with a diameter of lesser magnitude than the outer diameter of the helical threads of the guiding member 14 may be bored in the vertebral body V1 before the guiding member 14 is driven into the vertebral body. The guiding member 14 may be driven into the vertebral body to a sufficient depth so that the surface of the proximal end 14a of the guiding member is substantially flush with the outer surface of the vertebral body V1. Once the guiding member 14 is sufficiently anchored within the vertebral body V1, an arcuate fixation member 12A may be slid into the curved guiding bore 28 of the guiding member 14 in preparation for driving the arcuate fixation member 12A into the bone of the vertebral body V1. Once inserted into driving position within the guiding member 14, the arcuate fixation member 12A may be driven into the bone of the vertebral body V1 via a biasing force. In an embodiment, biasing force may be applied by a delivery instrument as described in greater detail below. The assembled pair of the arcuate fixation members 12A and the guiding members 14, as illustrated in FIGS. 2 and 3, may comprise the first tier of a bilateral spinal fixation construct. It should be noted that utilization of the fixation system 10 in a sacrum (i.e., the vertebral body V1) as illustrated in FIGS. 2 and 3 is merely an example, and that the fixation system 10 may be utilized in any other type of vertebral body, or other bony structure, as appropriate. It should further be noted that while the fixation system 10 has been described thus far to include both the arcuate fixation member 12A and the guiding member 14 to guide the arcuate fixation member 12A as it inserted into bone, alternative embodiments of constructing the fixation system 10 may omit the use of the guiding member 14, whereby the guiding function performed by the guiding member 14 may be performed by a delivery instrument.

Now referring to FIGS. 4A to 4E, in another example embodiment of the spinal fixation system 10, an arcuate fixation member 12B is illustrated. It should be noted preliminarily that in the interest of brevity, the figures and subsequent description pertaining to the arcuate fixation member 12B do not refer to certain features of the arcuate fixation member 12A that may be integrated into the arcuate fixation member 12B, for example the groove 30 within the body 16, or the use of the arcuate fixation member 12A in combination with the guiding member 14 in an assembled configuration. However, embodiments in which those and other features of the arcuate fixation member 12A are integrated into the arcuate fixation member 12B are intended to be within the scope of the instant disclosure.

The arcuate fixation member 12B may have a lateral tab 44 defined at the proximal end 16a of the body 16, the lateral tab defining a proximal end 44a and a distal end 44b opposite the proximal end. The lateral tab 44 includes a tab body 46 that is coupled to the body 16 of the arcuate fixation member 12B at the proximal end 44a and extends outwardly from the body 16 toward the distal end 44b. The tab body 46 may be defined by an upper surface 46a, a lower surface 46b, and a lateral surface 46c defined between the upper and lower surfaces 46a 46b and extending around the tab body 46. The tab body 46 may be formed so that the upper and lower surfaces 46a and 46b are substantially coplanar with a plane defined perpendicular to the central curved axis L1 at the proximal end 16a of the body 16. Alternatively, tab body 46 may be formed so that the upper and lower surfaces 46a and 46b define planes that form at least one acute angle with respect to a plane defined perpendicular to the central curved axis L1 at the proximal end 16a of the body 16. Forming the tab body 46 at varying angles with respect to a plane defined perpendicular to the central curved axis L1 at the proximal end 16a of the body 16 allows the geometry of the tab body 46 with respect to the body 16 to be conformed to varying patient anatomies. Example embodiments with angled tab bodies 46 are illustrated in FIGS. 4D and 4E. The lower surface 46b of the tab body 46 may have gripping features defined therein configured to grip bone, for example serrated teeth (not shown) or the like. Such gripping features may provide stability against rotational forces when the arcuate fixation member is inserted into bone in an assembled configuration.

The tab body 46 may have an aperture 48 formed therethrough. In an example embodiment, the aperture 48 may define a through hole with a radius R1 extending from a longitudinal axis L2. An inner surface 48a of the aperture 48 may be threaded to receive complimentary threads of a fixation anchor 50, for example a pedicle screw, or the like. The fixation anchor 50 includes a shaft 52 that extends longitudinally along a longitudinal shaft axis S1. The shaft 52 defines longitudinally opposing proximal, or upper, and distal, or lower, ends 52a and 52b, respectively, and a head 54 coupled to the proximal end 52a. It should be noted that the head 54 of fixation anchor 50 may be configured with similar features to those described above with respect to head 32 of the arcuate fixation member 12B. Helical threads 56 extend radially out from the shaft 52 at locations at and between the proximal and distal ends 52a and 52b that are configured to engage underlying structure or bone. Thus, a substantial entirety of the shaft 52 between the proximal and distal ends 52a and 52b may be threaded. A distal end 54a of the head 54 is coupled to the proximal end 52a of the shaft 56, either directly or indirectly via an unthreaded neck 58 that is coupled between the proximal end 52a of the shaft 52 and the distal end 54a of the head 54.

A portion 60 of the shaft 52 between a distal end 58a of the neck 58 and the proximal end 52a of the shaft 52 may have engagement features defined thereon configured to lockingly engage with complimentary engagement features formed within the inner surface 48a of the aperture 48. For example, helical locking threads 60a may extend radially out from the portion 60 of the shaft 52 at locations at and between the distal end 58a of the neck 58 and the proximal end 52a of the shaft 52 that are configured to engage the complimentary threads formed within the inner surface 48a of the aperture 48. In an example embodiment, the helical locking threads 60a may define an outer diameter that decreases in a direction from the distal end 58a of the neck 58 toward the proximal end 52a of the shaft 52. Accordingly, the helical locking threads 60a disposed at the distal end 58a of the neck 58 may define an outer diameter that is greater than the outer diameter of the helical locking threads 60a disposed at the proximal end 52a of the shaft 52, as illustrated in FIG. 4C. Alternatively, the outer diameter of the helical locking threads 60a may remain constant between the distal end 58a of the neck 58 toward the proximal end 52a of the shaft 52.

Figure 4G:
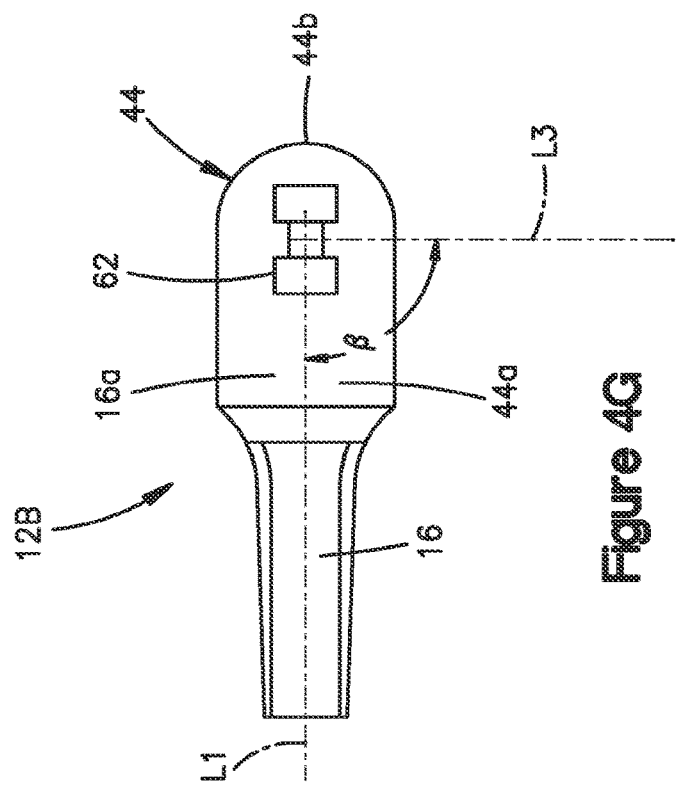
FIG. 4G is a top elevation view of the arcuate fixation member illustrated in FIG. 4F, without the arcuate fixation member illustrated in FIGS. 1A and 1B.
Figure 4F:
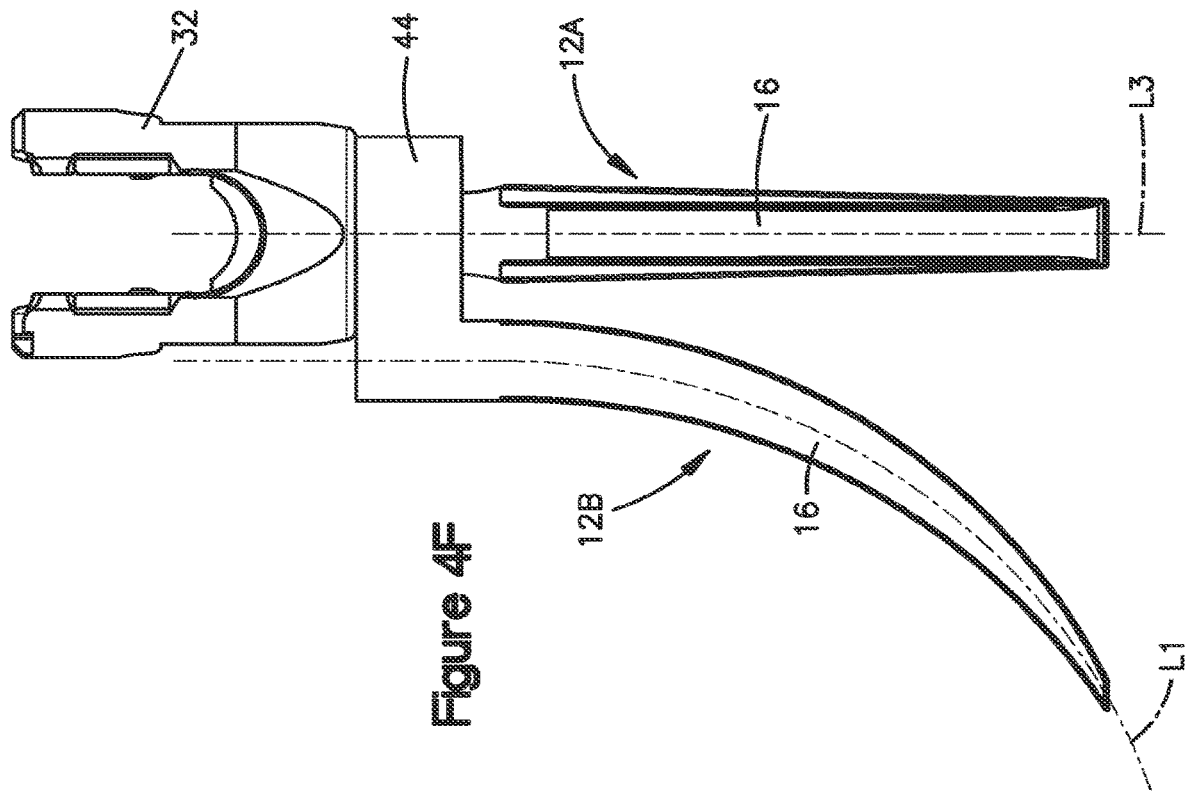
FIG. 4F is a side elevation view of an embodiment of the arcuate fixation member illustrated in FIG. 4A in combination with an embodiment of the arcuate fixation member illustrated in FIGS. 1A and 1B.

Now referring to FIGS. 4F and 4G, in another example embodiment of the spinal fixation system 10, the tab body 46 of the arcuate fixation member 12B may have a curved guiding bore 62 formed therethrough along a central curved axis L3 that forms an angle β with the central curved axis L1. The geometry of the curved guiding bore 62 may be configured in such a way as to slidably engage with a complimentary cross sectional geometry of the body 16 of the arcuate fixation member 12A. By varying the angle β between the central curved axes L1 and L3, and thus rotating the configuration of the curved guiding bore 62 within the tab body 46 about the central curved axis L3, it is possible to conform how the bodies 16 of the arcuate fixation members 12A and 12B will be positioned in an assembled configuration (e.g., as illustrated in FIG. 4F) for varying patient anatomies. The curved guiding bore 62 may be defined by a constant cross sectional geometry between the upper and lower surfaces 46a and 46b of the tab body 46. Alternatively, the cross sectional geometry of the curved guiding bore 62 may diminish in magnitude with distance extending from the upper surface 46a downward in the direction of the lower surface 46b, to introduce a frictional engagement force as the arcuate fixation member 12A is received within the curved guiding bore 62. The curved guiding bore 62 is depicted with an "I" shaped geometry in FIG. 4G, but this curved guiding bore geometry is only an example, and the scope of the instant disclosure should not be limited thereto.

Figure 5:
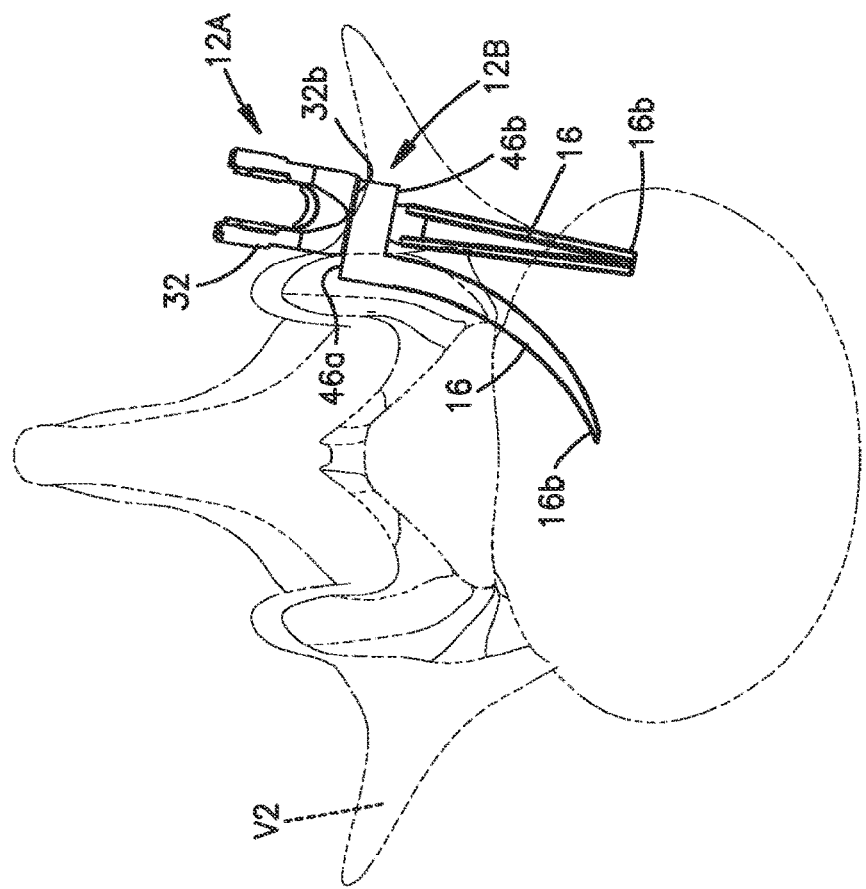
FIG. 5 is a cranial-caudal view of a vertebral body with the arcuate fixation member illustrated in FIG. 4C inserted therein.
Figure 6:
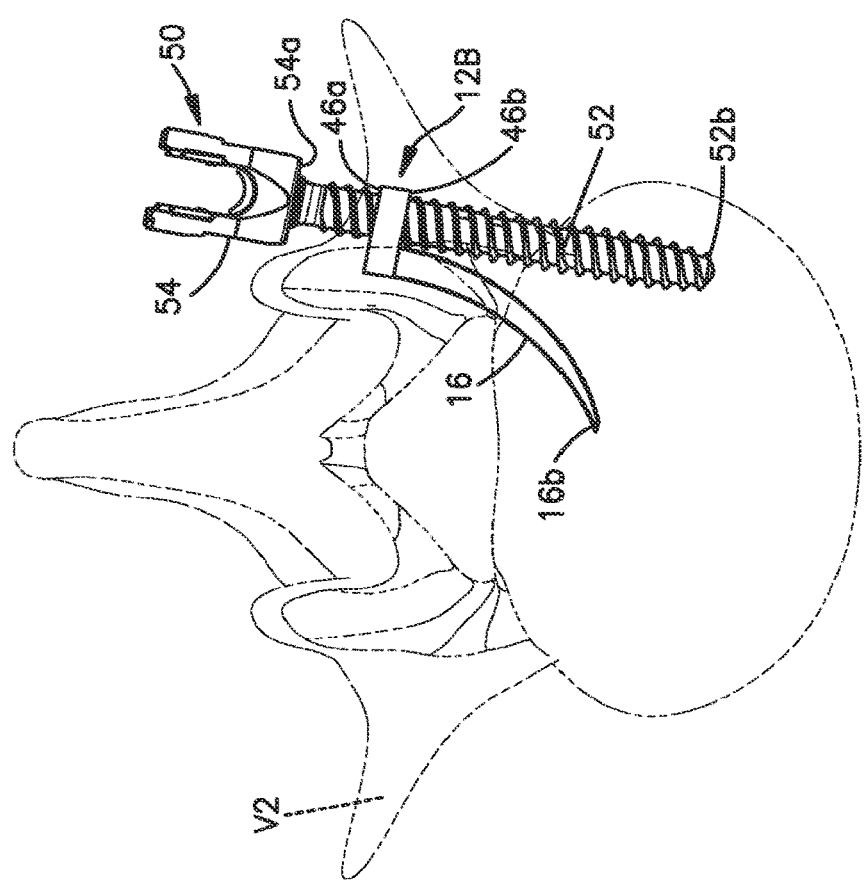
FIG. 6 is a cranial-caudal view of a vertebral body with the arcuate fixation member illustrated in FIGS. 4F inserted therein.
Figure 7:
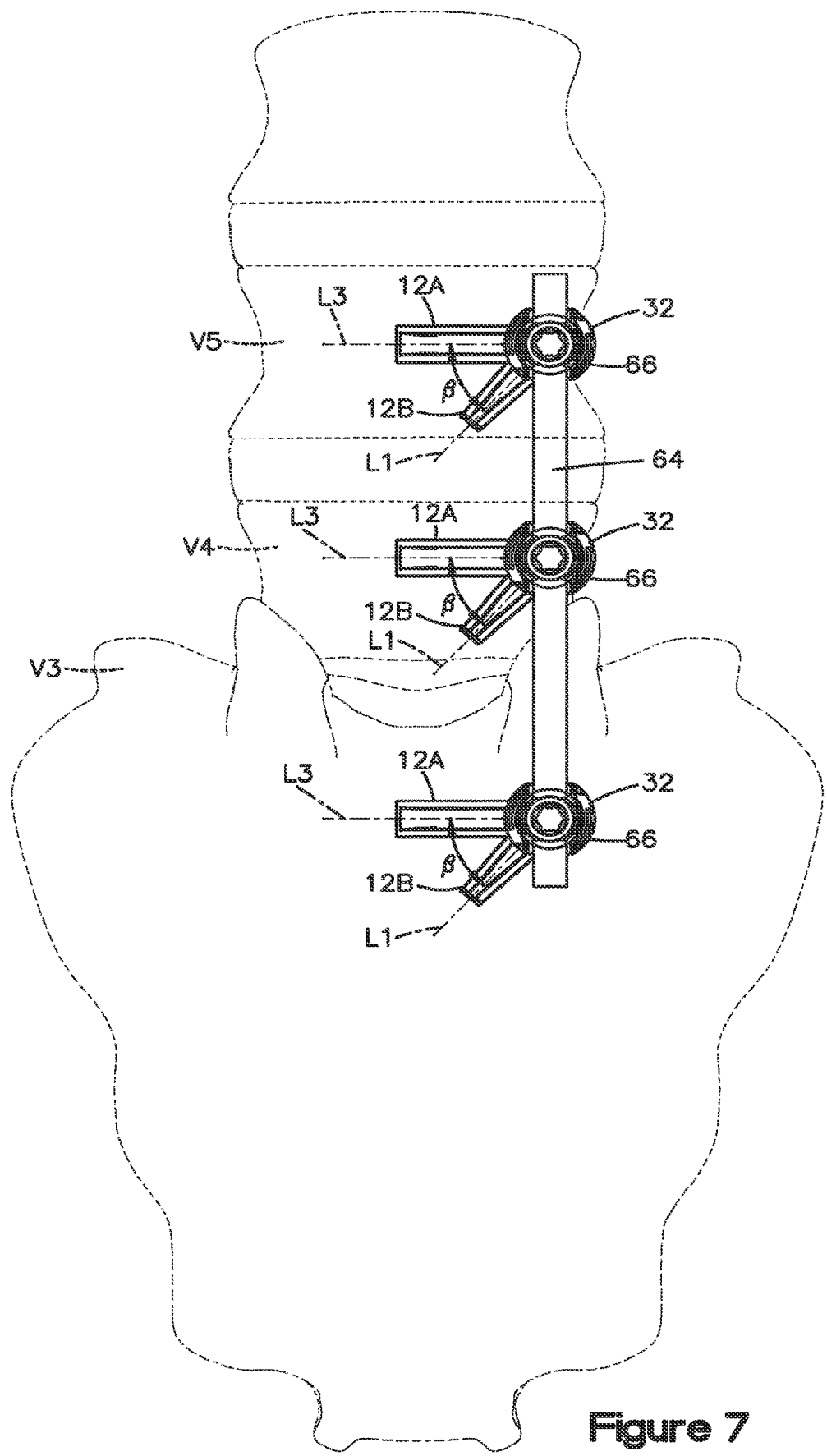
FIG. 7 is a posterior view of an example spinal fixation construct utilizing embodiments of the arcuate fixation members illustrated in FIG. 4F.

Now referring to FIGS. 5 to 7, example embodiments of the fixation system 10 incorporating various embodiments of the arcuate fixation member 12B are illustrated. In FIG. 5, an arcuate fixation member 12B with the aperture 48 formed within the tab body 46 has been inserted into a vertebral body V2. As depicted, the arcuate fixation member 12B has been inserted such that the lower surface 46b of the tab body 46 is engaged with the outer bone surface of the vertebral body V2. In an alternative embodiment, a recess (not shown) may be formed, for example by a boring instrument, within the outer bone surface of the vertebral body V2, the geometry of the recess configured to the receive the tab body 46 such that the upper surface 46a of the tab body 46 is substantially flush with the outer bone surface of the vertebral body V2 when the arcuate fixation member 12B is fully inserted into the vertebral body V2. Once the arcuate fixation member 12B is in a fully inserted position within the vertebral body V2, a fixation anchor 50 may be inserted into the aperture 48 of the tab body 46 and driven into to the underlying bone of the vertebral body V2. The fixation anchor 50 may be driven into the underlying bone of the vertebral body V2 until distal end 54a of the head 54 is flush against the upper surface 46a of the tab body 46 in an assembled configuration.

In the fully assembled configuration of FIG. 5, the arcuate fixation member 12B and the fixation anchor 50 form a stable triangular load bearing plane defined by the central curved axis L1 and the longitudinal shaft axis S1, and a direction extending between the body 16 of the arcuate fixation member 12B and the shaft 52 of the fixation anchor 50 (for instance, between the distal ends 16b and 52b of the arcuate fixation member 12B and the fixation anchor 50 respectively). This triangular load bearing plane provides additional structural integrity and enhanced resistance to pullout forces than typical fixation systems employing fixation members deployed along parallel longitudinal axes. Additionally, because the body 16 of the arcuate fixation member 12B and the shaft 52 of the fixation anchor 50 are angled with respect to each other, each of these anchors resists migration within the bone due, for instance, to longitudinal forces applied to the other bone anchor, that would tend to pull the bone anchor out of the underlying bone.

In FIG. 6, as in FIG. 5, an arcuate fixation member 12B with the curved guiding bore 62 formed within the tab body 46 has been inserted into the vertebral body V2. As depicted, the arcuate fixation member 12B has been inserted such that the lower surface 46b of the tab body 46 is engaged with the outer bone surface of the vertebral body V2. In an alternative embodiment, a recess (not shown) may be formed, for example by a boring instrument, within the outer bone surface of the vertebral body V2, the geometry of the recess configured to the receive the tab body 46 such that the upper surface 46a of the tab body 46 is substantially flush with the outer bone surface of the vertebral body V2 when the arcuate fixation member 12B is fully inserted into the vertebral body V2. Once the arcuate fixation member 12B is in a fully inserted position within the vertebral body V2, an arcuate fixation member 12A may be inserted into the curved guiding bore 62 of the tab body 46 and driven into to the underlying bone of the vertebral body V2. The arcuate fixation member 12A may be driven into the underlying bone of the vertebral body V2 until the distal end 32b of the head 32 is flush against the upper surface 46a of the tab body 46 in an assembled configuration.

In the fully assembled configuration of FIG. 6, the arcuate fixation member 12B and the arcuate fixation member 12A form a stable triangular load bearing plane defined by the central curved axis L1 and the central curved axis L3, and a direction extending between the bodies 16 of the arcuate fixation members 12B and 12A (for instance, between the distal ends 16b of the arcuate fixation members 12B and 12A respectively). This triangular load bearing plane provides additional structural integrity and enhanced resistance to pullout forces than typical fixation systems employing fixation members deployed along parallel longitudinal axes. Additionally, because the bodies 16 of the arcuate fixation members 12B and 12A are angled with respect to each other, each of these anchors resists migration within the bone due, for instance, to longitudinal forces applied to the other bone anchor, that would tend to pull the bone anchor out of the underlying bone.

In FIG. 7, an example embodiment of the spinal fixation system 10 used in a unilateral spinal fixation construct is illustrated. Three arcuate fixation members 12B with the curved guiding bores 62 formed within the tab bodies 46 have been driven into the bone of three adjacent vertebral bodies V3, V4, and V5. Three arcuate fixation members 12A have been inserted into the corresponding guiding bores of the three arcuate fixation members 12B and driven into the bone of the vertebral bodies V3, V4, and V5. Each assembled combination of arcuate fixation members 12B and 12A may be configured with a different angle β between the central curved axes L1 and L3, for example to conform to the individual anatomy of each of the vertebral bodies V3, V4, and V5. A spinal fixation rod 64 has been seated in the grooves 38 formed within the heads 32 of the arcuate fixation members 12A, and the fixation rod has been secured in place within each of the grooves 38 using appropriate pedicle screw caps, thereby fixing the unilateral spinal fixation construct in an assembled configuration. Each assembled combination of the arcuate fixation members 12B and 12A form one of the above-discussed triangular load bearing planes between the bodies 16 of the arcuate fixation members 12B and 12A in a respective one of the vertebral bodies V3, V4, and V5. The increased torsional and/or rotational rigidly characteristics exhibited by the fixation system 10 in this configuration when compared with typical pedicle screw spinal constructs make the fixation system 10 desirable for use in unilateral spinal fixation procedures. It should be noted that although FIG. 7 illustrates a unilateral spinal fixation construct using the arcuate fixation members 12B and 12A of the spinal fixation system 10, alternate example embodiments using one or more additional components of the spinal fixation system 10, for example including the use of one or more fixation anchors 50 in lieu of one or more of the arcuate fixation members 12A, including the use of one or more guiding members 14 in combination with one or more arcuate fixation members 12A, or any combination thereof, are possible and intended to be included within the scope of the instant disclosure.

Figure 8A:
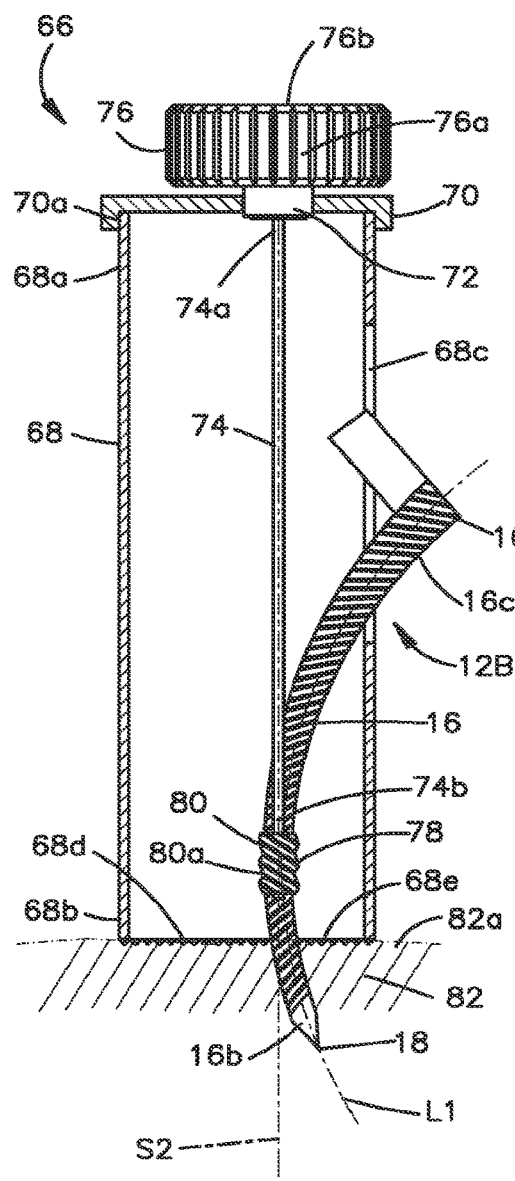
FIGS. 8A and 8B are side elevation views of an embodiment of an arcuate fixation member delivery instrument.
Figure 8B:
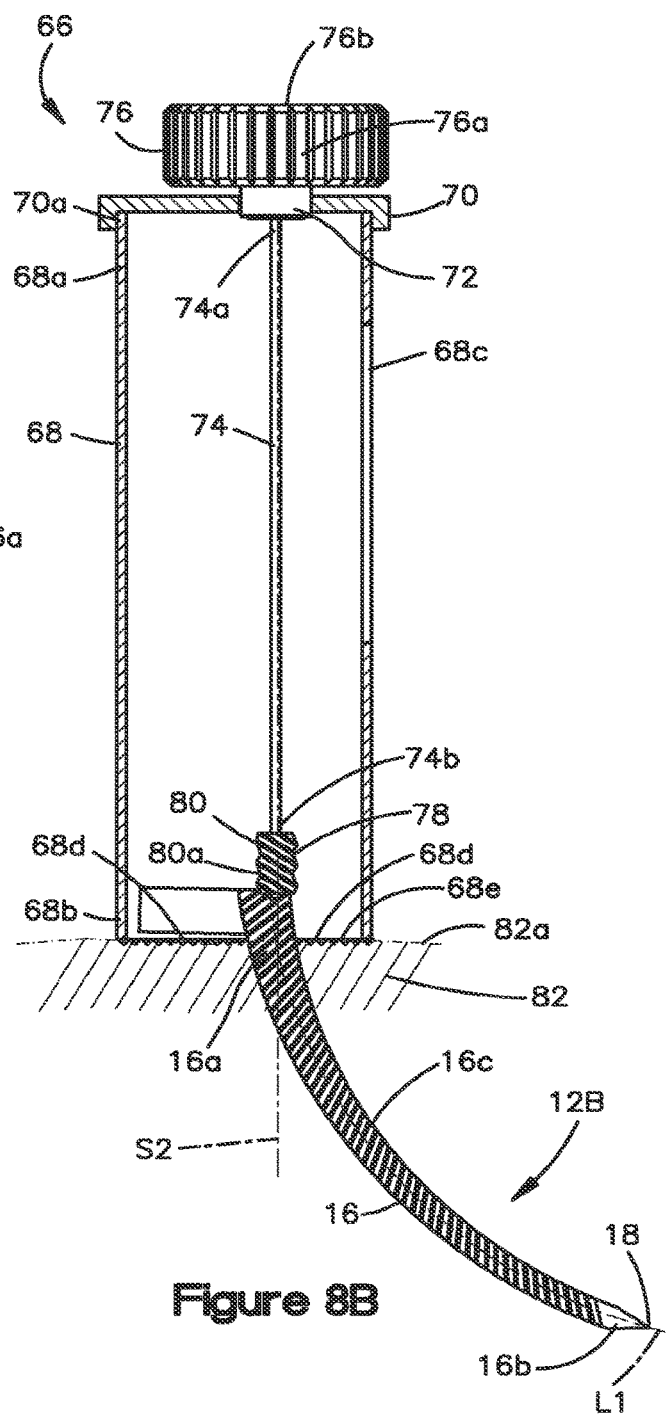

Now referring to FIGS. 8A and 8B, example embodiments of a delivery instrument 66 for use in inserting the arcuate fixation members 12A and/or 12B of the fixation system 10 into underlying structure or bone are illustrated. The delivery instrument 66 includes a hollow guide shaft 68 with a proximal end 68a and a distal end 68b opposite the proximal end. The guide shaft 68 may have a key 68c formed therein between the proximal and distal ends 68a and 68b. The geometry of the key 68c may be defined to allow an arcuate fixation member, for example the arcuate fixation member 12B, to pass laterally through the key 68c as it is being driven into underlying structure or bone. The distal end 68d of the guide shaft 68 may define engaging features 68e, for example serrated teeth, configured to engage underlying surface or bone when the delivery instrument 66 is positioned for insertion of the arcuate fixation members 12A and/or 12B.

In an example embodiment, a removable end cap 70 may be releasably affixed to the distal end 68a of the guide shaft 68. The end cap 70 may define an inner rim surface 70a with engagement features (e.g., threads) defined therein configured to releasably engage with complimentary engagement features formed at the distal end 68a of the guide shaft 68. Alternatively, the guide shaft 68 may include a solid end (not shown) formed in a plane perpendicular to the distal end 68a of the guide shaft 68. In example embodiments, the end cap 70 or the solid end may have an optional collar 72 coupled therein configured to receive a drive shaft 74 having a longitudinal axis S2, a proximal end 74a, and a distal end 74b opposite the proximal end. The collar may be configured to freely allow translation and/or rotation of the drive shaft 74, or may limit advancement and/or retraction of the drive shaft 74, for example by complimentary threads formed within the collar 72 and on the drive shaft, ratcheting features on the drive shaft, or the like. In alternative embodiments where collar 72 is omitted, the end cap 70 or the solid end may be configured to freely allow translation and/or rotation of the drive shaft 74, or may limit advancement and/or retraction of the drive shaft 74, for example by complimentary threads formed within the collar 72 and on the drive shaft, ratcheting features on the drive shaft, or the like.

The proximal end 74a of the drive shaft 74 may be coupled, above the end cap 70 or the solid end, to an actuator 76. The actuator may be configured to impart rotational and/or translational forces to the drive shaft 74. The actuator may have gripping features 76a defined thereon configured to allow for easier application of a rotational force to the actuator 76. In an example embodiment, the gripping features 76a may include features designed to enhance the hand grip of an operator, for example a series of vertical ribs, knurls, or the like. Alternatively, the gripping features 76a may be configured to engage complimentary features of a motorized driving instrument such as a drill. An upper surface 76b of the actuator 76 may be configured to receive an impaction force from a complimentary impaction instrument, for example a hammer, a mallet, a sonic hammer, a mechanical hammer, or the like.

An engaging head 78 may be coupled to the distal end 74b of the drive shaft 74. The engaging head 80 includes a body 80 defining an outer surface 80a. The outer surface 80a of the body 80 may have engaging features 80b defined therein configured to matably engage with complimentary engaging features 16c defined between the proximal end 16a and the distal end 16b of the body 16 of the arcuate fixation member 12B. In an example embodiment, the complimentary engaging features 80b and 16c are complimentary threads. In another embodiment, the engaging head 80 includes a gripping mechanism (not shown) configured to releasably engage the engaging features 16c of the of the body 16 of the arcuate fixation member 12A and/or 12B. The gripping features of the engaging head 80 may be controllable via the actuator 76.

An optional cutting shaft (not shown) may be configured to be received within the collar 72 or the solid end, the cutting shaft having a proximal end that may be coupled, above the end cap 70 or the solid end, to the actuator 76, and a distal end opposite the proximal end, the distal end having a cutting tool coupled thereto, the cutting tool configured to cut an initial pathway into the underlying structure, the initial pathway being of similar cross sectional geometry but proportionately smaller cross sectional area of an arcuate fixation member 12A or 12B that is to be driven into the initial pathway and the underlying structure. The cutting shaft may be configured similarly to and advanced and/or retracted within the guide shaft 68 similarly to the drive shaft 74.

In an example method of using rotational insertion via the delivery instrument 66 to insert an arcuate fixation member 12B, the arcuate fixation member 12B is inserted through the key 68c of the guide shaft 68 until the engaging features 16c at the distal end 16b of the body become matably engaged with the engaging features 80b of the body 80 of the engaging head 78. When assembled in this pre-insertion configuration, the central curved axis L1 will be substantially coincident with the longitudinal axis S2 of the drive shaft 74, and the tip 18 of the arcuate fixation member 12B will in a position slightly above and substantially perpendicular to an outer surface 82a of an underlying structure 82 (e.g., bone) into which the arcuate fixation member 12B is to be driven. The delivery instrument 66 may then be maneuvered into position within the patient such that the engaging features 68e of the guide shaft 68 engage with the outer surface 82a of the underlying structure 82, and the tip 18 of the arcuate fixation member 12B is positioned above the desired insertion point for the arcuate fixation member 12B. The threads of the complimentary engaging features 80b and 16c may be configured so that as a rotational force about the longitudinal axis S2 is imparted to the actuator 76, the engaging head 80 applies a downward biasing force to the tip 18 and the body 16 of the arcuate fixation member 12B, causing the arcuate fixation member 12B to be driven through the outer surface 82a and into the underlying structure 82 along the longitudinal axis L1. The rotational force may be imparted to the actuator 76 by hand via an operator of the delivery instrument 66, via rotational force from a motorized source, or any combination thereof.

In an example method of using a combination of rotational and impactional insertion via the delivery instrument 66 to insert an arcuate fixation member 12B, the arcuate fixation member 12B is inserted through the key 68c of the guide shaft 68 until the engaging features 16c at the distal end 16b of the body become matably engaged with the engaging features 80b of the body 80 of the engaging head 78. When assembled in this pre-insertion configuration, the central curved axis L1 will be substantially coincident with the longitudinal axis S2 of the drive shaft 74, and the tip 18 of the arcuate fixation member 12B will in a position slightly above and substantially perpendicular to an outer surface 82a of an underlying structure 82 (e.g., bone) into which the arcuate fixation member 12B is to be driven. The delivery instrument 66 may then be maneuvered into position within the patient such that the engaging features 68e of the guide shaft 68 engage with the outer surface 82a of the underlying structure 82, and the tip 18 of the arcuate fixation member 12B is positioned above the desired insertion point for the arcuate fixation member 12B.

The threads of the complimentary engaging features 80b and 16c may be configured so that as a rotational force about the longitudinal axis S2 is imparted to the actuator 76, the drive shaft 74 is biased in an upward direction along the longitudinal axis S1, causing the drive shaft 74 and the actuator 76 to be displaced within the guide shaft 68 in an upward direction away from the outer surface 82a of the underlying structure 82, while maintaining engagement of the complimentary engaging features 80b and 16c. An downward impaction force may then be imparted to the actuator 76, causing the actuator 76, the drive shaft 74, and the engaging head 80 to be biased in a downward direction toward the outer surface 82a of the underlying structure 82. The downward biasing force applied to the engaging head 80 is imparted to the arcuate fixation member 12B via the complimentary engaging features 80b and 16c, causing the tip 18 and the body 16 of the arcuate fixation member 12B to be driven though the outer surface 82a and into the underlying structure 82 along the longitudinal axis L1. The arcuate fixation member 12B may be driven into a fully inserted position via a successive series of rotational and impactional forces imparted to the actuator, such that the drive shaft 74 and actuator 76 are initially displaced upward from a starting position via rotation, then biased downward via impaction until the actuator 76 returns to its starting position, simultaneously biasing the arcuate fixation member 12B into the underlying structure 82, then biased upward via rotation from the starting position again, and so on. The successive rotational and/or impactional forces may be imparted to the actuator 76 by hand via an operator of the delivery instrument 66, via rotational and/or impactional forces from a motorized source, or any combination thereof. It should be noted that while FIGS. 8A and 8B and the accompanying description are concerned primarily with insertion of the arcuate fixation member 12B, the same delivery instrument 66 and methods of use therefore may be used to insert the arcuate fixation member 12A.

Referring now to FIGS. 9A to 9M, an example embodiment of an intervertebral implant system 100 comprising an arcuate fixation member 12C, an intervertebral implant 108, a fixation plate 116, a blocking plate 132, and a locking screw 138 is illustrated. As will become appreciated from the description below, one or more fixation members 12C may be utilized to securely anchor an assembled configuration of intervertebral implant system 100 within an intervertebral space between adjacent vertebral bodies. Unless otherwise indicated, the intervertebral implant system 100 and its components can be manufactured from any suitable biocompatible material known in the art including but not limited to titanium, titanium alloy such as TAN, stainless steel, reinforced plastics, allograft bone, and the like.

The arcuate fixation member 12C includes a body 102 defining a proximal end 102a and a distal end 102b opposite the proximal end. The distal end 102b may comprise a tip 104 configured to cut into underlying structure or bone. The body 102 may further define an intermediate portion between the proximal end 102a and the distal end 102b that is curved along a central curved axis L1. In an embodiment, the intermediate portion is curved along substantially the entire length of the body 102 between the proximal end 102a and the distal end 102b. Alternatively, one or more distinct portions of the intermediate portion between the proximal end 102a and the distal end 102b may be curved (not shown).

In an embodiment, the intermediate portion is curved along the central curved axis L1 in accordance with a uniform radius of curvature R1. Alternatively, the intermediate portion may define a non-uniform radius of curvature along the central curved axis L1. In a preferred embodiment, the curvature of the intermediate portion may be smooth and continuous. Alternatively, the curvature of the intermediate portion may be defined by a series of substantially straight sections (not shown), with each substantially straight section aligned along an individual longitudinal axis corresponding to the individual section, where the magnitude of an angle α with respect to a perpendicular reference axis extended from the proximal end 102a increases in magnitude with the distance of each subsequent straight section from the proximal end 102a.

The arcuate fixation member 12C may have a head 106 defined at the proximal end 102a of the body 102. The head 106 may extend radially outward from the proximal end 102a of the body 102 in a direction perpendicular to the longitudinal axis L1. In an example embodiment, the head 106 may extend from the body 102 in a direction generally opposite from the direction of curvature of the body 102, as depicted in FIGS. 9A and 9B. In alternative embodiments, the head 106 may extend from the body 102 in a direction generally towards the direction of curvature of the body 102. The head may define an upper surface 106a configured for multi-angular engagement with a complementary surface of a delivery instrument, and a lower surface 106b opposite the upper surface and configured to engage another component of the intervertebral implant system 100, for example the fixation plate 116, when the arcuate fixation member 12C is in a fully inserted position.

Figure 9C:
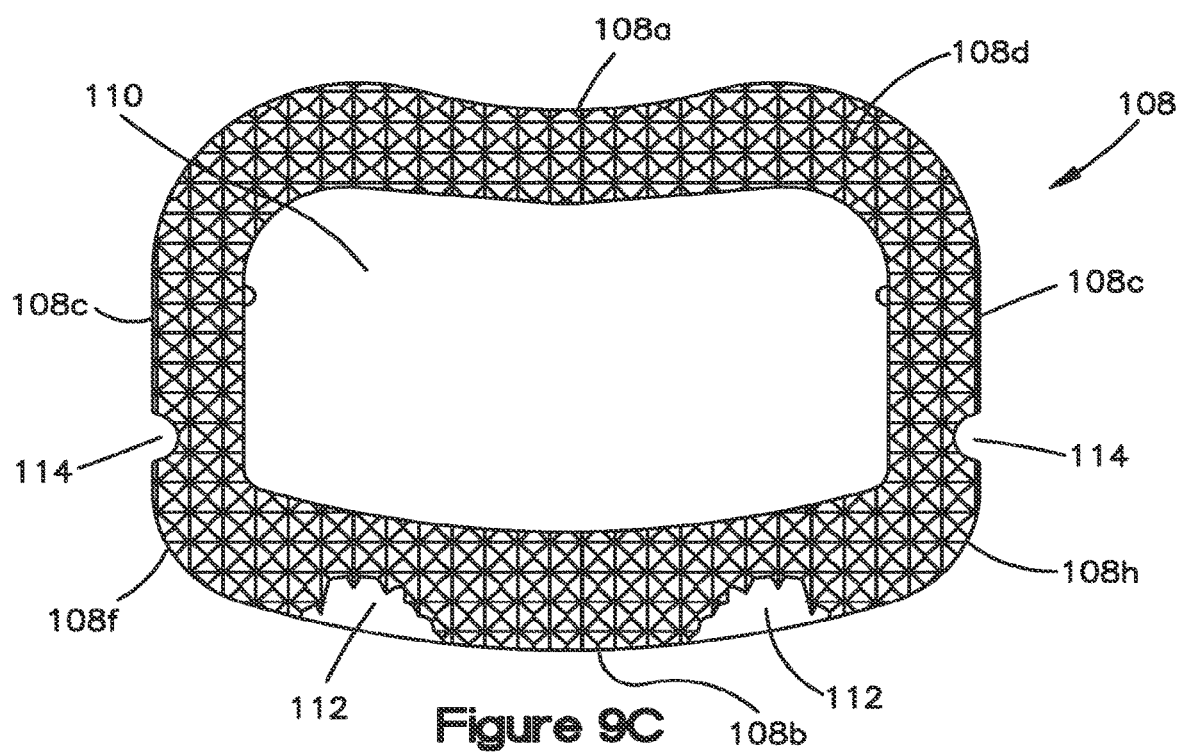
FIG. 9C is a top elevation view of an embodiment of an intervertebral implant for use with arcuate fixation members.
Figure 9D:
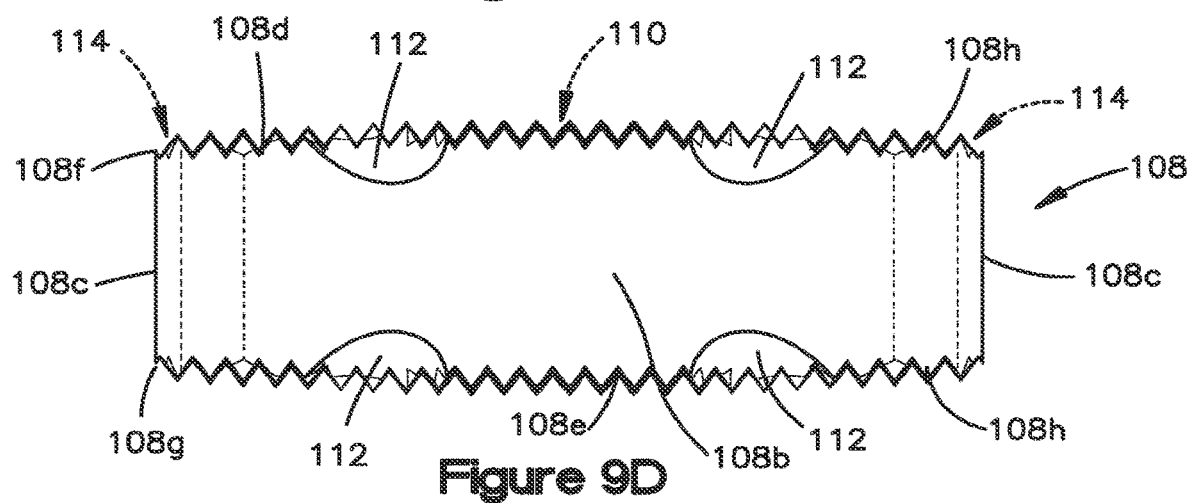
FIG. 9D is a front elevation view of the intervertebral implant illustrated in FIG. 9C.

The intervertebral implant 108 is defined by a posterior side 108a, an anterior side 108b opposite the posterior side, lateral sides 108c, an upper surface 108d, and a lower surface 108e opposite the upper surface. In an example embodiment, a portion of the posterior side 108a between the lateral sides 108c may be curved inwardly in the direction of the anterior side 108b, defining a rounded, generally rectangular kidney-like footprint, as depicted in FIG. 9C. In an alternative embodiment, a portion of the posterior side 108a between the lateral sides 108c may be curved outwardly in a direction away from the anterior side 108b (not shown). In another alternative embodiment, the posterior side 108a may be substantially straight between the lateral sides 108c, defining a rounded, generally rectangular footprint (not shown). The intervertebral implant 108 may have a central bore 110 formed therethrough, the shape of which substantially conforms to the footprint of the intervertebral implant 108 (e.g., a rounded, generally rectangular kidney-like footprint, or a rounded, generally rectangular footprint, depending upon the geometry of the posterior side 108a). The central bore 110 can be filled with bone growth inducing substances to allow bony ingrowth and to assist in fusion between the intervertebral implant 108 and adjacent vertebral bodies.

In an example embodiment of the intervertebral implant 108, the upper and lower surfaces 108d and 108e may have gripping features 108h such as teeth, spikes, or similar structures, formed thereon and configured to facilitate gripping engagement between the upper and lower surfaces 108d and 108e and the end plates of adjacent vertebral bodies. The teeth 112 may be pyramidal, saw toothed or other similar shapes. In alternative embodiments of the intervertebral implant 108, portions of and/or the entirety of the upper and lower surfaces 108d and 108e may be substantially smooth and devoid of any protrusions. Upper and lower edges 108f and 108g, defined where the upper and lower surfaces 108d and 108e intersect with the posterior, anterior, and lateral sides 108a, 108b, and 108c respectively around the outer perimeter of the intervertebral implant 108, may be rounded (not shown). In an example embodiment, the upper and lower edges 108f and 108g may be rounded using a uniform radius of curvature around the perimeter of the implant. In an alternative embodiment, the upper and lower edges 108f and 108g may be rounded using a non-uniform radius of curvature around the perimeter of the implant. In another alternative embodiment, the upper and lower edges 108f and 108g along the anterior side 108b may be rounded with a greater radius than the remainder of the upper and lower edges 108f and 108g, such that a bull nose outer surface (not shown) is created on the anterior side 108b of the implant. Rounding upper and lower edges 108f and 108g may facilitate easier insertion of the intervertebral implant 108, for example by minimizing required distraction of the end plates of adjacent vertebral bodies.

Figure 9E:
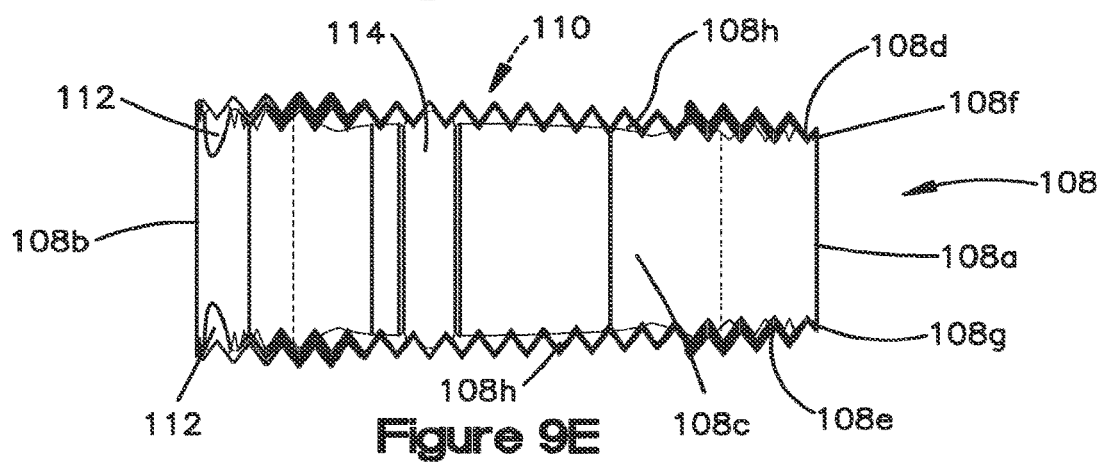
FIG. 9E is a side elevation view of the intervertebral implant illustrated in FIG. 9C.
Figure 9F:
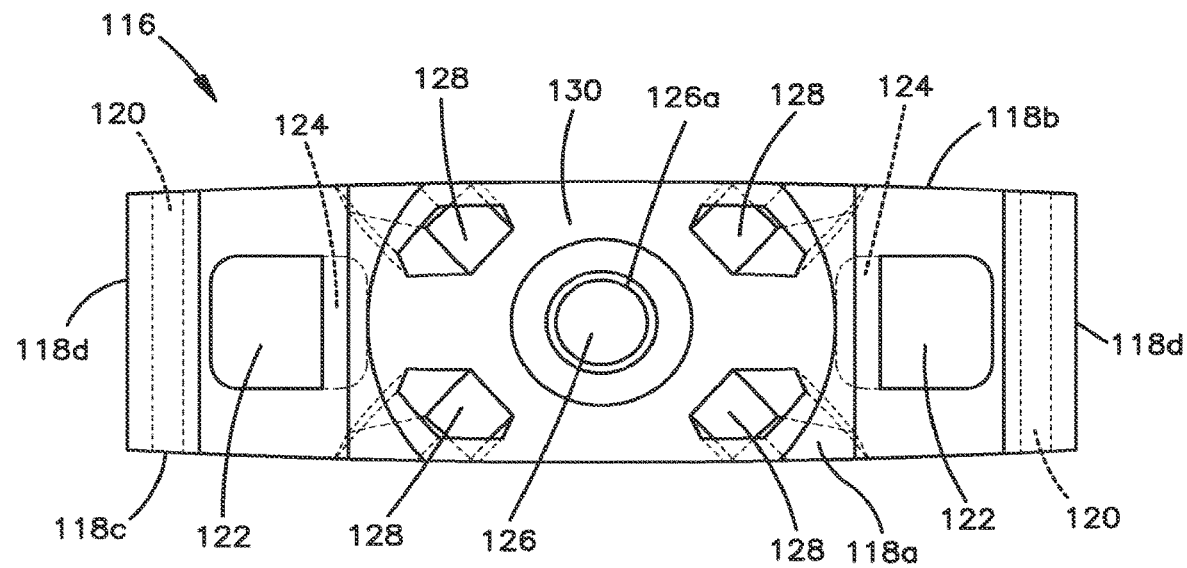
FIG. 9F is a front elevation view of an embodiment of a fixation plate for use with the intervertebral implant illustrated in FIGS. 9C to 9E.
Figure 9G:
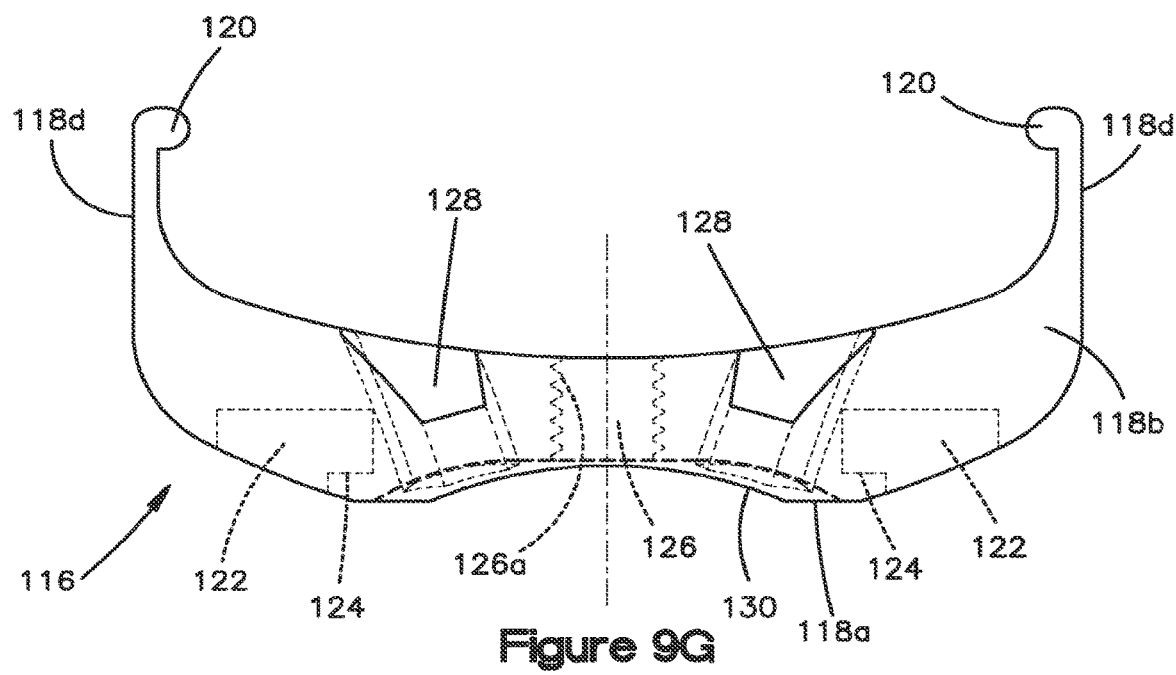
FIG. 9G is a top elevation view of the fixation plate illustrated in FIG. 9F.
Figure 9K:
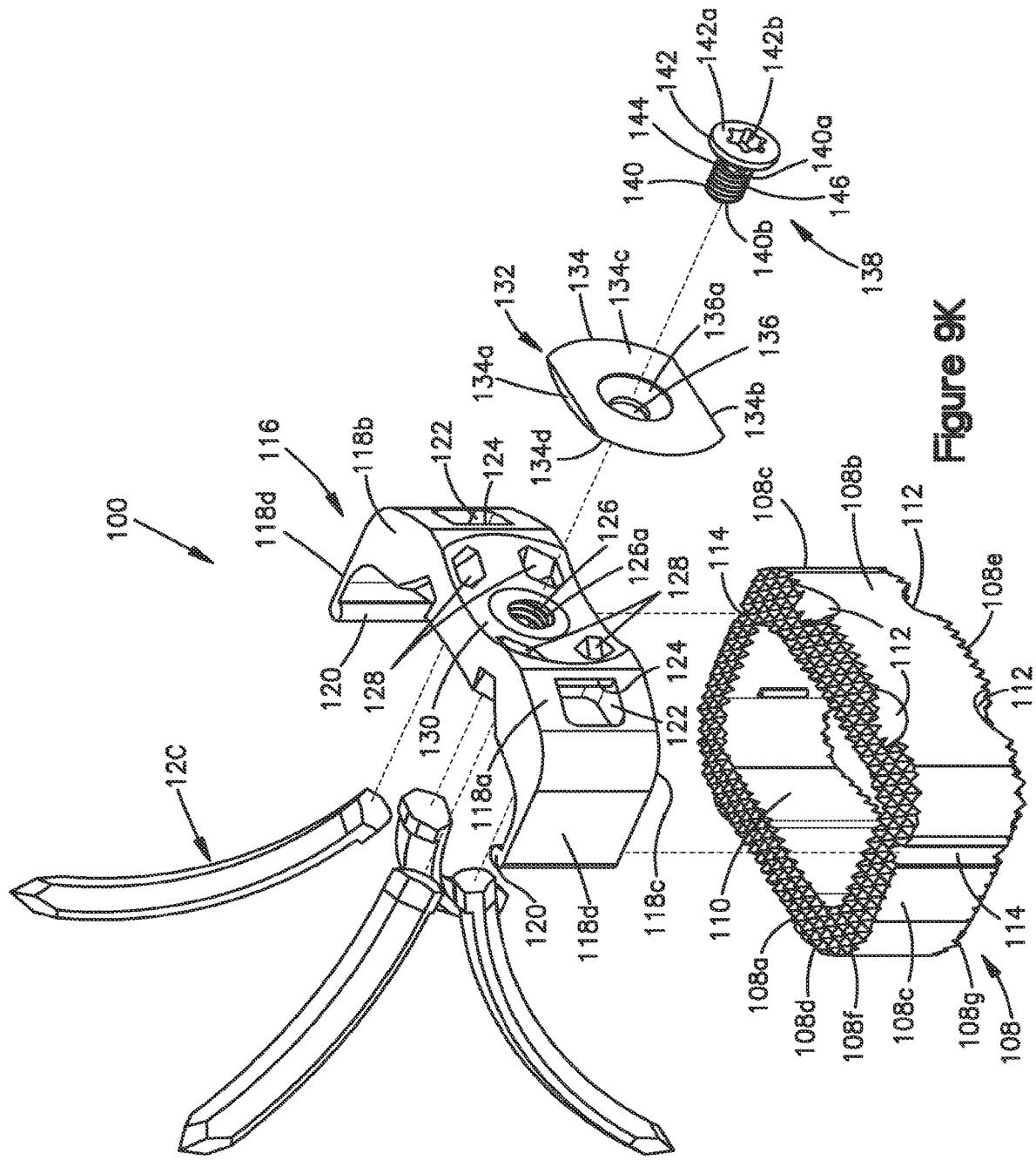
FIG. 9K is an exploded view of an assembly utilizing the components illustrated in FIGS. 9A to 9J.

In an example embodiment, the intervertebral implant 108 has a generally wedge-shaped side-view profile. As illustrated in FIG. 9E, this wedge shape is defined by a gradual decrease in the height of the intervertebral implant 108 (as measured between the upper and lower surfaces 108d and 108e) extending between the posterior side 108a in the direction of the anterior side 108b. The intervertebral implant 108 has a generally constant height between lateral sides 108c. In alternative embodiments, the intervertebral implant 108 may have a gradual increase in height followed by a gradual decrease in height extending from one lateral side 108c to the other, and/or may have a generally constant height between the posterior and anterior sides 108a and 108b, or may have convex and/or concave upper and lower surfaces 108d and 108e, thereby defining a gradual increase in height followed by a gradual decrease in height extending from the posterior side 108a to the anterior side 108b and from one lateral side 108c to the other.

A plurality of grooves 112 may be formed within the intervertebral implant 108 where the upper and lower surfaces 108d and 108e intersect with the anterior side 108b. The grooves 112 may be concave and may be configured to align with arcuate grooves 128 of the fixation plate 116 when the intervertebral implant 108 and the fixation plate 116 are in an assembled configuration. In an example embodiment, the grooves 112 may be substantially smooth and devoid of any protrusions. Retaining grooves 114 may be formed within the lateral sides 108c of the intervertebral implant 108 between the upper and lower surfaces 108d and 108e. The retaining grooves 114 may be configured to releasably engage complementary engaging ribs 120 of the fixation plate 116.

The fixation plate 116 is defined by a generally C-shaped, channel-like body 118 that includes an anterior side 118a with upper and lower sides 118b and 118c opposite each other, and lateral sides 118d extending from opposite sides of the anterior side 118a in a generally perpendicular direction from the anterior side 118a. The anterior, upper, lower, and lateral sides 118a, 118b, 118c, and 118d may form a generally channel-like structure (in essence, a cradle) which may be configured to receive the anterior side 108b and at least a portion of the lateral sides 108c in partial nested engagement. As such, the upper and lower sides 108b and 108c may define gradual increases and/or decreases in height in a posterior direction from the anterior side 118a and/or between the lateral sides 108d, in order to generally conform the fixation plate 116 to the geometry of the intervertebral implant 108. The lateral sides 118d may have engaging ribs 120 formed thereon at the ends opposite the anterior side 118a, the engaging ribs 120 configured to be releasably received within the retaining grooves 114 of the intervertebral implant 108.

The anterior side 118a of the fixation plate 116 may have a pair of apertures 122 formed therethrough configured to receive grasping features of a delivery instrument. In an example embodiment, the apertures 122 may be D-shaped, as illustrated in FIG. 9C. However any other aperture shape may be defined as appropriate. The apertures 122 may have a retaining rib 124 formed therein configured to engage with a complimentary grasping rib of the delivery instrument. The anterior side 118a of the fixation plate 116 may also have a central bore 126 formed therethrough having an inner surface 126a with threads configured to engage complimentary threads of a locking screw 138. The anterior side 118a of the fixation plate 116 may also have a concave recess 130 formed therein configured to receive a complimentary convex surface 134d of the blocking plate 132.

The anterior side 118a of the fixation plate 116 may also have a plurality of arcuate grooves 128 formed therethrough configured to slidably receive the arcuate fixation members 12C and to define an insertion trajectory for each of the arcuate fixation members 12C. In an example embodiment, the arcuate grooves 128 may have a generally uniform cross sectional geometry configured to closely conform to the cross sectional geometry of the body 102 of the arcuate fixation member 12C between the head 106 and the distal end 102b. When an arcuate fixation member 12C is in a fully inserted position within a respective arcuate groove 128, the lower surface 106b of the head 106 will be engaged with the outer surface of the anterior side 118a of the fixation plate 116. Because the upper surface 106a of the head 106 will not be flush with the outer surface of the anterior side 118a of the fixation plate 116 in this configuration, it may be desirable to omit the blocking plate 132 and the locking screw 138. In an alternative embodiment, the arcuate grooves 128 have a recessed ledge formed therein in the area where the arcuate grooves 128 intersect with the outer surface of the anterior side 118a of the fixation plate 116, the recessed ledge being configured to receive the lower surface 106b of the head 106 when the arcuate fixation member 12C is in a fully inserted position, such that the upper surface 106a of the head 106 is substantially flush with the outer surface of the anterior side 118a of the fixation plate 116.

The arcuate grooves 128 may be disposed about the central bore 126 in any desired configuration and may define any insertion trajectories as appropriate. In the example embodiment depicted in FIGS. 9C to 9J, the arcuate grooves 128 are formed in opposing quadrants around the central bore 126, with two arcuate grooves 128 located near the upper side 118b and defining two generally cranial insertion trajectories, and two arcuate grooves 128 located near the lower side 118c and defining two generally caudal insertion trajectories. It should be noted that this configuration of arcuate groove 128 locations and arcuate fixation member 12C insertion trajectories is merely an example, and the scope of the instant disclosure should not be limited thereto.

The blocking plate 132 is defined by a generally disc-shaped body 134 with planar upper and lower surfaces 134a and 134b, an anterior surface 134c, and a posterior surface 134d. The upper and lower surfaces 134a and 134b and the height of the body 134 (as measured between the upper and lower surfaces 134a and 134b) may be defined to match the height (as measured between the upper and lower surfaces 118b and 118c) of the anterior side 118a of the fixation plate 116 when the blocking plate 132 is in a fully assembled configuration. The anterior surface 134c of the body 134 may be generally planar, or may be defined to match the outer surface of the anterior side 118a of the fixation plate 116 when the blocking plate 132 is in a fully assembled configuration. The posterior surface 134d may be defined as a convex surface configured to engage with the concave recess 130 formed in the anterior side 118a of the fixation plate 116 when the blocking plate 132 is in a fully assembled configuration. The body 134 may have an aperture 136 formed therethrough. In an example embodiment, the diameter of the aperture may be slightly larger than the diameter of the central bore 126 of the fixation plate 116, such that a locking screw 138 may be inserted into the aperture with no interference therebetween. In another embodiment, the diameter of the aperture 136 may be substantially the same as that of the central bore 126, and the inner surface of the aperture may have threads formed thereon, the threads configured to engage complimentary threads of the locking screw 138. The aperture 136 may further be defined by a concave recess 136a formed within the anterior surface 134c, the concave recess 136a configured to receive the convex head 142 of the locking screw 138.

The locking screw 138 includes a shaft 140 that defines longitudinally opposing proximal and distal ends 140a and 140b, respectively, and a head 142 coupled to the proximal end 140a of the shaft 140, either directly or indirectly via an unthreaded neck 144 that is coupled between the proximal end 140a of the shaft 140 and the head 142. The head 142 can define a generally convex shape between the interface of the head 142 and the neck 144 that extends outward towards a proximal end 142a of the head 142. The convex shape of the head may be configured to engage the concave recess 136a of the blocking plate 132. Of course, the head 142 can assume any other suitable alternative shape as appropriate. Helical threads 146 extend radially out from the shaft 140 at locations at and between the proximal and distal ends 140a and 140b that are configured to engage complementary threads on the inner surface 126a of the central bore 126 of the fixation plate 116. Thus, a substantial entirety of the shaft 140 between the proximal and distal ends 140a and 140b may be threaded. The distal end 142a of the head 142 may have driving features 142b defined therein, designed to engage with complementary driving features of a delivery instrument.

Referring now to FIGS. 9I and 9J, an example embodiment of the intervertebral implant system 100 in a nearly completely assembled configuration is illustrated. FIG. 9I depicts the intervertebral implant system 100 partially assembled outside of an intervertebral space (the blocking plate and locking screw have been omitted for simplicity). The intervertebral implant 108 has been seated within the fixation plate 116 such that the retaining ribs are seated with the retaining grooves on the lateral sides of the intervertebral implant 108. Four arcuate fixation members 12C have been inserted through corresponding arcuate grooves within the fixation plate 116, and have been driven to an almost fully inserted position. In a final assembled configuration, the arcuate fixation members 12C would be driven into their fully inserted position, the blocking plate would be received within the concave recess in the anterior side of the fixation plate, and the locking screw would be driven into the central bore of the fixation plate and finally tightened, thereby blocking the arcuate fixation members 12C from backing out of the assembled intervertebral implant system 100.

Figure 9M:
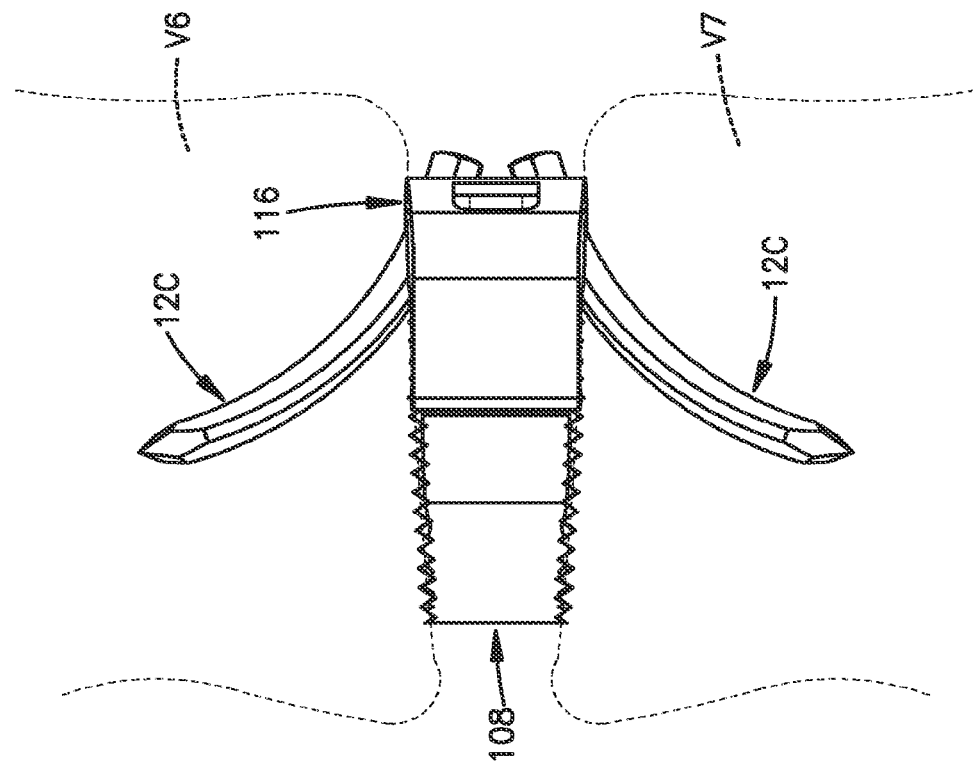
FIG. 9M is a side elevation view of the assembly illustrated in FIG. 9L inserted into an intervertebral space.
Figure 9L:
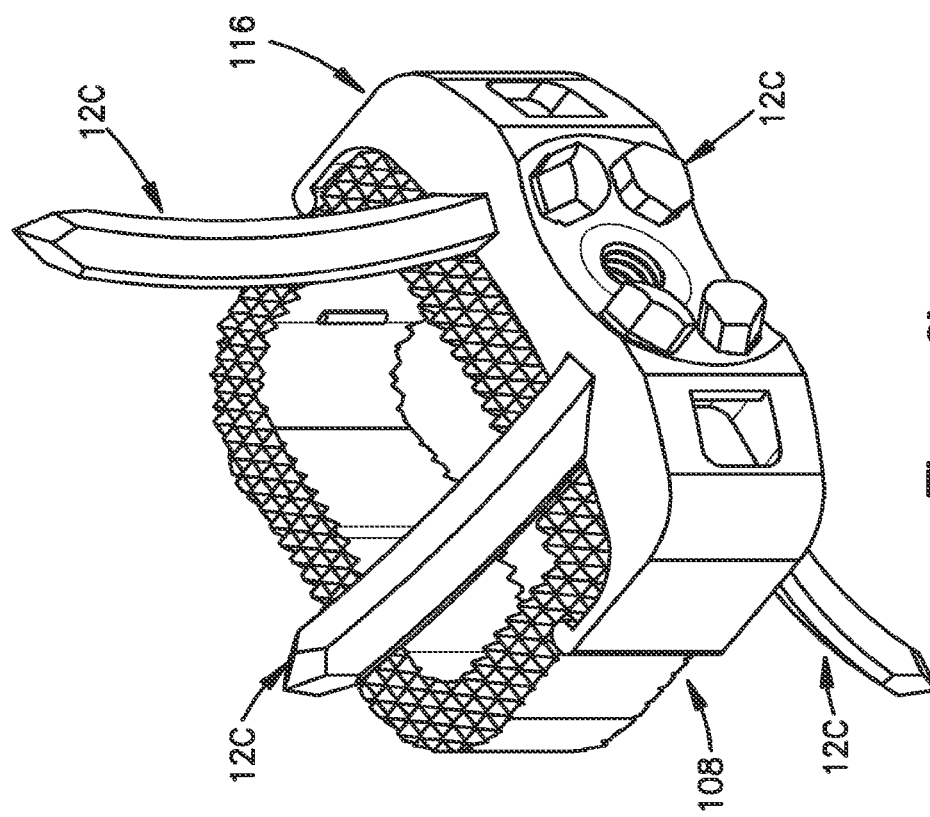
FIG. 9L is a perspective view of an assembly utilizing the components illustrated in FIGS. 9A to 9J.

FIG. 9M depicts an example embodiment of the intervertebral implant system 100 partially assembled inside of an intervertebral space between adjacent vertebral bodies V6 and V7 (the blocking plate and locking screw have been omitted for simplicity). As an initial step, the intervertebral implant 108 has been prepared for insertion, for example by being packed a with bone growth inducing substance and or/having its outer surfaces properly prepared, and has been seated within the fixation plate 116 such the retaining ribs are seated with the retaining grooves on the lateral sides of the intervertebral implant 108. The intervertebral implant 108 was then inserted into the intervertebral space between the adjacent vertebral bodies V6 and V7 using a delivery instrument that is described in greater detail below. The delivery instrument was then used to deliver the four arcuate fixation members 12C into the arcuate grooves in the fixation plate and drive them into an almost fully inserted position. During the final steps of the assembly process, the delivery instrument would be used to drive the arcuate fixation members 12C into their fully inserted position, the blocking plate would be received within the concave recess in the anterior side of the fixation plate, and the locking screw would be driven into the central bore of the fixation plate and finally tightened, thereby blocking the arcuate fixation members 12C from backing out of the assembled intervertebral implant system 100.

Referring now to FIGS. 10A to 10J, another example embodiment of the intervertebral implant system 100 comprising an arcuate fixation member 12C, an intervertebral implant 148, a fixation plate 156, a blocking plate 180, and a locking screw 138 is illustrated.

Figure 10A:
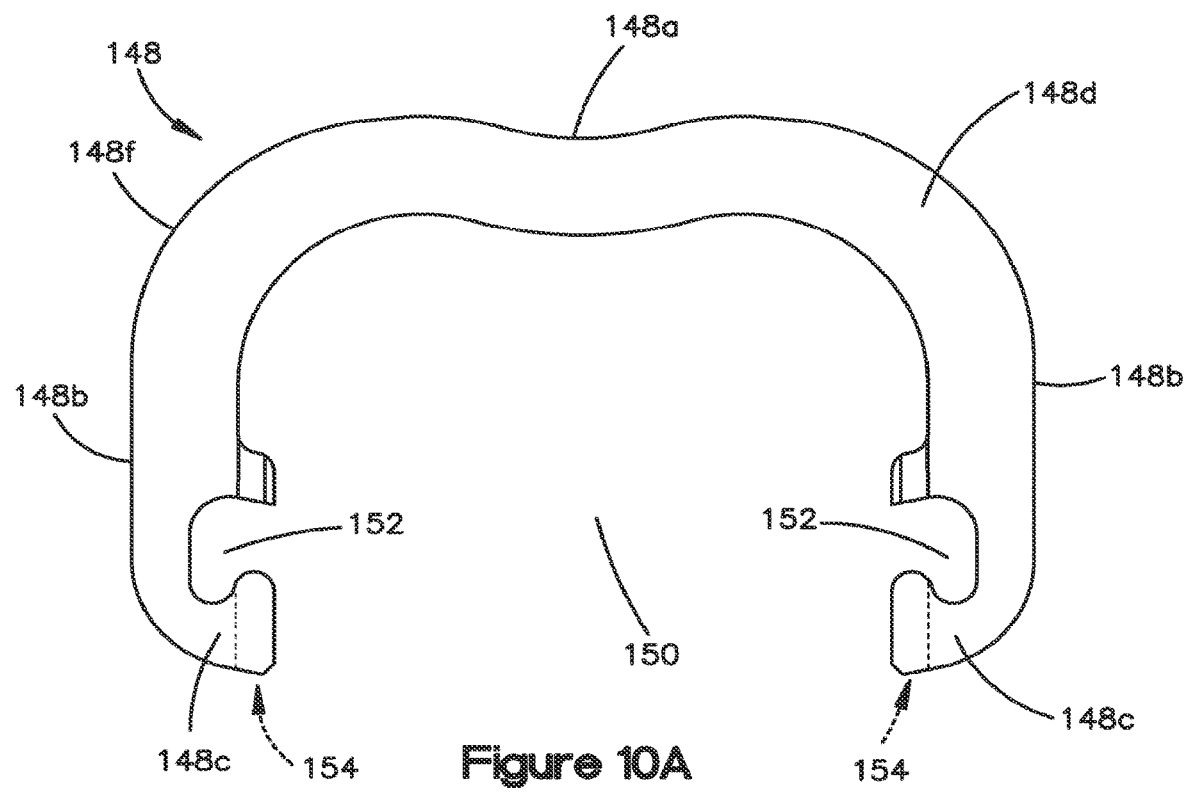
FIG. 10A is a top elevation view of another embodiment of an intervertebral implant for use with arcuate fixation members.
Figure 10B:
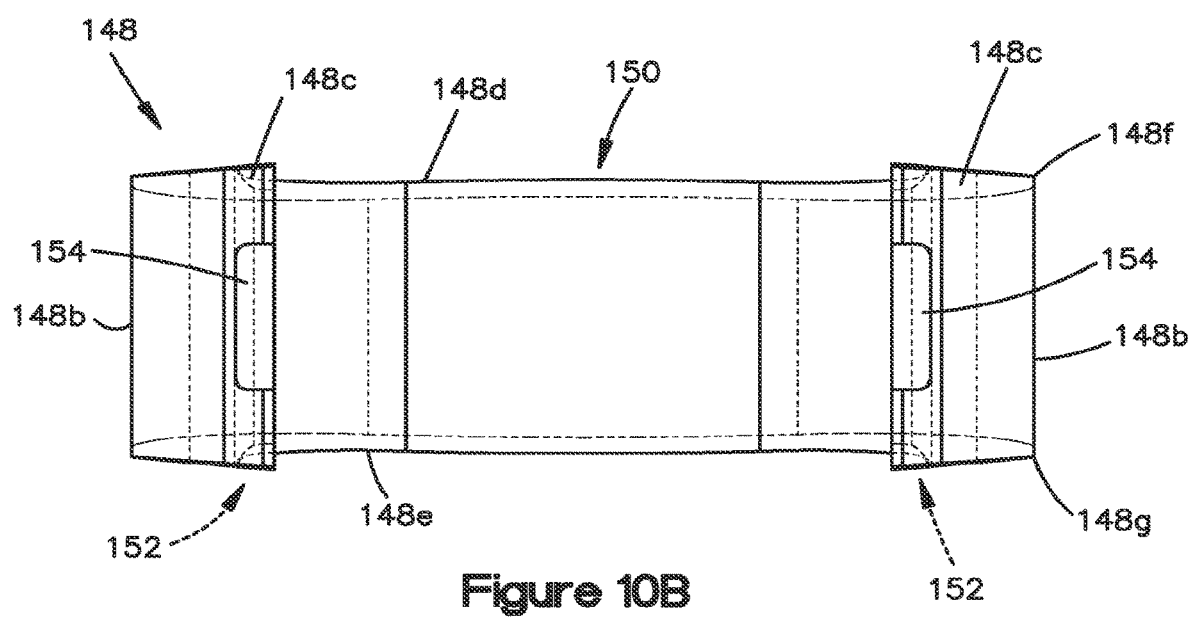
FIG. 10B is a front elevation view of the intervertebral implant illustrated in FIG. 10A.
Figure 10C:
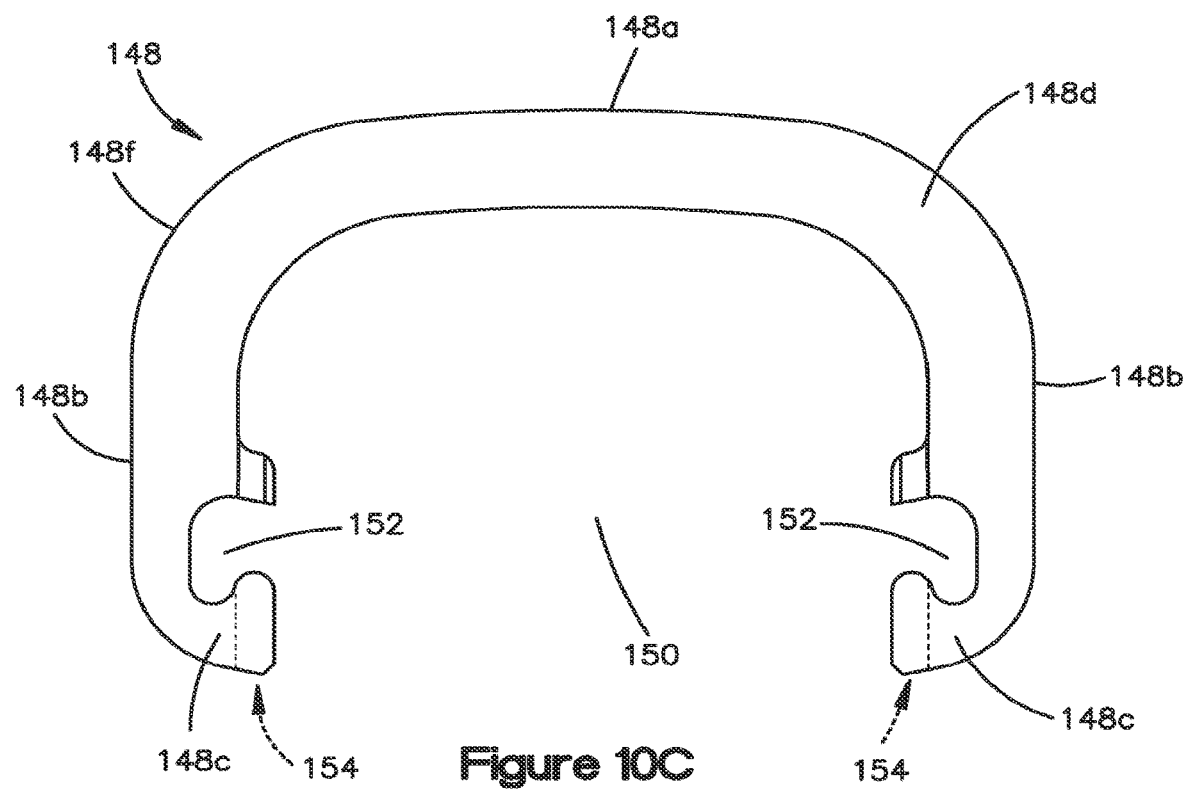
FIG. 10C is a top elevation view of another embodiment of an intervertebral implant for use with arcuate fixation members.
Figure 10D:
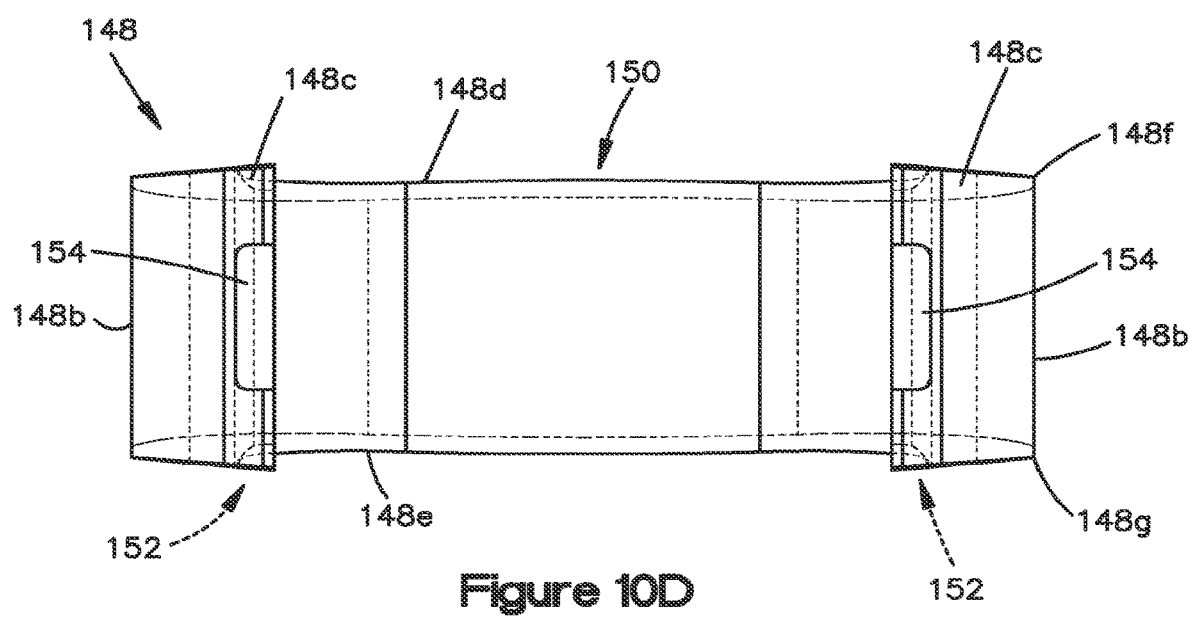
FIG. 10D is a front elevation view of the intervertebral implant illustrated in FIG. 10C.
Figure 10E:
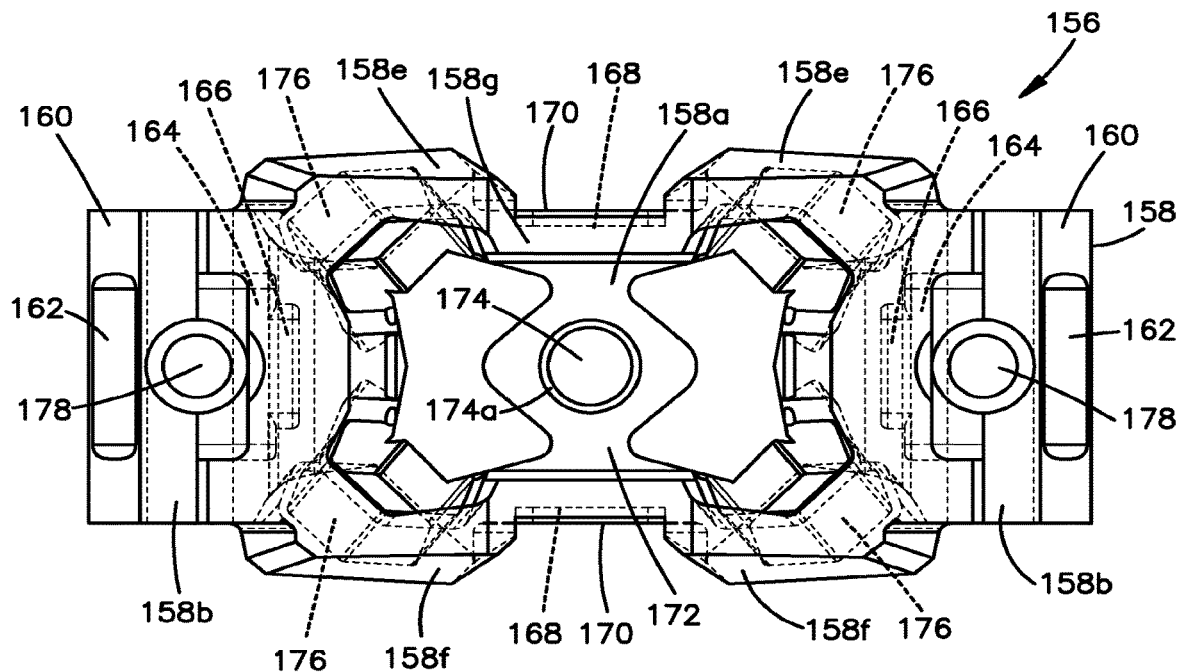
FIG. 10E is a front elevation view of an embodiment of a fixation plate for use with the intervertebral implants illustrated in FIGS. 10A to 10D.
Figure 10F:
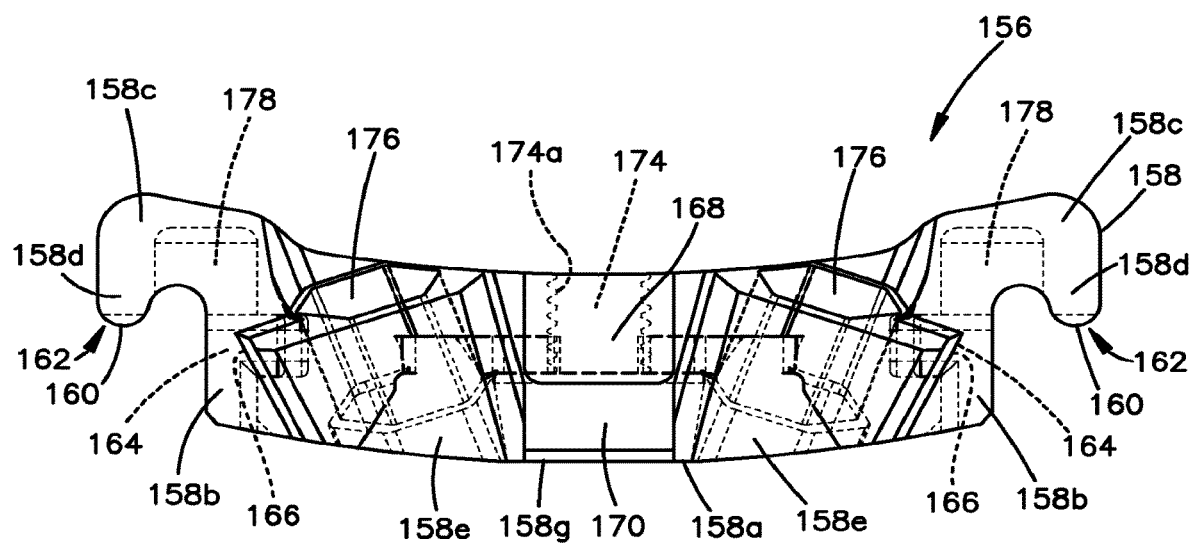
FIG. 10F is a top elevation view of the fixation plate illustrated in FIG. 10E.
Figure 10G:
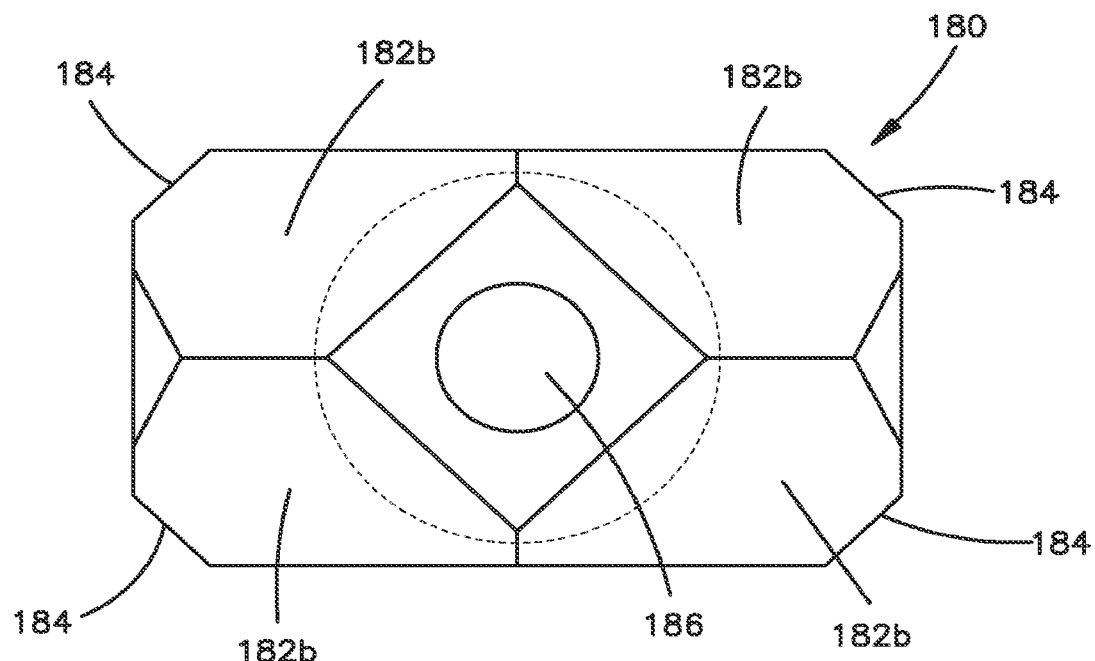
FIG. 10G is a front elevation view of a blocking plate for use with the fixation plate illustrated in FIGS. 10E and 10F.
Figure 10H:
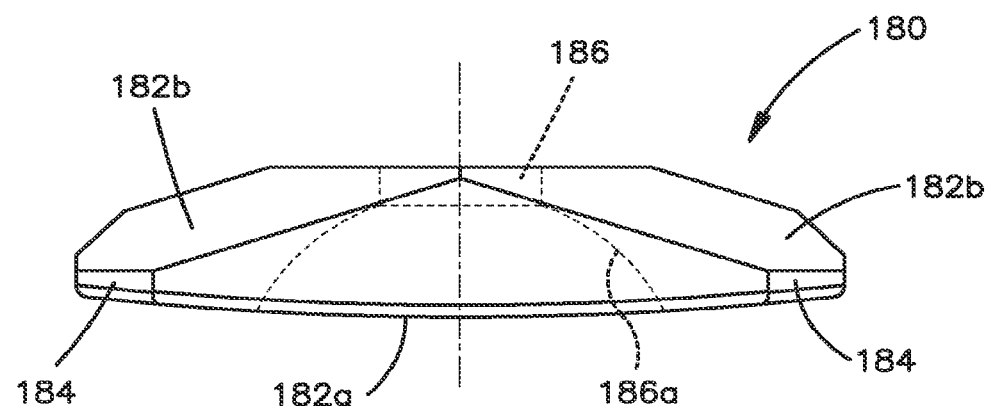
FIG. 10H is a top elevation view of the blocking plate illustrated in FIG. 10G.

The intervertebral implant 148 has a generally C-shaped footprint defined by a posterior side 148a, lateral sides 148b terminating in distal ends 148c opposite the posterior side 148a, an upper surface 148d, and a lower surface 148e opposite the upper surface. In an example embodiment, a portion of the posterior side 148a between the lateral sides 148b may be curved inwardly in a direction toward the distal ends 14c, as depicted in FIGS. 10A and 10B. In an alternative embodiment, a portion of the posterior side 148a between the lateral sides 148b may be curved outwardly in a direction away from the distal ends 148c (not shown). In another alternative embodiment, the posterior side 148a may be substantially straight between the lateral sides 148b, as depicted in FIGS. 10C and 10D. The posterior side 148a and lateral sides 148b define an open central bore 150, the shape of which substantially conforms to the footprint of the intervertebral implant 148. The central bore 150 can be filled with bone growth inducing substances to allow bony ingrowth and to assist in fusion between the intervertebral implant 148 and adjacent vertebral bodies.

In an example embodiment of the intervertebral implant 148, the upper and lower surfaces 148d and 148e may have gripping features such as teeth, spikes, or similar structures formed thereon and configured to facilitate gripping engagement between the upper and lower surfaces 148d and 148e and the end plates of adjacent vertebral bodies. The teeth may be pyramidal, saw toothed or other similar shapes. In alternative embodiments of the intervertebral implant 148, portions of and/or the entirety of the upper and lower surfaces 148d and 148e may be substantially smooth and devoid of any protrusions. Upper and lower edges 148f and 148g, defined where the upper and lower surfaces 148d and 148e intersect with the posterior and lateral sides 148a and 148b respectively around the perimeter of the intervertebral implant 148, may be rounded (not shown). In an example embodiment, the upper and lower edges 148f and 148g may be rounded using a uniform radius of curvature around the perimeter of the implant. In an alternative embodiment, the upper and lower edges 148f and 148g may be rounded using a non-uniform radius of curvature around the perimeter of the implant. Rounding upper and lower edges 148f and 148g may facilitate easier insertion of the intervertebral implant 148, for example by minimizing required distraction of the end plates of adjacent vertebral bodies.

In an example embodiment, the intervertebral implant 148 has a generally wedge-shaped side-view profile. This wedge shape is defined by a gradual increase in the height of the intervertebral implant 148 (as measured between the upper and lower surfaces 148d and 148e) extending outwardly in a direction away the posterior side 148a in the direction of the distal ends 148c. The intervertebral implant 148 has a generally constant height between lateral sides 148b. In alternative embodiments, the intervertebral implant 148 may have a gradual increase in height followed by a gradual decrease in height extending from one lateral side 148b to the other, and/or may have a generally constant height between the posterior sides 148a and the distal ends 148c, or may have convex and/or concave upper and lower surfaces 148d and 148e, thereby defining a gradual increase in height followed by a gradual decrease in height extending from the posterior side 148a to the distal ends 148c and from one lateral side 148b to the other.

Retaining grooves 152 may be formed within the distal ends 148c of the intervertebral implant 148, for example in a vertical direction substantially perpendicular to a horizontal midplane defined between the upper and lower surfaces 148d and 148e. The retaining grooves 152 may be configured to releasably engage complementary retaining ribs 160 of the fixation plate 156. The distal ends 148c may also have access grooves 154 formed therein between the upper and lower surfaces 148d and 148e. The access grooves 154 may be configured to align with complimentary access grooves 162 and/or 164 of the fixation plate 156, thereby defining an access cavity 168 for an engaging member of a delivery instrument when the intervertebral implant 148 and the fixation plate 156 are in an assembled configuration.

The fixation plate 156 is defined by a generally rectangular body 158 that includes an anterior side 158a and lateral sides 158b extending therefrom, the lateral sides 158b configured to engage with the retaining grooves 152 of the intervertebral implant 148. In an example embodiment, the lateral sided 158b are generally J-shaped, extending initially from opposite sides of the anterior side 158a in a direction perpendicular to and away from the anterior side 158a, and through curved sections 158c before returning in a direction perpendicular to and towards the anterior side 158a and terminating in distal ends 158d. It should be noted that this configuration for lateral sides 158b is merely an example, and any other geometry may be used as appropriate. Upper and lower edges of the anterior side 158a, defined where upper and lower surfaces 158e and 158f of the anterior side intersect with an anterior surface 158g of the anterior side, may be rounded (not shown). In an example embodiment, the upper and lower edges 158e and 158f may be rounded using a uniform radius of curvature. In an alternative embodiment, the upper and lower edges 158e and 158f may be rounded using a non-uniform radius of curvature. Rounding upper and lower edges 158e and 158f may facilitate easier insertion of the fixation plate 156, for example by minimizing required distraction of the end plates of adjacent vertebral bodies.

The lateral sides 158b may have retaining ribs 160 formed thereon at the distal ends 158d, the retaining ribs 160 configured to be releasably received within the retaining grooves 152 of the intervertebral implant 158. Access grooves 162 and 164 may be formed within the retaining ribs 160 and the lateral sides 158b, in the area where the lateral sides 158b interface with the anterior side 158a, respectively. The access grooves 162 and 164 may be configured to align with complimentary access grooves 154 of the intervertebral implant 148, thereby defining an access cavity 168 for receiving an engaging feature of a delivery instrument when the intervertebral implant 148 and the fixation plate 156 are in an assembled configuration. The access grooves 164 may have a retaining shelf 166 formed therein configured to engage with an engaging feature of a delivery instrument, for example the raised ribs 258d formed on the insertion rods 258 of the delivery instrument 278, described in greater detail below. The lateral sides 158b may also have bores 178 formed within the curved sections 158c, the apertures configured to receive, for example the distal engagement tips 258c of the insertion rods of 258 of the delivery instrument 278.

The anterior side 158a of the fixation plate 156 may have gripping grooves 168 formed within the upper and lower surfaces 158e and 158f of the anterior side 158a, the gripping grooves 168 configured to receive grasping arms of a delivery instrument. The gripping grooves 168 may have a gripping ridge 170 formed therein, the gripping ridge configured to be engaged by the complimentary grasping features formed at the ends of the grasping arms of the delivery instrument. The anterior side 158a of the fixation plate 156 may also have a recess 172 formed therein configured to receive additional components of the intervertebral implant system 100, for example a ratchet blade 188, a blocking plate 180, or the like. The anterior side 158a may also have a central bore 174 formed therethrough having an inner surface 174a with threads configured to engage complimentary threads of a locking screw 138. In an example embodiment, the central bore 174 may be formed within the recess 172.

The anterior side 158a of the fixation plate 156 may also have a plurality of arcuate grooves 176 formed therethrough configured to slidably receive the arcuate fixation members 12C and to define an insertion trajectory for each of the arcuate fixation members 12C. In an example embodiment, the arcuate grooves 176 may have a generally uniform cross sectional geometry configured to closely conform to the cross sectional geometry of the body 102 of the arcuate fixation member 12C between the head 106 and the distal end 102b. When an arcuate fixation member 12C is in a fully inserted position within a respective arcuate groove 176, the lower surface 106b of the head 106 will be engaged with the outer surface of the anterior side 158a of the fixation plate 156. Because the upper surface 106a of the head 106 will not be flush with the outer surface of the anterior side 158a of the fixation plate 156 in this configuration, it may be desirable to omit the blocking plate 180 and the locking screw 138. In an alternative embodiment, the arcuate grooves 176 have a recessed ledge formed therein in the area where the arcuate grooves 176 intersect with the outer surface of the anterior side 158a of the fixation plate 156, the recessed ledge being configured to receive the lower surface 106b of the head 106 when the arcuate fixation member 12C is in a fully inserted position, such that the upper surface 106a of the head 106 is substantially flush with the outer surface of the anterior side 158a of the fixation plate 156.

The arcuate grooves 176 may be disposed about the central bore 174 in any desired configuration and may define any insertion trajectories as appropriate. In the example embodiment depicted in FIGS. 10E, 10F, 10I and 10J, the arcuate grooves 176 are formed in opposing quadrants around the central bore 174, with two arcuate grooves 176 located near the upper surface 158e and defining two generally cranial insertion trajectories, and two arcuate grooves 176 located near the lower surface 158f and defining two generally caudal insertion trajectories. It should be noted that this configuration of arcuate groove 176 locations and arcuate fixation member 12C insertion trajectories is merely an example, and the scope of the instant disclosure should not be limited thereto.

The blocking plate 180 is defined by a generally rectangular body 182 with an anterior surface 182a, and a plurality of angled posterior surfaces 182b generally opposite the anterior surface 182a. The body 182 may have an aperture 186 formed therethrough In an example embodiment, the diameter of the aperture may be slightly larger than the diameter of the central bore 174 of the fixation plate 156, such that a locking screw 138 may be inserted into the aperture with no interference therebetween. In another embodiment, the diameter of the aperture 186 may be substantially the same as that of the central bore 174, and the inner surface of the aperture may have threads formed thereon, the threads configured to engage complimentary threads of the locking screw 138. The aperture 186 may further be defined by a concave recess 186a formed within the anterior surface 182a, the concave recess 186a configured to receive the convex head 142 of the locking screw 138. The height, width, and depth of the body 182 may be proportioned so that the blocking plate 180 will be received within the recess 172 of the fixation plate 156, such that the anterior surface 182a of the body 182 is substantially flush with the anterior surface 158g of the anterior side 158a of the fixation plate 156 when the fixation plate 156 and the blocking plate 180 are in an assembled configuration. The anterior surface 182a of the body 182 may be generally planar, or may be defined to match the outer surface of the anterior side 158a of the fixation plate 156 when the blocking plate 180 and the fixation plate 156 are in a fully assembled configuration.

In an example embodiment wherein the blocking plate 180 and locking screw 138 are installed after the intervertebral implant 148 and fixation plate 156 have been inserted into an intervertebral space and the arcuate fixation members 12C driven into their fully inserted positions, the angled posterior surfaces 182b and chamfered corners 184 of the blocking plate 180 may be configured to engage the heads 106 of the arcuate fixation members 12C within the recess 172 of the fixation plate 156 when the blocking plate 180 is installed followed by the locking screw 138. When final tightening of the locking screw 138 is performed, the blocking plate 180 may rigidly fix the arcuate fixation members 12C in position, and additionally prevent pullout of the arcuate fixation members 12C.

In another example embodiment wherein the intervertebral implant 148, the fixation plate 156, the blocking plate 180, and the locking screw 138 are pre-assembled, but not finally tightened, and then inserted into an intervertebral space before the arcuate fixation members 12C are inserted and driven into position, the angled posterior surfaces 182b and chamfered corners 184 of the blocking plate 180 may be configured to allow the arcuate fixation members 12C to be inserted and driven into position with the blocking plate 180 and the locking screw 138 in place. In this embodiment, the angled posterior surfaces 182b may have wedge features formed thereon (not shown), the wedge features configured to interfere between the heads 106 of the arcuate fixation members and the surrounding structure of the fixation plate 156, for example by applying outward force laterally upward and downward on the arcuate fixation members 12C to lock them in place when final tightening is applied to the locking screw, and additionally to prevent pullout of the arcuate fixation members 12C.

Referring now to FIG. 10J, an example embodiment of the intervertebral implant system 100 in a completely assembled configuration outside of an intervertebral space is illustrated. The fixation plate 156 has been engaged with the intervertebral implant 148 such that the retaining ribs of the fixation plate 156 are seated with the retaining grooves of the intervertebral implant 148. Four arcuate fixation members 12C have been inserted through corresponding arcuate grooves within the fixation plate 156, and have been driven to a fully inserted position. The blocking plate 180 and the locking screw 138 have been installed and finally tightened.

It should be noted that although the description and accompanying figures illustrating the intervertebral implant system 100 included herein depict example embodiments of the intervertebral implant system 100 that include four arcuate fixation members 12C, with two of the four arcuate fixation members 12C having a generally cranial insertion trajectory and the remaining two arcuate fixation members having a generally caudal insertion trajectory, other configurations of the intervertebral implant system 100 using more or less arcuate fixation members 12C and/or varying insertion trajectories are possible and intended to be included within the scope of the instant disclosure. For example, in an alternative embodiment of the intervertebral implant system 100, the fixation plate 116 may have three arcuate grooves 128 formed therein having any desirable placement and/or insertion trajectory with respect to the central bore 126 (e.g., with two of the three arcuate fixation members 12C having a generally caudal insertion trajectory and the remaining arcuate fixation member 12C having a generally cranial insertion trajectory, or with two of the three arcuate fixation members 12C having a generally cranial insertion trajectory and the remaining arcuate fixation member 12C having a generally caudal insertion trajectory). The intervertebral implant 108 may of course have matching grooves 112 formed therein. Such alternative embodiments with two arcuate fixation members 12C having one of a generally cranial or caudal trajectory and a third arcuate fixation member having the opposite general trajectory may allow for the stacking of two or more assembled configurations of the intervertebral implant system 100 in place of adjacent vertebral bodies removed from an intervertebral space. Additionally, while the arcuate fixation members 12C illustrated in the various figures herein generally have divergent insertion trajectories with respect to each other, fixation plates 116 and/or 156 may also be configured so that one or more of the arcuate fixation members 12C will have convergent insertion trajectories with respect to each other, or similar insertion trajectories (e.g., laterally towards a common side). For example, arcuate fixation members with generally cranial insertion trajectories may converge toward one another, may diverge away from one another, or may both follow similar insertion trajectories, while arcuate fixation members with generally caudal insertion trajectories may converge toward one another, may diverge away from one another, or may both follow similar insertion trajectories. Any combination of the above insertion trajectory configurations may be used as appropriate.

Referring now to FIGS. 11A to 11H, and FIGS. 12A to 12C, example embodiments of additional features for securing the arcuate fixation members 12C within assembled configurations of the intervertebral implant system 100 are illustrated. Referring first to FIGS. 11A to 11H, an example embodiment using ratcheting features to secure the arcuate fixation members 12C is illustrated. In an example embodiment, an intervertebral implant 148 (not shown), a fixation plate 156, and a locking screw 138 can be used in combination with a ratchet plate 188 configured to be received within the fixation plate 156 and fixed in place with the locking screw 138. The ratchet plate 188 is defined by a body 190 defining an anterior surface 190a and a posterior surface 190b opposite the anterior surface.

The body 190 includes a plurality of blades 192 extending outwardly therefrom, each blade 192 defining a proximal end 192a where the blade 192 extends from the body 190, and a distal end 192b opposite the proximal end 192a. In an example embodiment, the blades 192 may be curved between the proximal and distal ends 192a and 192b. The blades 192 may be curved along a generally constant radius of curvature, may be curved along a non-uniform radius of curvature, or any combination thereof. In an alternative embodiment, the blades may be substantially straight between the proximal and distal ends 192a and 192b. The blades may configured to be of a length such that the distal ends 192b of the blades 192 are disposed within the arcuate grooves 176 of the fixation plate 156 when the ratchet plate 188 is inserted into the recess 172 of the fixation plate 156 in an assembled configuration. It should be noted that while the ratchet plate 188 is depicted within the attached figures as having four blades 192, this number of blades 192 is only an example configuration, and the scope of the instant disclosure should not be limited thereto. For example, alternative embodiments of the ratchet blade having more or less than four blades 192 are possible and intended to be included within the scope of the instant disclosure.

The distal ends 192b of the blades 192 may have tips 194 defined thereon, the tips 194 configured to lockingly engage with a complimentary engaging feature, for example a ratchet tooth 198, defined on an arcuate fixation member 12C. The body 190 may have an aperture 196 formed therethrough. In an example embodiment, the diameter of the aperture may be slightly larger than the diameter of the central bore 174 of the fixation plate 156, such that a locking screw 138 may be inserted into the aperture with no interference therebetween. In another embodiment, the diameter of the aperture 196 may be substantially the same as that of the central bore 174, and the inner surface of the aperture may have threads formed thereon, the threads configured to engage complimentary threads of the locking screw 138. The aperture 196 may further be defined by a concave recess 196a formed within the anterior surface 190a, the concave recess 196a configured to receive the convex head 142 of the locking screw 138.

Referring now to FIG. 11D, an example embodiment of an arcuate fixation member 12C configured for use with the ratchet plate 188 is illustrated. A series of ratchet teeth 198 are defined on the body 102 of the arcuate fixation member 12C. The ratchet teeth 198 may be defined in the area of the proximal end 102a of the body, near the head 106. The ratchet teeth 198 may be formed from triangular grooves formed within the body 102 of the arcuate fixation member, or may be formed on or in the body 102 using any other tooth geometry as appropriate. It should be noted that while the arcuate fixation member 12C depicted in FIGS. 11D to 11H has four ratchet teeth 198 formed thereon, this number of ratchet teeth is only an example, and the scope of the instant disclosure should not be limited thereto.

Figure 11A:
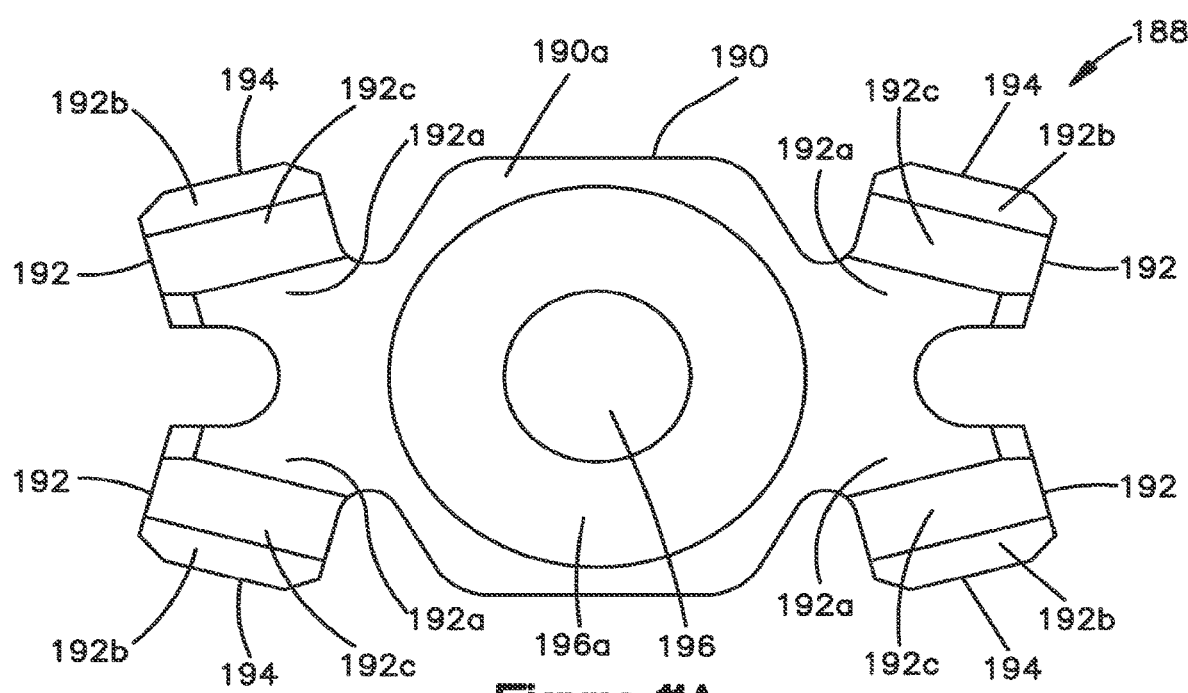
FIG. 11A is a front elevation view of a ratchet plate for use with the fixation plate illustrated in FIGS. 10E and 10F.
Figure 11B:
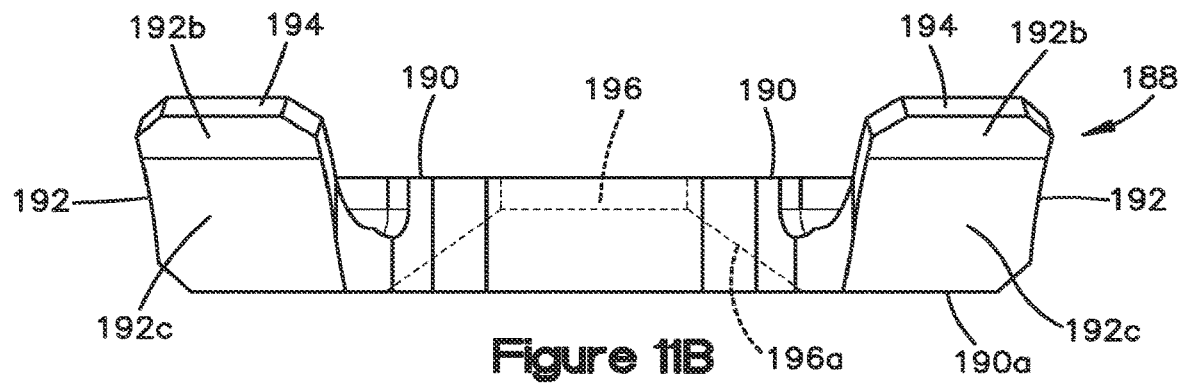
FIG. 11B is a top elevation view of the ratchet plate illustrated in FIG. 11A.
Figure 11C:
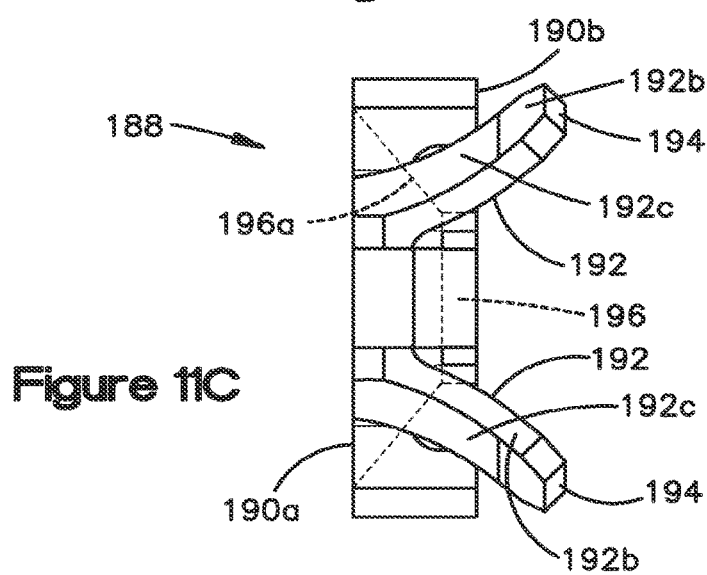
FIG. 11C is a side elevation view of the ratchet plate illustrated if FIG. 11A.
Figure 11H:
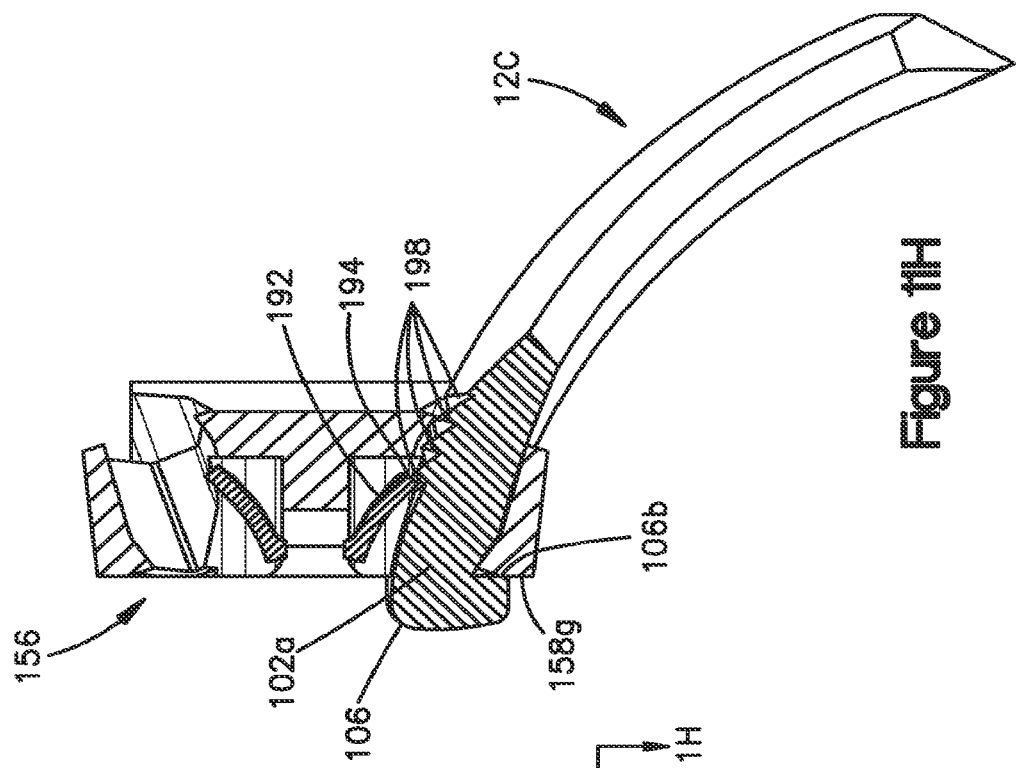
FIGS. 11G and 11H illustrate a side elevation cross sectional view of the assembly illustrated in FIG. 11E.
Figure 11G:
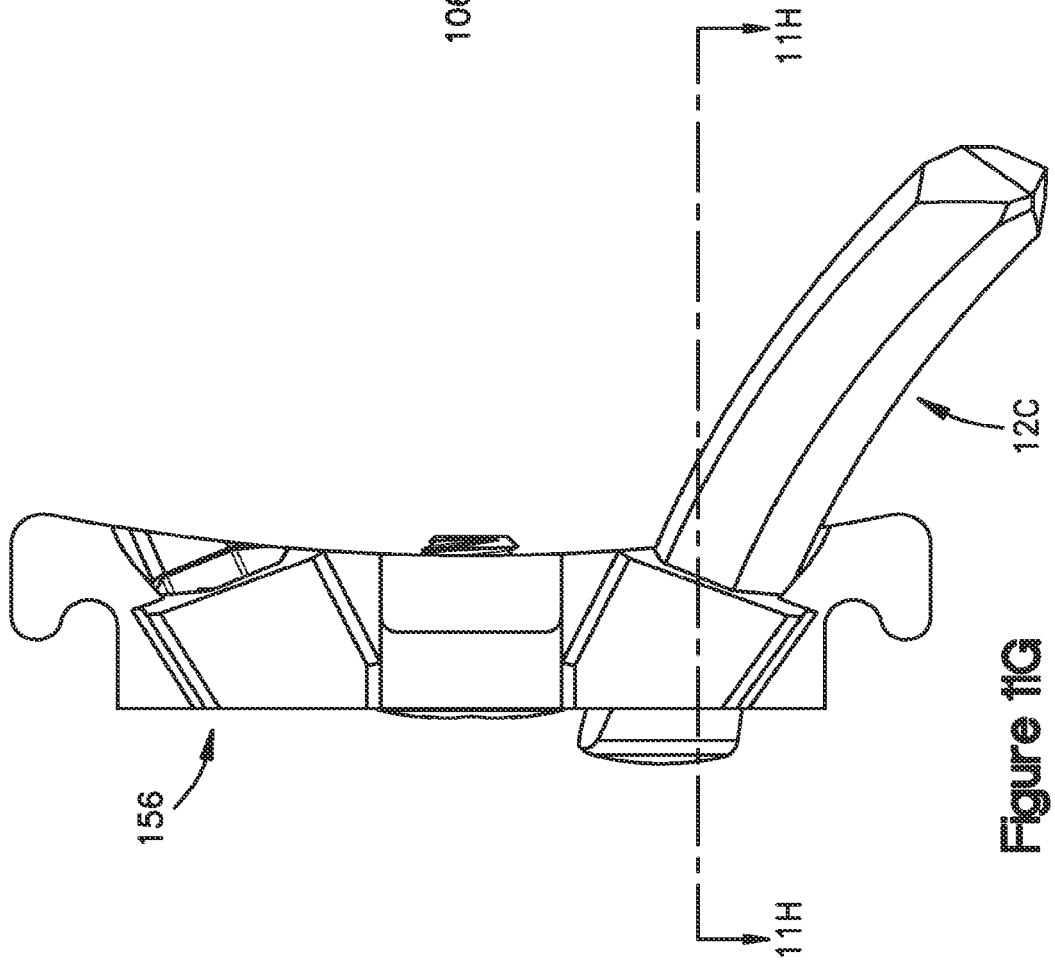

Referring now to FIGS. 11F to 11H, an example embodiment of the intervertebral implant system 100 in a partially assembled configuration including a single arcuate fixation member 12C and omitting the intervertebral implant 148 is illustrated. The ratchet plate 188 has been nested within the fixation plate 156 and anchored in place with the locking screw 138. A single arcuate fixation member 12C has been inserted through a corresponding arcuate groove within the fixation plate 156, and has been driven to a fully inserted and locked position. FIGS. 11G and 11H illustrate a cross sectional view of the partially assembled intervertebral implant system 100. The arcuate fixation member 12C has been driven into place such that each successive ratchet tooth 198 has passed over the tip 194 of the blade 192 until the arcuate fixation member 12C arrived in a fully inserted and locked position. The tip 194 of the blade 192 is firmly seated against the ratchet tooth 198 nearest the proximal end 102a of the body 102 of the arcuate fixation member 12C, thereby engaging the lower surface 106b of the head 106 of the arcuate fixation member 12C against the anterior surface 158g of the fixation plate 156 in a fixed and locked configuration.

Referring now to FIGS. 12A to 12D, an example embodiment for securing an arcuate fixation member 12C of the intervertebral implant system 100 with a screw 202 is illustrated. A plurality of helical threads 200 are defined within the body 102 of the arcuate fixation member 12C, the threads 200 configured to engage complimentary threads of the screw 202. The threads 200 may be defined within the area of the proximal end 102a of the body 102, near the head 106. In an example embodiment, the threads 200 may define tapered threads 200a that transition into constant radius threads 200b. The radius of the tapered threads 200a may decrease as the tapered threads 200a extend in a direction downward and perpendicular from the proximal end 102a of the body 102 until the tapered threads 200a transition into the constant radius threads 200b.

The screw 202 includes a shaft 204 that defines longitudinally opposing proximal and distal ends 204a and 204b, respectively. A plurality of helical tapered threads 204c may extend along the shaft 204 in a direction toward the distal end 204b. The outer diameter of the tapered threads 204c may decrease with distance from the proximal end 204a until the tapered threads 204c transition into a series of constant radius threads 204d. The constant radius threads 204d may extend along the remainder of the shaft 204 to the distal end 204b. The tapered and constant radius threads 204c and 204d may be configured to be complimentary to the tapered and constant radius threads 200a and 200b of the arcuate fixation member 12C. In an alternative embodiment, the threads 200 defined within the body 102 and the threads defined on the shaft 204 of the screw 202 may be of constant radius. It should be noted that although the screw 202 is depicted in FIGS. 12A to 12D as a set-type screw, that any appropriate screw-type anchor may be utilized.

Figure 12A:
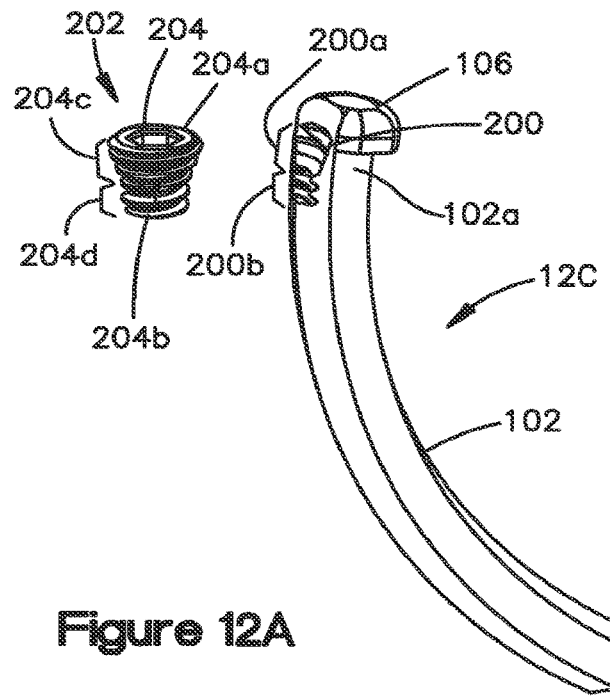
FIG. 12A is a perspective view of an arcuate fixation member and a complimentary screw constructed in accordance with another embodiment.
Figure 12B:
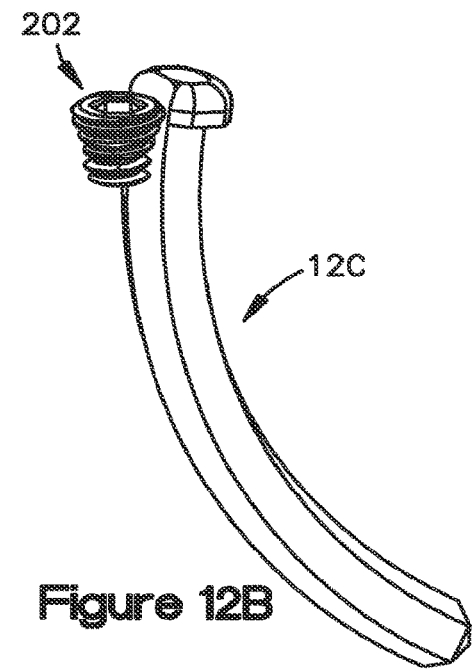
FIG. 12B is a perspective view of the arcuate fixation member and the complimentary screw in a mated configuration.
Figure 12D:
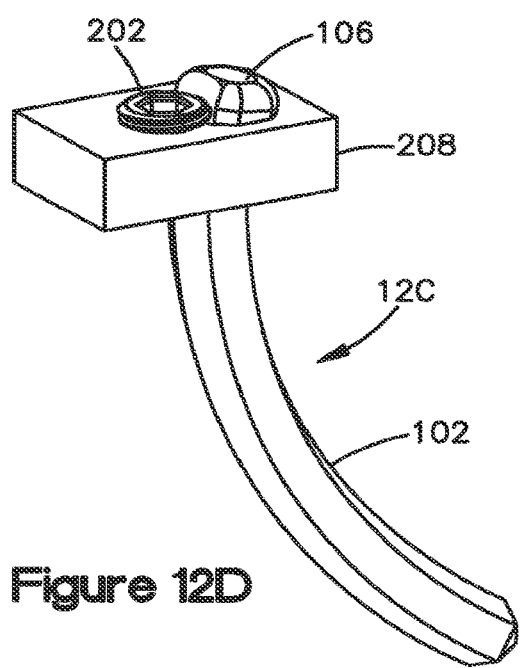
FIG. 12D is a perspective view of an assembly utilizing the components illustrated in FIGS. 12A to 12C.
Figure 12C:
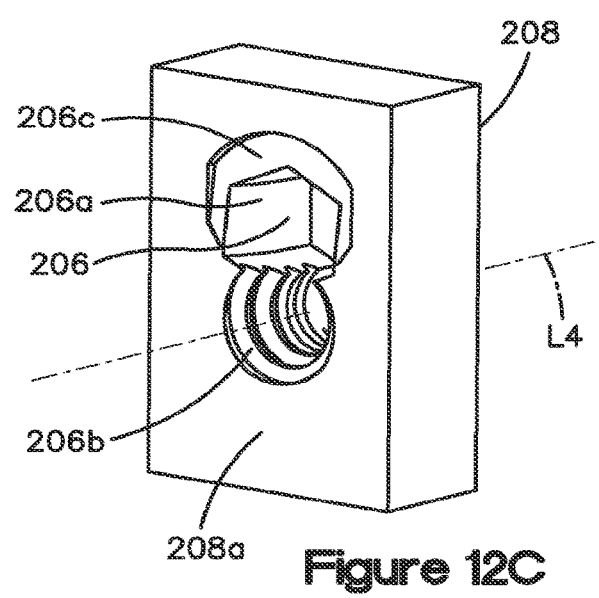
FIG. 12C is a perspective view of an arcuate groove configured to receive the components illustrated in FIGS. 12A and 12B.

When deployed in combination with the fixation plate 156, one or more of the arcuate grooves 176 may be replaced with a threaded arcuate groove 206. For the sake of simplicity, the threaded arcuate groove 206 is illustrated in FIGS. 12C and 12D as defined within block 208, rather than in the fixation plate 156. The threaded arcuate groove 206 includes an arcuate groove 206a configured to receive the arcuate fixation member 12C, and a threaded aperture 206b formed adjacent to the arcuate groove 206a and configured to guide a screw type fastener along a longitudinal axis L4. It should be noted that although the threaded aperture 206b is depicted as being formed to define the longitudinal axis L4 in a direction generally perpendicular to an outer surface 208a of the block 208, the threaded aperture 206b may be formed to define the longitudinal axis L4 in any direction appropriate for insertion of a screw type fastener. A head recess 206c may be formed within the threaded arcuate groove 206 in the area where the threaded arcuate groove 206 meets the outer surface 208a of the block 208, the head recess 206c configured to receive at least a portion of the head 106 of the arcuate fixation member 12C.

In the assembled configuration depicted in FIG. 12D, the arcuate fixation member 12C has been inserted into the arcuate groove 206a and driven to a fully inserted position. The screw 202 has been driven into an almost fully driven position in the threaded aperture 206b. As the screw 202 is finally tightened, the tapered threads 204c will engage the complimentary tapered threads 200a of the arcuate fixation member 12C, causing the arcuate fixation member 12C to be locked into its fully inserted position as the screw 202 is tightened. In the finally tightened position, the engagement of the tapered threads 204c of the screw 202 with the arcuate fixation member 12C and the threaded aperture 206b will secure the assembly in place and prevent pullout of the arcuate fixation member 12C. In an alternative embodiment, the arcuate fixation member 12C is driven to an almost fully inserted position, and as the screw 202 is finally tightened, the tapered threads 204c will engage the complimentary tapered threads 200a of the arcuate fixation member 12C, causing the arcuate fixation member 12C to be driven into its fully inserted position and locked with the screw and the threaded aperture 206b. In example embodiments utilizing a bone screw (not shown) in combination with the arcuate fixation member 12C, the bone screw may be inserted, for example along a trajectory that varies from that of the insertion trajectory of the arcuate fixation member 12C, such that as the bone screw is driven into its fully driven position within the underlying structure or bone, tapered threads on the bone screw interface with complimentary tapered threads 200a of the arcuate fixation member 12C and the threaded aperture 206b, thereby locking the arcuate fixation member 12C and the bone screw together in their finally assembled position within the threaded aperture 206b.

In another alternative embodiment (not shown) for securing the arcuate fixation members 12C within the intervertebral implant system 100, a captive screw is secured within the central bores 126 or 174 of respective fixation plates 116 or 156. The captive screw is configured to be retained within its respective central bore, but be freely rotatable therein, such that the end of the captive screw nearest the outermost anterior surface of the respective fixation plate is exposed. The captive screw has engagement features formed within its exposed end for engaging a delivery instrument, and helical threads formed radially along its outer surface, the helical threads configured to engage with a plurality of complimentary helical threads 200 defined within the body 102 of the arcuate fixation member 12C along a substantial length of the body 102 between its proximal and distal ends 102a and 102b respectively. An arcuate fixation member 12C may be loaded tip first into an arcuate groove 128 or 176 of the respective fixation plates 116 or 156, such that the threads 200 near the distal end 102b of the body 102 of the arcuate fixation member engage with the helical threads formed on the outer surface of the captive screw. As rotational force is applied to the captive screw by a delivery instrument, the force is transferred to the arcuate fixation member 12C via the engaged complimentary threads, causing the arcuate fixation member to be driven into underlying structure or bone. A plurality of arcuate fixation members may be so loaded into assemblies comprising respective intervertebral implants and fixation plates before those assemblies are inserted into an intervertebral space. The assemblies may then be guided into position in an intervertebral space by a delivery instrument. Once in position, the delivery instrument may engage the captive screw and apply a rotational force thereto, thereby driving the plurality of arcuate fixation members into fully inserted positions within adjacent vertebral bodies. The captive screw may also lock the arcuate fixation members 12C into position within the respective fixation plates during final tightening of the captive screw.

Now referring to FIGS. 13A to 13F and 14A to 14E, example embodiments of delivery instruments for use in inserting intervertebral implant assemblies constructed using components of the intervertebral implant system 100 into intervertebral spaces and/or driving the arcuate fixation members 12C of the intervertebral implant system 100 are illustrated.

As illustrated in FIGS. 13A to 13F, delivery instrument 208 includes a shaft 210 that defines longitudinally opposing proximal and distal ends 210a and 210b. The distal end 210b of the shaft 210 may have helical threads 212 formed thereon, the threads 212 configured to be received in the central bore 126 of the fixation plate 116. The proximal end 210a may have helical threads 214 formed thereon, the threads 214 configured to engage complimentary threads of an accessory (not shown). Accessories may be configured to facilitate easier use of the delivery instrument 208 in positioning and/or insertion of an intervertebral implant assembly into an intervertebral space, and may include a "pistol" grip, a handle, a slap hammer, a slide hammer, or the like. In an alternative embodiment, the proximal end 210a of the shaft 210 may have gripping features (not shown) formed directly thereon, the gripping features configured to enable the proximal end 210a of the shaft 210 to act as a handle.

Delivery instrument 208 may further include a pivot block 216 having a generally channel-shaped body 218 defined by an anterior side 218a, an upper side 218b, and a lower side 218c opposite the upper side. The anterior side 218a of the body 218 may have an aperture 218d formed therethrough, the aperture enabling the pivot block 216 to be carried on the shaft 210. In an example embodiment, the pivot block 216 may be fixed in position on the shaft 210. In alternative embodiments, the pivot block 216 may be free to rotate about a longitudinal axis of the shaft, free to translate in an anterior and/or posterior direction along the shaft 210, may be releasably lockable to the shaft 210 between the proximal and distal ends 210a and 210b, or any combination thereof. The upper and lower sides 218b and 218c may define a channel 222 through the body between the opposing ends 218e of the body 218. The upper and lower sides 218b and 218c may each have a pair of raised tabs 220 formed thereon at opposing ends 218e of the body, such that the tabs on the upper and lower sides 218b and 218c directly oppose each other, and are configured to receive a pair of lateral arms 224, one at each of the opposing ends 218e of the body 218.

The lateral arms 224 each include a proximal end 224a and a distal end 224b opposite the proximal end. The distal ends 224b of each of the lateral arms may have an engagement feature 226 formed thereon, the engagement feature 226 configured to engage a complementary engagement feature formed within the fixation plate 116. In an example embodiment, the distal end 224b of each lateral arm 224 may have a raised rib engagement feature 226 formed thereon, the raised rib configured to be inserted into a respective aperture 122 of the fixation plate 116, and to releasably grip a corresponding retaining rib 124. It should be noted that a raised rib is merely an example engagement feature 226, and the scope of the instant disclosure should not be limited thereto. The proximal ends 224a of each of the lateral arms 224 may be configured to be received within the tabs 220 at the opposing ends 218e of the body 218. The tabs 220 and the proximal ends 224a of each of the lateral arms 224 may have apertures 228 formed therethrough, the apertures 228 configured to receive a joint connector 230. The joint connector 230 may be a pin, an axle, a rivet, or any other appropriate connector.

With the proximal ends 224a of each of the lateral arms 224 seated between respective opposing tabs 220 and with the joint connectors 230 inserted into the apertures 228, the lateral arms 224 become configured to pivot about the joint connectors 230, allowing the distal ends 224b of the lateral arms to move in a grabbing motion, such that the distal ends 224b can releasably grip the fixation plate 116. The lateral arms 224 may be configured to be simultaneously pivoted, for example through attachment to a common actuator (not shown). The proximal ends 224a of the lateral arms may be configured with locking features configured to engage with complimentary features of the pivot block 216, to enable the lateral arms 224 to be releasably locked in a gripping position. For example, the locking features may comprise a series of ratchet teeth may be formed on rounded end surface 224c of each of the lateral arms, the ratchet teeth configured to engage with a complimentary ratcheting mechanism of the pivot block 216.

Delivery instrument 208 may further include a guide ring 232 and/or a drive head 236 configured to deliver one or more arcuate fixation members 12C for insertion. The guide ring 232 and/or the drive head 236 may also be configured to be carried on the shaft 210, preferably between the distal end 210b of the shaft 210 and the pivot block 216. The guide ring 232 includes an annular body 234 defining a posterior surface 234a and an anterior surface 234b opposite the posterior surface. The annular body 234 may have a plurality of arcuate grooves 234d formed along an inner surface 234c of the annular body 234, the arcuate grooves 234d configured to receive a plurality of arcuate fixation members 12C and to align the arcuate fixation members with corresponding arcuate grooves of a fixation plate.

The drive head 236 includes a body 238 defined by an anterior surface 238a, a posterior surface 238b opposite the anterior surface, lateral surfaces 238c, and upper and lower surfaces 238d and 238e respectively. The body 238 may have a central bore 238f formed therethrough, such that the body 238 may be slidably carried on the shaft 210. The drive head 236 may further include a shaft 240 having longitudinally defined proximal and distal ends 240a and 240b respectively. The entirety of the shaft 240 may be cannulated, the cannulation defining an inner diameter substantially matching the diameter of the central bore 238f, such that the shaft 240 may be slidably carried on the shaft 210. The distal end 240b of the shaft 240 may be coupled to the anterior surface 238a of the body 238.

The posterior surface 238b of the drive head may have a substantially concave outer ring 242 formed therein, the concave outer ring encompassing a substantially convex inner dome 244. The concave outer ring 242 and the convex inner dome 244 are configured to drive the plurality of arcuate fixation members 12C as the drive head 236 travels along the shaft 210 in a direction toward the distal end 210b. In an example pre-insertion configuration, the plurality of arcuate fixation members 12C may be loaded into the guide ring 232 and the drive head 236 positioned such that the concave outer ring 242 is engaged with the heads 206 of the arcuate fixation members 12C. As the drive head 236 is advanced towards the distal end 210b of the shaft 210, the arcuate fixation members 12C are driven into respective vertebral bodies. As the arcuate fixation members 12C are driven, the heads 106 of the arcuate fixation members 12C travel inwardly along the concave outer ring 242 in a direction generally towards the shaft 210, and from the concave outer ring 242 onto the convex inner dome 244. The convex inner dome 244 may deliver the arcuate fixation members 12C into their fully inserted positions. The guide ring 232 may be removed from the shaft 210 for the final portion of the driving process. It should be noted that while the example drive head 236 depicted in FIGS. 13C to 13E and described herein is configured to simultaneously drive four arcuate fixation members 12C, other configurations are possible and intended to be within the scope of the instant disclosure. For example, by adjusting the geometry of the posterior surface 238b of the drive head 236, the drive head could be configured to simultaneously drive more or less than four arcuate fixation members 12C, to stagger the driving of one or more arcuate fixation members 12C, to distract one or more arcuate fixation members 12C, or any combination thereof.

In an example method of using the delivery instrument 208 to insert and secure an example assembly of the intervertebral implant system 100, an intervertebral implant 108 may be nested an engaged within a fixation plate 116 to create an implant assembly. The intervertebral implant 108 may be packed, for example with bone growth inducing substances, as appropriate. The distal ends 224b of the lateral arms 224 may be positioned to grip the fixation plate 116 and the lateral arms 224 may be locked in the gripping position. A plurality of arcuate fixation members 12C may be loaded into the guide ring 232 and the drive head 236 moved into position to drive the arcuate fixation members 12C. The delivery instrument 208 may then be used to position and insert the implant assembly into an intervertebral space. When the implant assembly has been positioned, the arcuate fixation members may be driven into position. The implant insertion process may be completed with the installation of a blocking plate 132 and a final tightening of a locking screw 138.

Figure 13A:
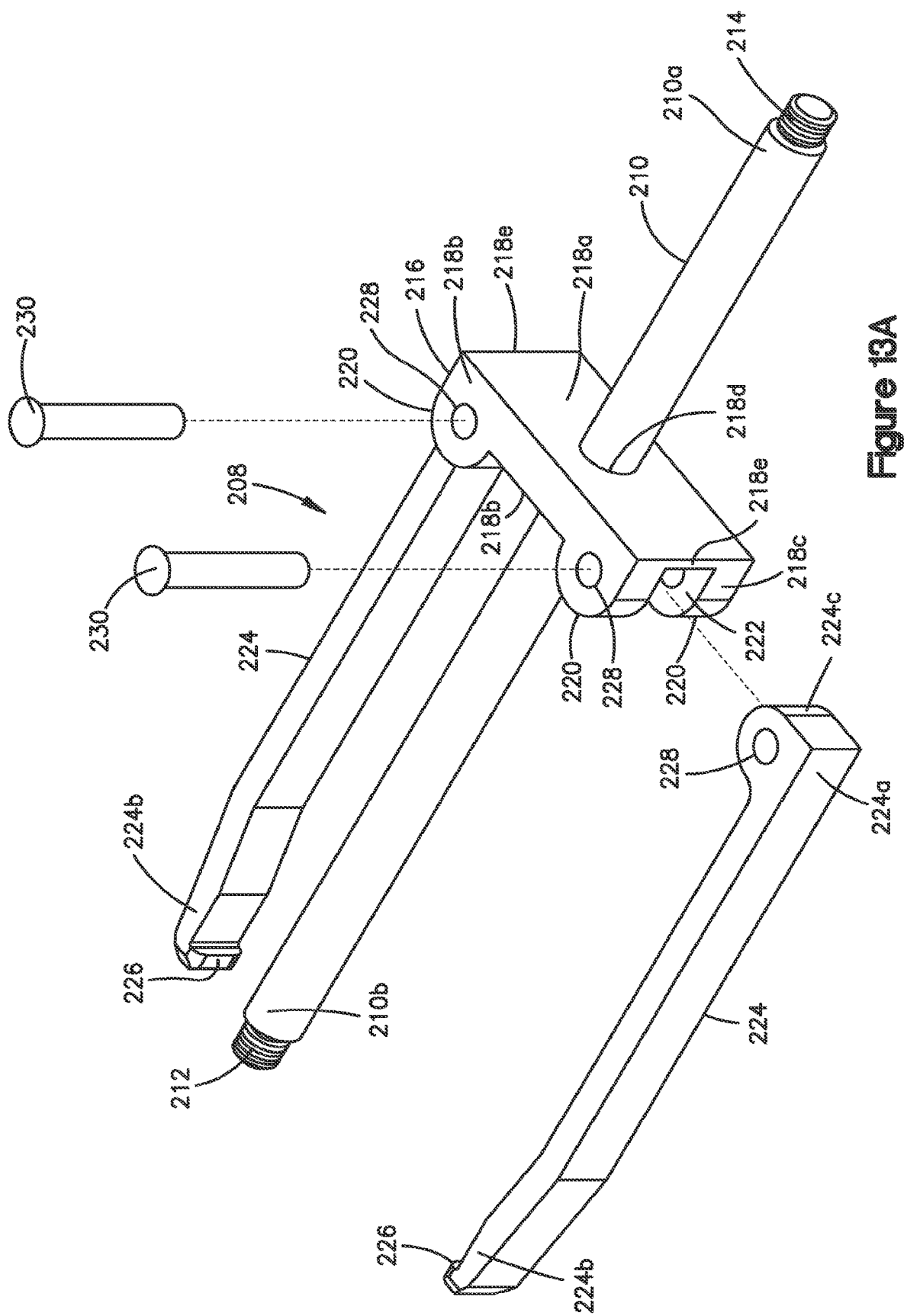
FIG. 13A is an exploded view of an assembled components of an embodiment of a delivery instrument.
Figure 13C:
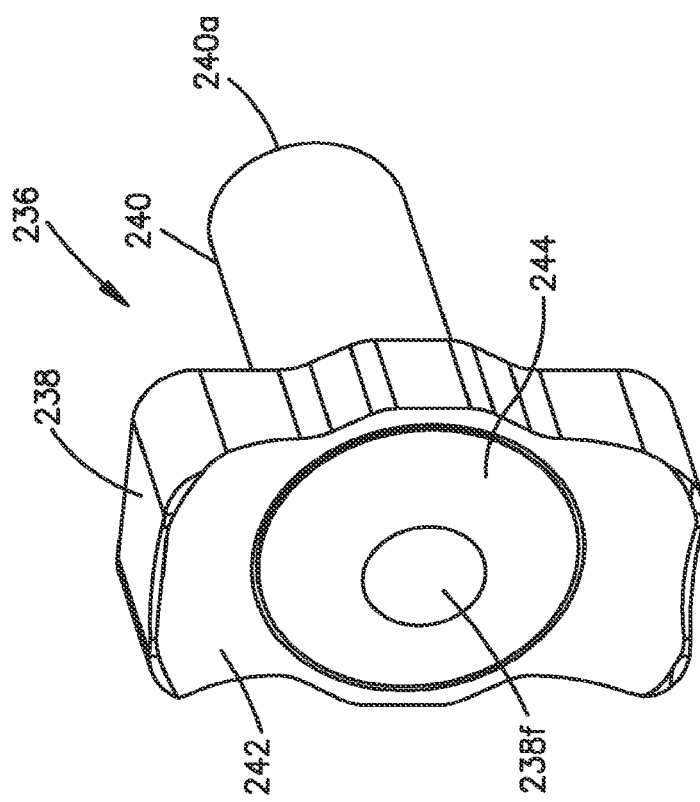
FIG. 13C is a perspective view of an embodiment of a drive head for use with the components illustrated in FIG. 13A
Figure 13B:
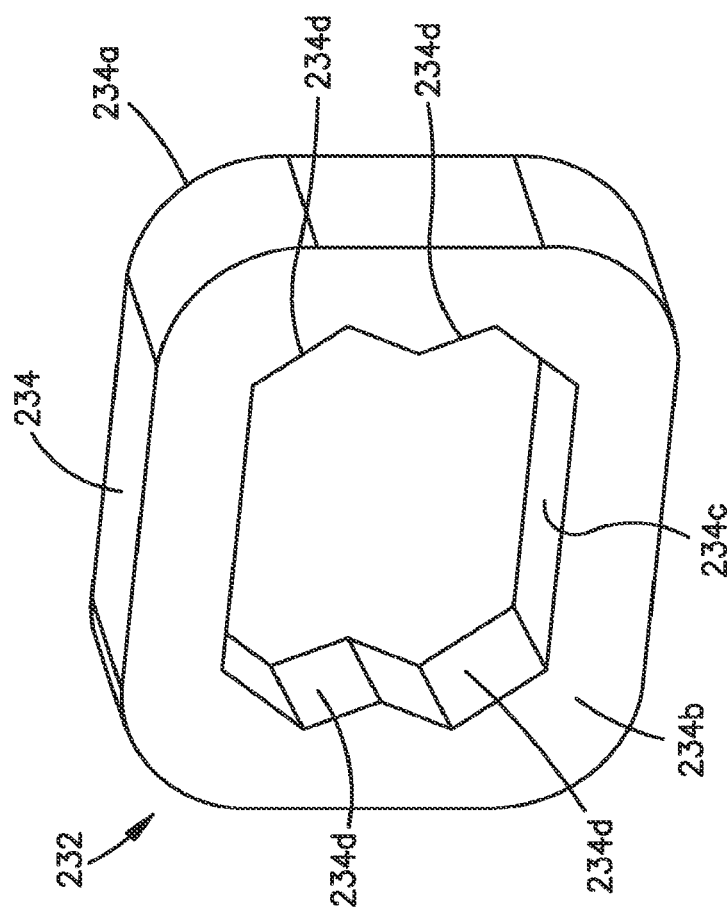
FIG. 13B is a perspective view of an embodiment of a guide ring for use with the components illustrated in FIG. 13A.
Figure 13D:
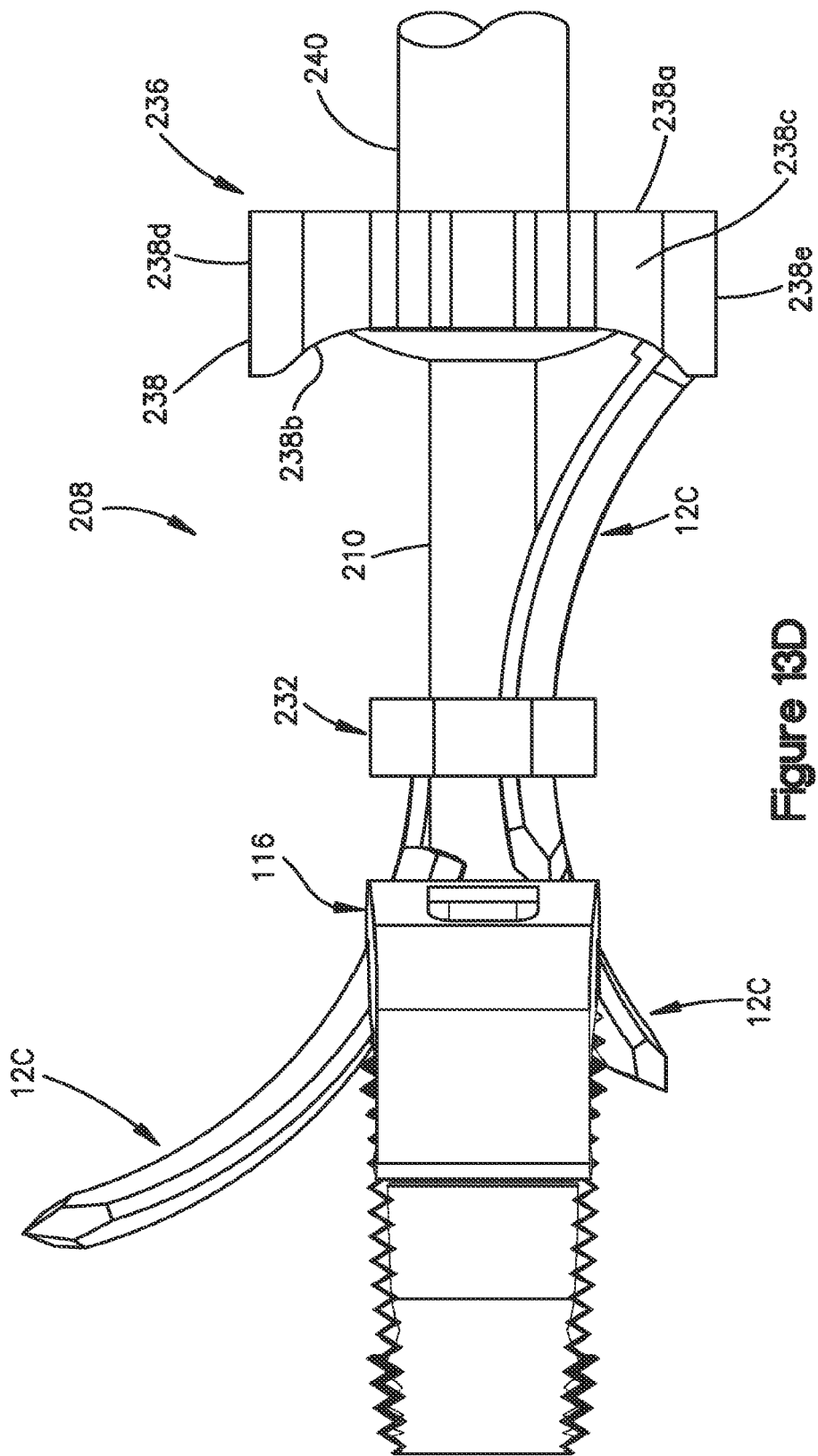
FIG. 13D is a side elevation view of an assembly utilizing components illustrated in FIGS. 13A to 13C in combination with the assembly illustrated in FIG. 9L.
Figure 13E:
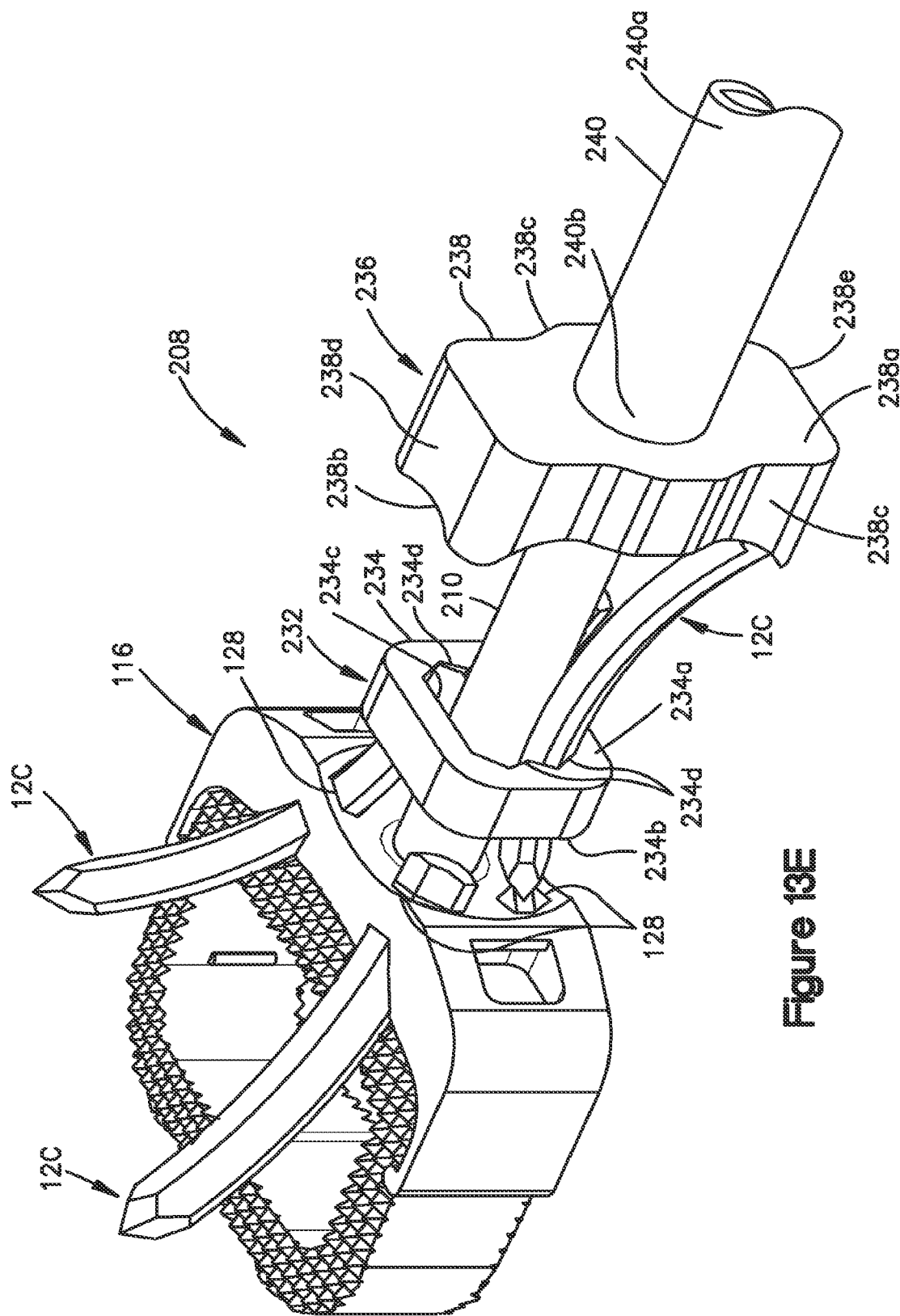
FIG. 13E is a perspective view of the assembly illustrated in FIG. 13D.
Figure 13F:
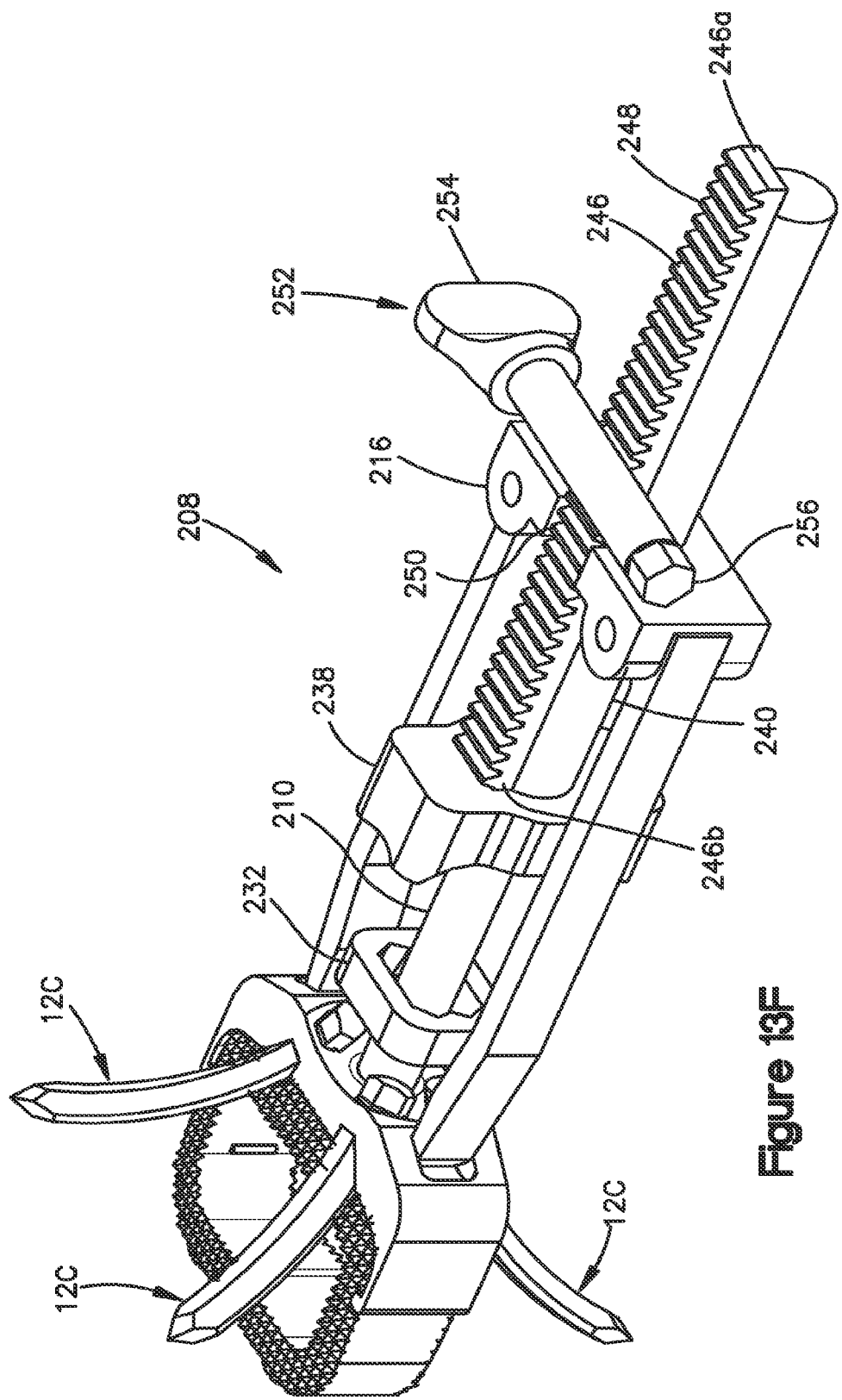
FIG. 13F is a perspective view of another embodiment of the delivery instrument illustrated in FIGS. 13A to 13E.

Various techniques may be utilized to actuate the drive head 236, thereby causing it to drive one or more arcuate fixation members 12C into position. In an example embodiment, the drive head 236 may be advanced towards the distal end 210b of the shaft 210 by a series of impaction forces applied to the drive head 236. The impaction forces may be applied manually, for example by a surgeon via the use of a mallet, or mechanically, for example by a successive series of impactional strikes from a sonic hammer. In an alternative embodiment, the drive head 236 may be advanced via a mechanical drive system. For example, a rack and pinion system may be employed, as illustrated in FIG. 13F. A rack 246 includes a proximal end 246a and a distal end 246b opposite the proximal end, the distal end 246b coupled to the drive head body 238 and/or the shaft 240. The rack may have a series of teeth 248 defined thereon between the proximal and distal ends 246a and 246b. The pivot block 216 may have a guide channel 250 formed within the upper side 218b of the body 218, the guide channel 250 configured to slidably receive the rack 246 therein. A pinion drive 252 may be coupled to the pivot block 216, for example on the anterior side 218a of the body 218, such that one or more pinion gears (not shown) of the pinion drive 252 engage the teeth 248 of the rack 246. The pinion drive 252 may be configured with a manual actuator 254 and/or an adapter 256, the adapter 256 configured to couple with a motorized source of rotational force. When the pinion drive 252 is actuated, via either the manual actuator 254 and/or a rotational force applied via the adapter 256, the rack 246, and consequently the drive head 236, may be translated in a direction toward the distal end 210b of the shaft 210, such that the arcuate fixation members 12C are driven into position.

Referring now to FIGS. 14A-14E, delivery instrument 278 includes a pair of insertion rods 258, each defining longitudinally opposed proximal and distal ends 258a and 258b. The distal ends 258b of the insertion rods 258 may be have engagement tips 258c formed thereon, the engagement tips 258c configured to be received by a fixation plate. In an example embodiment, the engagement tips 258c may define an outer diameter differing from the outer diameter of the distal ends 258b of the insertion rods 258, such that the outer diameter of the engagement tips 258c are uniquely sized to be received within the bores 178 of the fixation plate 156. The engagement tips 258c may have an engagement feature 258d formed thereon, the engagement feature 258d configured to releasably lock the distal ends 258b of the insertion rods 258 within the fixation plate 156. In an example embodiment, the engagement feature 258d may be a raised rib designed to engage with the retaining shelf 166 of the fixation plate 156 when a respective insertion rod 258 is inserted into the fixation plate 156 and rotated into a locked position. In alternative embodiments, the insertion rods 258 may be locked to the fixation plate utilizing other engagement features 258d, for example a ball and detent mechanism installed within the engagement tips 258c of the engagement rods 258, a series of gripping teeth defined on the engagement tip 258c, etc.

The insertion rods 258 may each have a channel 260 formed within the surface thereof between the proximal and distal ends 258a and 258b, the channels configured to directly oppose each other, facing inwardly, when the insertion rods 258 are locked in place within the fixation plate 156 in an assembled insertion configuration. The channels 260 may be configured to slidably receive lateral wings 276 coupled to the body 238 and/or the shaft 240 of the drive head 236, such that the drive head may translate between the proximal and distal ends 258a and 258b of the insertion rods 258 when the lateral wings are received with the channels 260. The channels 260 may be augmented by drop-in bores 262 formed within the outer surfaces of the insertion rods 258, the drop-in bores 262 configured to allow additional components of the intervertebral implant system 100, for example the drive 236 configured with the lateral wings 276, to be inserted into the channels 260 when the insertion rods 258 are already in an assembled configuration. Gripping features 264 may be formed within the outer surfaces of the insertion rods 258 between the proximal and distal ends 258a and 258b, the gripping features 264 configured to facilitate easier gripping of the insertion rods 258, for example as they are rotated into a locked position within the fixation plate 156. In an example embodiment, the gripping features 264 include a series of longitudinal grooves formed radially around the outer surfaces of the insertion rods, although any other gripping features may be used as appropriate. The proximal ends 258a of the insertion rods 258 may be configured to be received and lockably engaged within posterior bores 268 of an end block 266. For example the proximal ends 258a of the insertion rods may have one or more apertures (not shown) formed therethrough configured to accept a pin or other connector, may be have threads formed thereon configured to engage with complimentary threads formed within the end block 266, and so on.

The end block 266 may be defined by an anterior surface 266a, a posterior surface 266b opposite the anterior surface, lateral surfaces 266c, and upper and lower surfaces 266d and 266e. Posterior bores 268 may be formed within the posterior surface 266b of the block 266, the posterior bores 268 configured to receive the proximal ends 258a of the insertion rods 258. Opposing rod grooves 270 may be formed within the end block 266, the rod grooves 270 bounded by the lower and laterally facing quadrants of the posterior bores, extending outwardly to the lateral and bottom surfaces 226c and 266e respectively. The rod grooves 270 may be configured to allow the insertion of retaining members 272 through the rod grooves 270 and into the proximal ends 258a of the insertion rods 258. The retaining members 272 function to secure the insertion rods 258 within the posterior bores 268, while still permitting the rotation of the insertion rods 258, as limited by the lateral and lower facing surfaces of the rod grooves 270. The retaining members 272 may be, for example, pins, posts, screw-type anchors, or the like. An accessory bore 274 may be formed within the anterior surface 266a of the block 266, the accessory bore 274 configured to receive an accessory. The inner surface 274a of the accessory bore 274 may be configured with engaging features, for example helical threads, configured to engage complimentary engagement features formed on an accessory. Accessories may be configured to facilitate easier use of the delivery instrument 278 in positioning and/or insertion of an intervertebral implant assembly into an intervertebral space, and may include a "pistol" grip, a handle, a slap hammer, a slide hammer, or the like.

In an example method of using the delivery instrument 278 to insert and secure an example assembly of the intervertebral implant system 100, an intervertebral implant 148 may mated with a fixation plate 156 to create an implant assembly. The intervertebral implant 148 may be packed, for example with bone growth inducing substances, as appropriate. The engagement tips 258c of the insertion rods 258 may be inserted into and locked in place within the fixation plate 156. In an example embodiment, the insertion rods 258 are locked into place by first inserting the engagement tips 258c into the fixation plate, then rotating the insertion rods 258 one quarter turn to engage the raised ribs 258d with the retaining shelves 166 in the fixation plate 156. The delivery instrument 278 may then be used to position and insert the implant assembly into an intervertebral space. When the implant assembly has been positioned within the intervertebral space, the lateral wings 176 of the assembly carrying the retaining ring 232 and drive head 236, along with one or more pre-loaded arcuate fixation members 12C, may be placed into position in the channels 260 via the drop-in bores 262, and slid into position so that the arcuate fixation members 12C are aligned with the arcuate grooves of the fixation plate 156. The arcuate fixation members may then be driven into position. The implant insertion process may be completed with the installation of an optional blocking plate 180 and a final tightening of a locking screw 138.

Figure 14C:
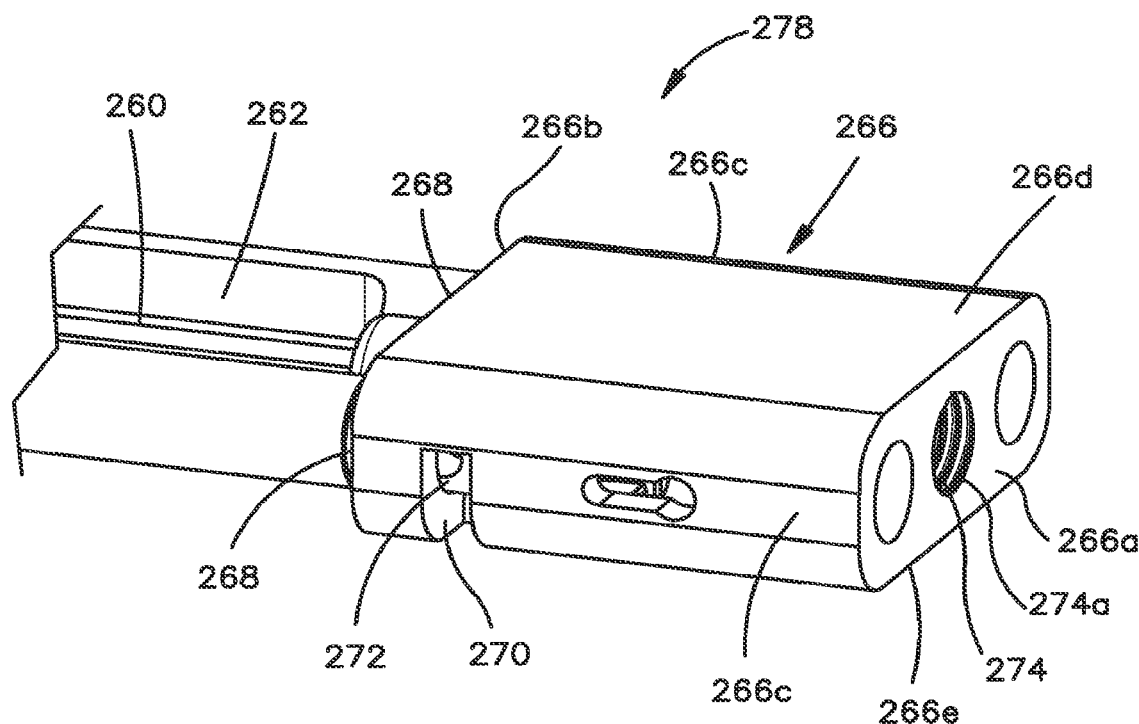
FIG. 14C is a perspective view of another of the components illustrated in FIG. 14A.
Figure 14D:
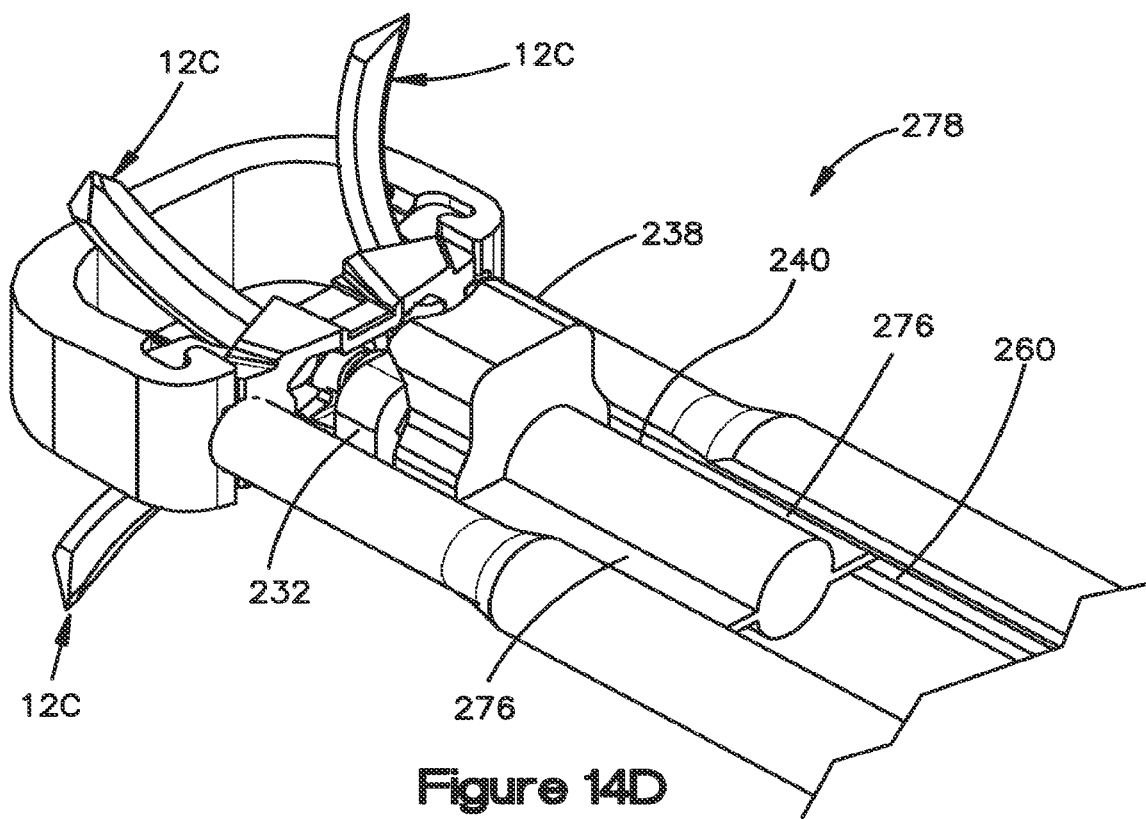
FIG. 14D is a perspective view of components illustrated in FIG. 14A.
Figure 14E:
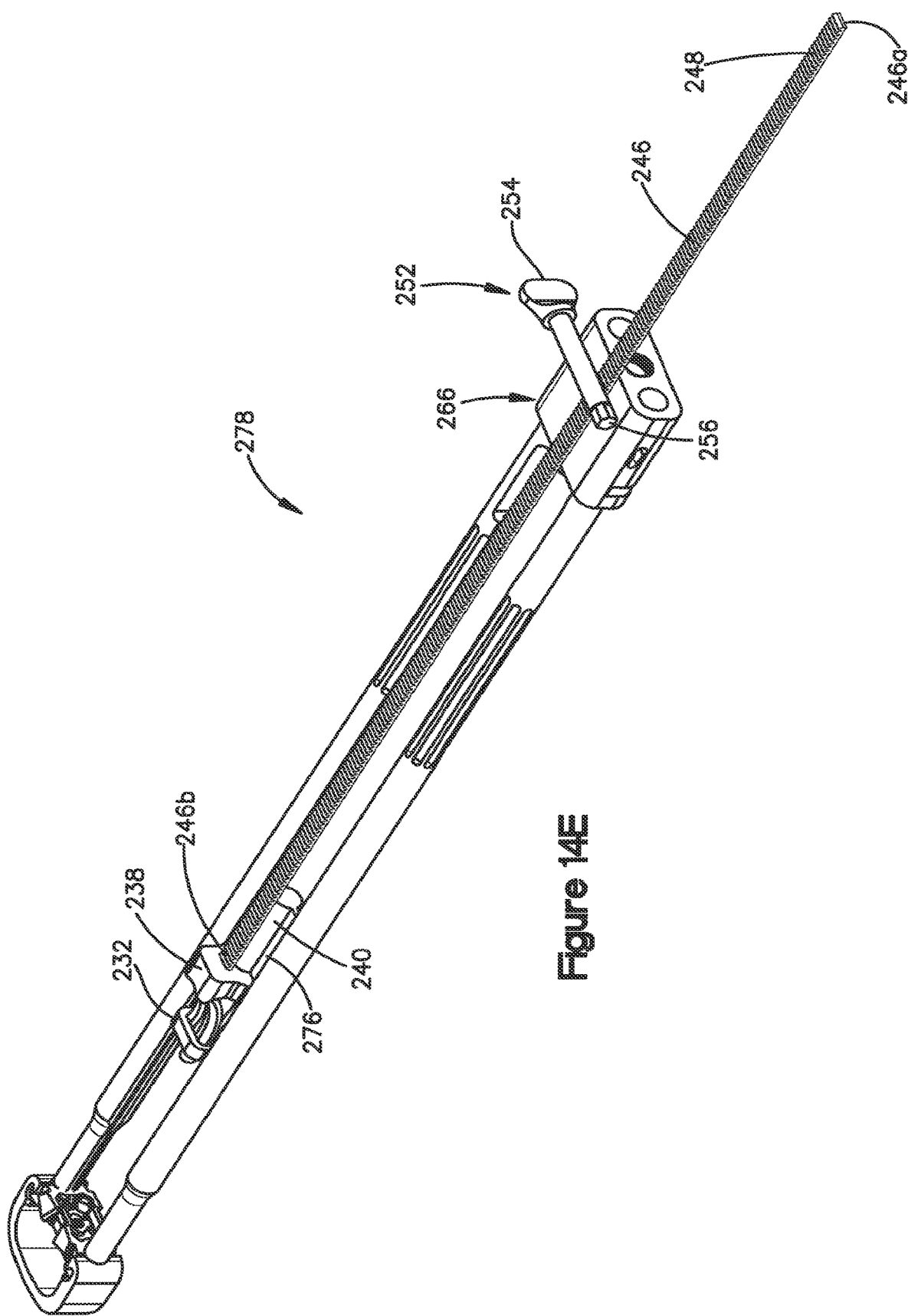
FIG. 14E is a perspective view of another embodiment of the delivery instrument illustrated in FIGS. 14A to 14D.

Various techniques may be utilized to actuate the drive head 236, thereby causing it to drive one or more arcuate fixation members 12C into position. In an example embodiment, the drive head 236 may be advanced towards the distal ends 258b of the insertion rods 258 by a series of impaction forces applied to the drive head 236. The impaction forces may be applied manually, for example by a surgeon via the use of a mallet, or mechanically, for example by a successive series of impactional strikes from a sonic hammer. In an alternative embodiment, the drive head 236 may be advanced via a mechanical drive system. For example, a rack and pinion system may be employed, as illustrated in FIG. 14E. A rack 246 includes a proximal end 246a and a distal end 246b opposite the proximal end, the distal end 246b coupled to the drive head body 238 and/or the shaft 240. The rack may have a series of teeth 248 defined thereon between the proximal and distal ends 246a and 246b. The end block 266 may have a guide channel formed within the upper surface 266d, the guide channel configured to slidably receive the rack 246 therein. A pinion drive 252 may be coupled to the end block 266, for example on the upper surface 266d, such that one or more pinion gears (not shown) of the pinion drive 252 engage the teeth 248 of the rack 246. The pinion drive 252 may be configured with a manual actuator 254 and/or an adapter 256, the adapter 256 configured to couple with a motorized source of rotational force. When the pinion drive 252 is actuated, via either the manual actuator 254 and/or a rotational force applied via the adapter 256, the rack 246, and consequently the drive head 236, may be translated in a direction toward the distal ends 258b of the insertion rods 258, such that the arcuate fixation members 12C are driven into position.

It should be appreciated that a variety of kits can be provided that one or more components of the fixation system 10 or the intervertebral implant system 100. The components of the kits may be configured the same or differently. For example, within a single kit, arcuate fixation members 12A, 12B, and/or 12C may be provided that have varying lengths, differing radii of curvature, differing head and/or tab configurations, differing cross sectional geometries, and so on, depending for example on the type of procedure being performed by a surgeon, or on the particular anatomies of individual patients. The kits may also be configured differently with respect to which components of the individual systems are included in the kits. For example, a kit of the fixation system 10 may include arcuate fixation members 12A and/or 12B with varying configurations and/or features, and may or may not include guiding members 14, and other fixation components such as fixation rods and the like. In another example, a kit for the intervertebral implant system 100 may include arcuate fixation members 12C of varying lengths, radii of curvature, and/or features, and may include one or more of intervertebral implants 108 or 148, fixation plates 116 or 156, blocking plates 132 or 180, ratchet plate 166, or locking screws 138. Example kits for the fixation system 10 and the intervertebral implant system 100 may also include the respective delivery instruments 66, 208, and/or 278.

Although arcuate fixation members and the other components of the fixation system 10 and the intervertebral implant system 100 have been described herein with reference to preferred embodiments or preferred methods, it should be understood that the words which have been used herein are words of description and illustration, rather than words of limitation. For example, it should be appreciated that the structures and/or features of components of the fixation system 10 may be combined with or otherwise integrated with the structures and/or features of the intervertebral implant system 100, unless otherwise indicated. Furthermore, it should be noted that although the fixation system 10 and the intervertebral implant system 100 have been described herein with reference to particular structure, methods, and/or embodiments, the scope of the instant disclosure is not intended to be limited to those particulars, but rather is meant to extend to all structures, methods, and/or uses of the fixation system 10 and the intervertebral implant system 100. Those skilled in the relevant art, having the benefit of the teachings of this specification, may effect numerous modifications to the fixation system 10 and/or the intervertebral implant system 100 as described herein, and changes may be made without departing from the scope and spirit of the instant disclosure, for instance as recited in the appended claims.

What is claimed:
1. An intervertebral implant, comprising:
an implant body defining a first bone-engaging surface, a second bone-engaging surface spaced from the first bone engaging surface along a transverse direction, a posterior end, an anterior end spaced from the posterior end along a longitudinal direction that is perpendicular to the transverse direction, and opposed lateral sides spaced apart with respect to each other along a lateral direction that is substantially perpendicular to the transverse direction and the longitudinal direction, the opposed lateral sides extending between the first and second bone-engaging surfaces;
a fixation plate attached to the implant body, the fixation plate defining a posterior surface, an anterior surface spaced from the posterior surface along the longitudinal direction, lateral sides opposite each other along the lateral direction, first and second access grooves located at the lateral sides of the fixation plate, and first and second engagement elements located within the first and second access grooves and configured for engagement with a delivery instrument, the fixation plate further defining at least one curved aperture having an anterior end, a posterior end, and a curved aperture axis that extends from the anterior end toward the posterior end, wherein the at least one curved aperture is located between the first and second access grooves with respect to the lateral direction;
at least one curved fixation member elongate along a curved central axis and configured to be received within the at least one curved aperture, the at least one curved fixation member having a proximal end and a distal end spaced from the proximal end along the curved central axis, the distal end defining a tip configured to cut into a vertebral body, wherein the at least one curved fixation member has a length greater than the at least one curved aperture such that the tip can be driven through the at least one curved aperture and into the vertebral body; and a blocking plate configured to be coupled to the fixation plate so as to secure the at least one curved fixation member to the fixation plate, the fixation plate defining a bore configured to receive a locking member that couples the blocking plate to the fixation plate, the bore being disposed between the opposed lateral sides of the implant body with respect to the lateral direction.

2. The intervertebral implant of claim 1, wherein the at least one curved fixation member has a curved intermediate portion positioned between the proximal and distal ends, the curved intermediate portion having a cross-sectional shape configured to reside within a conformal cross-sectional shape of the at least one curved aperture, and the conformal cross-sectional shapes are defined with respect to the transverse and lateral directions.

3. An intervertebral implant system, comprising:
the intervertebral implant of claim 1; and
a delivery instrument attachable to the fixation plate, the delivery instrument having respective first and second engagement tips that are insertable within the first and second access grooves, respectively, of the fixation plate, the first and second engagement tips having first and second engagement members that are configured to releasably grip the first and second engagement elements, respectively, of the fixation plate, the delivery instrument further comprising a guide slot that is aligned with the curved aperture of the fixation plate when the delivery instrument is attached to the fixation plate, wherein the curved fixation member is advanceable along the guide slot and through the curved aperture and into the vertebral body.

4. The intervertebral implant system of claim 3, wherein the guide slot is arcuate.

5. The intervertebral implant system of claim 3, wherein:
the at least one curved aperture of the fixation plate comprises first and second curved apertures that are both located between the first and second access grooves with respect to the lateral direction;
the guide slot of the delivery instrument is a first guide slot; and
the delivery instrument defines a second guide slot that is alignable with the second curved aperture of the fixation plate when the delivery instrument is attached to the fixation plate.

6. The intervertebral implant system of claim 3, wherein at least one of the first and second engagement members of the delivery instrument comprises a rib, at least one of the first and second engagement elements of the fixation plate comprises a shelf, and the rib is configured to engage the shelf to releasably attach thereto.

7. The intervertebral implant system of claim 3, wherein at least one of the first and second engagement members of the delivery instrument is rotatable within an associated at least one of the first and second access grooves, so as to cause the at least one of the first and second engagement members to releasably grip a respective one of the first and second engagement elements.

8. An intervertebral implant system, comprising:
an intervertebral implant insertable within an intervertebral space between superior and inferior vertebral bodies, the intervertebral implant having a fixation plate that defines first and second access grooves located at lateral sides of the fixation plate, wherein the lateral sides are opposite each other along a lateral direction, the fixation plate has first and second engagement elements within the first and second access grooves, and the fixation plate has a curved aperture located between the first and second access grooves with respect to the lateral direction;

a delivery instrument attachable to the fixation plate, the delivery instrument having respective first and second engagement tips that are insertable within the first and second access grooves of the fixation plate for releasably gripping the first and second engagement elements of the fixation plate, wherein the delivery instrument comprises a guide slot that is alignable with the curved aperture of the fixation plate; and a curved fixation member having a proximal end and a distal tip, wherein the proximal end of the curved fixation member is configured receive a drive force to advance the curved fixation member along the guide slot defined in a guide member of the delivery instrument and through the curved aperture defined in the fixation plate such that the distal tip of the curved fixation member exits the curved aperture and cuts into one of the superior and inferior vertebral bodies.

9. The intervertebral implant system of claim 8, comprising a drive member that is advanceable against the proximal end of the curved fixation member to apply a drive force to the curved fixation member to advance the curved fixation member along the guide slot and through the curved aperture.

10. The intervertebral implant system of claim 8, wherein the intervertebral implant comprises a blocking body positionable behind at least a portion of the proximal end of the curved fixation member, and the blocking body is affixable to the fixation plate so as to secure the proximal end of the curved fixation member to the fixation plate.

11. The intervertebral implant system of claim 10, wherein the blocking body is movable within a recess formed in an anterior surface of the fixation plate.

12. The intervertebral implant system of claim 10, wherein the curved fixation member has a head at the proximal end thereof, and the head is configured to receive a drive force for advancing the head toward the curved aperture until at least a portion of the head resides within the recess.

13. The intervertebral implant system of claim 8, wherein:
the guide slot is a first guide slot and the guide member defines a second guide slot spaced from the first guide slot along the lateral direction, and
the curved aperture is a first curved aperture and the fixation plate defines a second curved aperture spaced from the first curved aperture along the lateral direction.

14. The intervertebral implant system of claim 13, further comprising a second curved fixation member configured for insertion along the second guide slot and through the second curved aperture, thereby causing a second distal tip of the second curved fixation member to exit the second curved aperture and cut into one of the superior and inferior vertebral bodies.

15. The intervertebral implant system of claim 14, wherein:
one of the first and second curved apertures curves upward from a proximal side of the fixation plate to an opposed distal side of the fixation plate, such that the distal tip of one of the first and second curved fixation members is configured to exit the one of the first and second curved apertures and cuts into the superior vertebral body, and the other of the first and second curved apertures curves downward from the proximal side to the distal side of the fixation plate, such that the distal tip of the other of the first and second curved fixation members is configured to exit the other of the first and second curved apertures and cuts into the inferior vertebral body.

16. The intervertebral implant system of claim 8, wherein the intervertebral implant comprises an implant body having superior and inferior bone-engaging surfaces opposite each other along a transverse direction that is perpendicular to the lateral direction, the fixation plate is attachable to the implant body, and the implant body defines a plurality of gripping structures formed on at least one of a superior bone-engaging surfaces for engaging at least one of the superior and inferior vertebral bodies.

17. The intervertebral implant system of claim 16, wherein the implant body defines lateral walls spaced from each other along the lateral direction and a distal wall spaced from the fixation plate along a third direction that is perpendicular to the lateral and transverse directions, wherein the intervertebral implant has at least one bore that extends along the transverse direction and is located between the lateral walls of the implant body along the lateral direction.

18. The intervertebral implant system of claim 17, wherein the at least one bore is configured to receive a bone growth inducing substance prior to inserting the intervertebral implant into the intervertebral space.

19. The intervertebral implant system of claim 8, wherein the curved fixation member comprises a curved intermediate portion located between the proximal end of the curved fixation member and the distal tip, and the curved intermediate portion is configured to extend within the curved aperture of the fixation plate.

20. The intervertebral implant system of claim 19, wherein the curved intermediate portion has a cross-sectional shape configured to reside within a conformal cross-sectional shape of the curved aperture, and the conformal cross-sectional shapes are defined with respect to the transverse and lateral directions.

* * * * *